United States Patent
Selden et al.

(10) Patent No.: US 12,378,544 B2
(45) Date of Patent: Aug. 5, 2025

(54) SYSTEMS AND METHODS FOR RAPID NUCLEIC ACID EXTRACTION, PURIFICATION AND ANALYSIS FROM SEMEN

(71) Applicant: ANDE Corporation, Waltham, MA (US)

(72) Inventors: Richard F. Selden, Lincoln, MA (US); Rosemary Turingan Witkowski, Stoneham, MA (US)

(73) Assignee: ANDE Corporation, Waltham, MA (US)

(*) Notice: Subject to any disclaimer, the term of this patent is extended or adjusted under 35 U.S.C. 154(b) by 935 days.

(21) Appl. No.: 17/492,318

(22) Filed: Oct. 1, 2021

(65) Prior Publication Data

US 2022/0017889 A1    Jan. 20, 2022

Related U.S. Application Data

(62) Division of application No. 15/898,156, filed on Feb. 15, 2018, now Pat. No. 11,168,318.

(60) Provisional application No. 62/545,248, filed on Aug. 14, 2017, provisional application No. 62/459,542, filed on Feb. 15, 2017.

(51) Int. Cl.
| | |
|---|---|
| *C12Q 1/68* | (2018.01) |
| *C12N 15/10* | (2006.01) |
| *C12P 19/34* | (2006.01) |
| *C12Q 1/6806* | (2018.01) |
| *C12Q 1/6869* | (2018.01) |

(52) U.S. Cl.
CPC ....... *C12N 15/1003* (2013.01); *C12Q 1/6806* (2013.01); *C12Q 1/6869* (2013.01); *C12Q 2527/125* (2013.01); *C12Q 2527/137* (2013.01)

(58) Field of Classification Search
CPC .................................................. C12Q 1/6888
See application file for complete search history.

(56) References Cited

U.S. PATENT DOCUMENTS

| | | | |
|---|---|---|---|
| 2008/0176320 A1* | 7/2008 | Liu | C12Q 1/6806 435/325 |
| 2011/0159485 A1 | 6/2011 | Stray | |
| 2016/0123853 A1 | 5/2016 | Inostroza Silva | |

FOREIGN PATENT DOCUMENTS

CN    101225444 A    7/2008

OTHER PUBLICATIONS

Wu et al., Biotechniques 58(6), 293-300 (2015) (Year: 2015).*
Hagelberg et al. "Isolation and Characterization of DNA from Archaeological Bone," Proceedings: Biological Sciences, 244(1309): 45-50 (Apr. 22, 1991).
Higgins, Denice et al. "Evaluation of Carrier RNA and Low Volume Demineralization for Recovery of Nuclear DNA from Human Teeth", Forensic Science, Medicine and Pathology, Mar. 2014, vol. 10, No. 1 Mar. 2014 (Mar. 2014), pp. 56-61; 1556-2891.
Lee, Hy et al. "Simple and Highly Effective DNA Extraction Methods from Old Skeletal Remains Using Silica Columns," Forensic Science International: Genetics, Elsevier Bv, Netherlands, vol. 4, No. 5, Oct. 1, 2010 (Oct. 1, 2010) pp. 275-280.
Rohland, Nadin et al. "Ancient DNA Extraction From Bones and Teeth," Nature Protocols, vol. 2, No. 7, Jul. 1, 2007, pp. 1756-1762.
Rohland, Nadin et al. "Comparison and Optimization of Ancient DNA Extraction and Supplementary Material," Biotechniques Rapid Dispat, Informa Healthcare, US, vol. 42, No. 3, Mar. 1, 2007 (Jan. 3, 2007), pp. 343-352.
Turingan, R.S., et al. "Rapid DNA Analysis for Automated Processing and Interpretation of Low DNA Content Samples," Investigative Genetics 20160317 Biomed Central Ltd Gbr, vol. 7, No. 1, Mar. 17, 2016 (Mar. 17, 2016).
International Search Report for PCT/US2018/018438, dated Apr. 18, 2018 (6 pgs.).
International Preliminary Examination Report for PCT/US2018/018438, dated Aug. 20, 2019 (14 pgs.).
Korlevic et al., "Reducing microbial and human contamination in DNA extractions from ancient bones and teeth," BioTechniques, 2015, vol. 519, No. 2, pp. 87-93.
Prado et al., "Comparison of extraction methods for the recovery, amplification and species-specific analysis of DNA from bone and bone meals," Electrophoresis, 2002, vol. 23, pp. 1005-1012.
Tan et al., "Fully integrated, fully automated generation of short tandem repeat profiles," Investigative Genetics, 2013, vol. 4, No. 6., pp. 1-15.

* cited by examiner

*Primary Examiner* — Kenneth R Horlick
(74) *Attorney, Agent, or Firm* — Proskauer Rose LLP

(57) ABSTRACT

Disclosed are processes and kits for rapid nucleic acid extraction from a nucleic acid-containing material, such as a bone, tooth or semen sample. For bone and tooth process involves providing the nucleic acid-containing material in a form suitable for nucleic acid extraction, adding a lysis buffer to the nucleic acid-containing material to obtain a mixture, mixing the mixture in a manner equivalent for about 30 seconds or longer and separating the mixture by centrifugation to obtain a liquid supernatant. The liquid supernatant contains the extracted nucleic acids which can be used for analysis including STR profiling by conventional or rapid DNA analysis. For semen the processes and kits involve applying an appropriate amount of sperm disruptive agent.

3 Claims, 51 Drawing Sheets

ANDE SAK KIT

- TUBE 1 WITH PROTEINASE K (ProK) - TUBE CONTAINED IN A SEALED FOIL BAG, ROOM TEMPERATURE
- REAGENT 1 - ANDE LYSIS SOLUTION (LS), ROOM TEMPERATURE
- SAK SWAB
- TRANSPORT TUBE, ROOM TEMPERATURE
- SPIN BASKET, ROOM TEMPERATURE
- TUBE 2 (BLANK)
- TUBE 3 WITH LYOPHILIZED DNaseI
- REAGENT 2 - DNaseI BUFFER
- REAGENT 3 - EDTA STOP SOLUTION
- REAGENT 4 - REDUCING AGENT
- ANDE SWAB, ROOM TEMPERATURE

FIG. 27

SYSTEMS AND METHODS FOR RAPID NUCLEIC ACID EXTRACTION, PURIFICATION AND ANALYSIS FROM SEMEN

CROSS-REFERENCE TO RELATED APPLICATIONS

This Application is a Divisional Application of U.S. patent application Ser. No. 15/898,156, filed Feb. 15, 2018, now issued as U.S. Pat. No. 11,168,318, and claims the benefit of U.S. Provisional Patent Application No. 62/545,248, filed Aug. 14, 2017 and U.S. Provisional Patent Application No. 62/459,542, filed Feb. 15, 2017, each of which is incorporated herein by reference in their entireties.

FIELD OF INVENTION

The invention relates to systems and processes for nucleic acid extraction, purification, and analysis. More specifically, in one aspect, the invention relates to rapid purification and analysis of nucleic acids from samples including bone, tooth, and semen samples obtained from forensic, missing persons, and mass casualty settings.

BACKGROUND

In forensic science, a major objective is to identify sources of biological evidence such as bone, tooth, blood, semen, saliva, and hairs found at the scene of crimes, terrorist activities and attacks, and mass disaster sites. DNA profiling has provided a means of identifying the source of such material with a very high degree of certainty. In the forensic science community today, most DNA profiling methods are based on the amplification of small regions of the human genome containing a class of repeated DNA stretches known as Short Tandem Repeats (STRs). The unit length of a given STR typically ranges between 2-10 base pairs, and STRs generally fall within non-coding and flanking sequences but occasionally within coding regions. There are several hundred thousand STR loci in the human genome, occurring on average every 6-10 kb and appearing to be highly polymorphic. The number of repeats at a given STR site or locus in the genome is characteristic of the cells of an individual, and by determining the number of repeats at several STR loci, a characteristic "DNA fingerprint" (also referred to as an "STR profile" or "DNA ID") of an individual can be generated.

STR profiles are generated by a series of three basic processes. First, DNA is purified from the cells on a sample collection device or substrate, (e.g., a swab). This involves breaking open the cells to free the DNA and then removing proteins, other biomolecules, and cellular debris to generate a purified or partially purified DNA solution. Second, the set of STR loci are copied (amplified) using a process known as Polymerase Chain Reaction (PCR). Primers that bind to target STR gene regions are labeled with fluorescent dyes so amplified fragments containing said primers can be detected by laser-induced fluorescence. A large number of dyes (greater than 50) are available for use in fluorescence excitation applications. These dyes include those from the fluorescein, rhodamine AlexaFluor, Biodipy, Coumarin, and Cyanine dye families. Furthermore, quenchers are also available for labeling oligonucleotide sequences to minimize background fluorescence. Dyes with emission maxima from 410 nm (Cascade Blue) to 775 nm (Alexa Fluor 750) are available and can be used. Dyes ranging between 500 nm to 700 nm have the advantage of being in the visible spectrum and can be detected using conventional photomultiplier tubes. The broad range of available dyes allows selection of dye sets that have emission wavelengths that are spread across the detection range. Detection systems capable of distinguishing many dyes have been reported for flow cytometry applications (see, Perfetto et al., *Nat. Rev. Immunol.* 2004, 4, 648-55; and Robinson et al., *Proc of SPIE* 2005, 5692, 359-365).

Fluorescent dyes have peak excitation wavelengths that are typically 20 to 50 nm blue-shifted from their peak emission wavelength. As a result, use of dyes over a wide range of emission wavelengths may require the use of multiple excitation sources, with excitation wavelengths to achieve efficient excitation of the dyes over the emission wavelength range. Alternatively, energy transfer dyes can be utilized to enable a single laser, with a single emission wavelength, to be used for exciting all dyes of interest. This is achieved by attaching an energy transfer moiety to the dye label. This moiety is typically another fluorescent dye with an absorption wavelength that is compatible with the excitation wavelength of the light source (e.g. laser). Placement of this absorber in close proximity with an emitter allows the absorbed energy to be transferred from the absorber to the emitter, allowing for more efficient excitation of the long wavelength dyes (Ju et al., *Proc Natl Acad Sci USA* 1995, 92, 4347-51). A fourth dye is used as a standard marker for determining the size of the STR fragments.

Third, the size of the copied STR fragments is determined by electrophoresis. The STR fragments are pulled by an electric current through a gel-like substance, and the smaller fragments travel more quickly through the gel than the larger fragments. At a detection window, a laser is used to excite the four fluorescent dyes. The dyes emit light, which is then detected and used to determine the size of each STR fragment. An Expert System, operated either automatically or manually, analyses the size pattern and generates the final STR profile—the individual's DNA fingerprint. Note that the three basic steps of DNA fingerprint generation may be modified; for example, cells in a sample may be lysed, and the resulting cell extract moved to amplification (without the DNA purification). Similarly, amplified DNA fragments can be identified by methods including mass spectroscopy.

STR analysis was first applied in the early 1990's and has since become a major tool in the forensic armamentarium with a growing set of applications including law enforcement, paternity testing, human identification in mass disasters, immigration and sexual assault cases, unclaimed minor (child) verification and human trafficking. In the United States, STR profiles generated from selected human samples are collected in the Combined DNA Index System (CODIS). This electronic database was established in 1997 by the FBI and standardized to a set of 13 tetrameric STR loci for data submission, and, in January 2017, the number of core loci to be utilized in FBI databases expanded to 20. Other STR databases outside the US contain overlapping subsets of the CODIS loci. In order to generate a DNA profile, a critical first step is to obtain DNA from the sample of interest.

Forensic samples present special challenges. The inventions presented here provide solutions for bone, tooth, and semen samples, among the most difficult for processing in forensic laboratories. For bone and tooth, there is no universal protocol that allows for extraction of DNA from materials at different stages of degradation. The efficiency of DNA extraction, the level of demineralization, the problem of low content of DNA in the sample, the degree of contamination by inhibitors all present significant challenges. At least two types of semen samples are relevant. First, a semen stain containing a relatively pure population of sperm may be found on, for example, an article of clothing or on the exposed skin of a rape victim. Second, Sexual Assault Kit samples (SAKs) often contain vaginal swabs or cervical swabs—such swabs may contain mixtures of vaginal and cervical cells (including vaginal and cervical epithelial cells) and sperm. In addition, both semen sample types may contain cells from more than one male—whether derived from a consensual partner or an additional rapist. Separation of male and females cells and deconvolution of mixtures also present challenges.

A related challenge relates to the development and use of processing protocols, including processing protocols for Rapid DNA Identification. Processing protocols are very important in many different fields. Processing protocols are created and followed to ensure that similar sample types are processed in the same way. The use of such protocols helps provide consistent processing results, and where the results are not consistent, ensures that the differences are not attributable to variances caused by the processing itself. With regard to STR analysis, certain protocols must be followed not only as a matter of sound scientific principles, but also to stay within compliance with federal regulations. Protocols that have been developed for manual processing or without regard to field-forward use or rapid processing may be entirely unsuitable to forensic use, including field forward forensics. We present herein novel inventive protocols that solve the unique problems presented by the necessity of automated processes, fast protocols, and forensic samples.

There are still major challenges in efficient nucleic acid purification from certain biological evidence such as bone. Bone is a good source of nucleic acid under scenarios where the biological evidence has been exposed to a variety of environmental conditions because the bone matrix protects nucleic acids from degradation. Current methods of nucleic acid extraction from bone are generally cumbersome, lengthy, and inefficient in that it takes hours or even days to obtain quality nucleic acids suitable for analysis. Bone and tooth purification protocols are based on extraction and purification of DNA from bone or tooth powder pulverized by a freezer mill or blending cup (Loreille et al, FSIG 1 (2007), 191-195; Johnston and Stephenson, JFS 61 (2016), 898-902; Turingan et al, Inv. Genetics 7 (2016), bone slices generated using a rotary dental saw or its equivalent (Kitayama et al, Legal Med 12 (2010), 84-89), and related protocols. The need to initiate the process with powder requires cumbersome equipment and limits the techniques to sophisticated laboratories. In addition, pulverization equipment and dental cutting discs can cause the production of airborne biological material, with attendant health risks to operators as well as attendant risks of sample-to-sample contamination. Furthermore, extensive demineralization of the bone powder or bone slices, often requiring overnight demineralization at elevated temperatures with agitation (See, e.g., Lee H Y et al., Forensic Science International: Genetics, 4 (2010) 275-280) also take time and sophisticated equipment. Finally, the protocols of the prior art are based on large volumes of demineralization buffer relative to the amount of the bone powder to be demineralized and rely on complex reagent mixes. The large volumes of demineralization buffer requires concentration (often using a concentration membrane) in order to obtain an appropriate volume for subsequent processing (e.g. purification) and analysis. Concentration is yet another step that adds time and complexity to the overall process. Taken together, it is no wonder why the time to generation of STR profiles from bone is a major problem in law enforcement forensic laboratories, coroners' offices, and Offices of Chief Medical Examiners.

To date, STR analysis of bone and tooth powder has been performed in conventional laboratories. The investment in labor, instrumentation, and time has dramatically limited the utility of this approach. Many forensic laboratories send out bone and tooth processing to highly specialized laboratories that can take a year or more to return DNA fingerprint results and have limited capacity to do even that. As a result, it is estimated that 40-80,000 unidentified corpses are now in medical examiners' and coroners' offices, and many are buried or cremated before they can be identified. Similarly, even a relatively small disaster such as a plane crash can take years for body parts to be identified by forensic laboratories. When large mass disasters occur, bodies may be unidentified for years or decades. The 2004 Indian Ocean earthquake and tsunami is a tragic example—more than a decade later, thousands of victims remain unidentified.

Both conventional and rapid DNA analysis systems would both benefit greatly from faster, simpler, and more efficient processing of samples of interest. The processes and kits in the present invention are surprising in the following aspects. First, in the present invention, the need for generating bone or tooth powder has been eliminated. Unexpectedly, a few blows of a hammer or a mortar and pestle or a brick (or similar material) macerate the sample sufficiently for further processing. The surface area generated for demineralization by hammering surprisingly generates sufficient surface area to enable efficient demineralization while avoiding the generation of airborne bone particles. Second, the process of demineralization of bone samples takes less than 60 minutes, with ten minutes being generally applicable and only one minute being sufficient in many instances. For tooth, the process of demineralization takes approximately 180 minutes, with ten minutes being sufficient in many instances. Third, prior art protocols require overnight demineralization to extract nucleic acids from bone powder and slices, often with heating steps that can damage DNA. See Higgins et al, Forensic Sci Med Pathol 2014, 10:56-61; Amory et al., Forensic Science International: Genetics 6 (2012) 398-406; Loreille et al. Forensic Science International: Genetics 1 (2007) 191-195; and Lee et al. Forensic Science International: Genetics 4 (2010) 275-280. In the Loreille method, total dissolution of bone powder using a large volume of buffer was necessary for analysis, and organic extraction for purifying DNA followed by sample concentration was necessary. The Loreille method, therefore, requires excessive sample manipulation and time, both of which limit the process to a sophisticated and well-equipped laboratory and dramatically limit the processing capacity of the laboratory at that. Higgins is a modification of the Loreille method which, while using lower volume assays, still requires an overnight incubation and laborious purification. In addition, the protocol requires the use of carrier RNA which is an additional reagent and involves additional processing steps. The carrier RNA is taught to be added to increase DNA yield, however the addition does not result in enhanced DNA recovery. The Lee method uses more reagents and is even more complex than either Loreille or Higgins. Fourth, standard methods use large volumes of demineralization buffer, which makes handling of the solutions and subsequent DNA concentration and purification more challenging for conventional and Rapid DNA analysis. Taken together, none of these methods are appropriate for field-forward Rapid DNA Identification.

Fourth, the processes of the invention also use specialized reagents, including demineralization reagents. In the present invention, the demineralization solution contains only minimal EDTA buffer volume and involves a quick demineralization prior to downstream purification from bone and STR profile generation. We demonstrate herein unexpected results, including that demineralization solutions that may contain lysis buffer/detergent and proteinase K need not contain EDTA in a high initial volume (~15 ml for complete dissolution of 1 g sample). Prior art methods using lysis buffer/detergent and high initial volumes of EDTA teach the use of a long incubation step followed by sample concentration prior to DNA purification. We demonstrate the unexpected finding that these steps are not necessary. Similarly, prior art protocols for DNA extraction from demineralized bone and tooth involve an organic extraction method. Prior art protocols for isolating nucleic acid from semen samples require the use of complex reagents and long processing steps necessary to isolate and lyse the cells from the mucous environment in which they usually are found, including centrifugation, washing, and incubation steps. We demonstrate herein novel, unexpected protocols for isolating nucleic acid from bone, teeth and semen samples that shatter the conventional wisdom.

The simplified solutions and protocols of this invention not only reduce reagent and material cost but substantially decrease processing time and potential for sample loss during extensive manipulation. Indeed, this invention is based, in part, on the unexpected finding that there is no need to completely dissolve the sample for a total demineralization with longer incubation and high buffer volume for generation of callable STR profiles. The solutions and protocols of this invention are easily adapted for use in integrated biochip and instrument systems which are capable of sample-in to results-out processing.

The solutions and protocols of this invention are able to extract nucleic acids in sufficient quantities to generate STR profiles that can be uploaded into the CODIS database. For example, from 15 fresh bone samples, using the protocols of the invention, we obtained a nucleic acid yield of 4.2 ng-108.1 ng per mg of bone. In addition, from 12 fresh tooth samples, we obtained a nucleic acid yield of 0.1 ng-2.7 ng per mg of tooth root. Finally, the solutions and protocols of this invention may be adapted for use in high and low DNA content integrated Rapid DNA Identification systems (using A-Chips and I-Chips, respectively), including those capable of sample-in to results-out processing. Automated data processing and automated Expert System analysis may also be incorporated into the Rapid DNA Identification system.

With regard to protocols for DNA extraction from semen, faster, simpler, more efficient methods have been developed that can be utilized for both conventional and Rapid DNA analysis systems. Standard DNA purification methods for somatic cells are ineffective for lysing sperm cells due to their high degree of nuclear compaction and presence of protective membranes rich in disulfide bonds. Modifications to standard lysis methods include addition of a strong reducing agents to disrupt these disulfide bonds that impede lysis. These alternative methods primarily rely on lengthy chaotropic digestion with proteinase K at elevated temperatures and incubation with reducing agent such as dithiothreitol (DTT) to allow consequent isolation and purification of DNA. Rapid methods of mammalian sperm DNA isolation have also been conducted using steel beads for homogenization at room temperature for 5 minutes in the presence of chaotropic lysis buffer and addition of tris(2-carboxyethyl) phosphine (TCEP) instead of DTT (Wu et. al. Biotechniques. 2014; 58(6): 293-300). Although this method substantially decreased time and complexity by eliminating heat and slow incubation and uses an odorless sperm disruption agent, mechanical bead homogenization techniques are not always available and still require highly skilled technicians, sophisticated equipment, and clean-up/bead isolation for downstream processing. In short—a laboratory environment. In the present invention, semen samples are collected on a swab (either prepared from neat semen, dried semen on fabric, carpet, skin, tile or other substrates, or isolated spermatozoa from sexual assault kits) and then a sperm disruption agent (e.g. 150 mM DTT or 50 mM TCEP) is simply added. Incubation of semen on swab at room temperature for 10 minutes, and in many instances for as little as 1 minute, was enough to generate DNA fingerprints using the ANDE Rapid DNA system.

In sexual assault kits, vaginal swabs often contain cells from more than one contributor. Often the swabs will contain cells from the female victim and the male perpetrator. Accordingly, to avoid "mixed" DNA IDs (in which the DNA IDs from two or more individuals in present), spermatozoa may be separated from the vaginal epithelial cells; processing to achieve this separation is necessary prior to DNA extraction and/or purification steps. A differential lysis method was described in 1985 by Gill and colleagues which relies on separating intact sperm from the DNA of lysed epithelial cells. Several modifications to the method to reduce time and improve efficiency have been made over the years, but the fundamental concept and process has remained unchanged. Differential extraction is time-consuming, laborious, and required a sophisticated laboratory and highly-skilled technicians. Physical separation of the intact sperm cells from the lysed female fraction is achieved by centrifugation and repeated washing of the pelleted sperm cells. Alternative methods eliminate the time-consuming wash steps by selective degradation of soluble DNA using nuclease enzyme (Garvin et al Investigative Genetics 2012 3:25). A commercially available kit, Sperm Erase (Paternity Testing Corporation) utilizes the latter approach. Processing of SAKs using prior art methods require between 2 to 5 hours from the initial epithelial cell lysis to the generation of sperm fraction.

The present invention provides a rapid method for lysing epithelial cells which unexpectedly can be performed in ten seconds at room temperature; previous approaches require at least one hour and typically require heat. Furthermore, the present invention provides a method wherein both physical separation and chemical degradation techniques have been efficiently combined to allow effective isolation and purification of sperm cell DNA while reducing overall process time.

In one method of the present invention, the sperm pellet is washed once with wash buffer that is optimized for nuclease activity Eliminating the repeated wash steps not only improves time but also reduces potential sperm cell loss. The wash buffer is stable at room temperature and primes the reaction for the addition of nuclease, hence, one less reagent in an SAK processing kit. The nuclease degrades any soluble DNA and a stop solution containing 0.5 M EDTA is then added to deactivate the enzyme. To allow lysis of the sperm cells, a sperm disruption agent (with final concentrations of approximately 150 mM DTT or 50 mM TCEP) is added to the mixture prior to collecting the liquid with a swab for Rapid DNA analysis. Generation of male fraction was completed in 32 minutes. Decreasing the centrifugation time for initial separation and also decreasing the time to quench the activity of the nuclease allowed generation of sperm fraction for analysis in approximately 22 minutes.

Furthermore, the process steps have been simplified so that they may be performed by non-technical personnel. In fact, the work can be performed outside the forensic lab, by Sexual Assault Nurse Examiners, Forensic nurses, or other hospital personnel. If the work is performed at the hospital (even in a hospital lab), the transport time to the police station/forensic lab is eliminated. Taken together, the teachings of the present invention all rapid generation of an actionable DNA ID result. By generating the result quickly, law enforcement investigations can proceed more quickly leading to suspect apprehension and exoneration of the innocent. As many criminals are recidivists (e.g. the typical rapist commits more than 10 rapes before being apprehended), the teachings herein can be expected to dramatically reduce crime and improve public safety.

BRIEF SUMMARY OF THE INVENTION

In a first embodiment, we provide a process for extracting nucleic acids from a bone or tooth sample, comprising providing the sample in a form suitable for nucleic acid extraction; adding a demineralization buffer to the nucleic acid-containing material to obtain a mixture; mixing the mixture vigorously; and separating the mixture to obtain a liquid supernatant; wherein the liquid supernatant contains the extracted nucleic acids. In related embodiments, the separation step does not involve concentrating the nucleic acid and the demineralization does not result in complete dissolution of the bone sample.

In another embodiment we provide a process for extracting nucleic acids from a bone or tooth sample, comprising: providing the sample in a form suitable for nucleic acid extraction; adding a less than 500 μl 0.5 M EDTA or equivalent demineralization buffer to the nucleic acid-containing material to obtain a mixture; mixing the mixture vigorously; incubating the mixture for at least one minute without adding heat; separating the mixture to obtain a liquid supernatant without concentration wherein the liquid supernatant contains the extracted nucleic acids.

In yet another embodiment, we provide a process for determining STR profiles of nucleic acids from a nucleic acid-containing material, comprising: providing the nucleic acid-containing material in a form suitable for nucleic acid extraction; adding a demineralization buffer to the nucleic acid-containing material to obtain a mixture; mixing the mixture vigorously; separating the mixture to obtain a liquid supernatant; wherein the liquid supernatant contains the extracted nucleic acids; and subjecting a portion of the liquid supernatant to a nucleic acid analysis to determine the STR profile of the nucleic acids from the nucleic acid-containing material.

In another embodiment we provide a process and kits for determining STR profiles of nucleic acids from a semen sample, comprising: collecting semen samples onto a transfer medium; applying an appropriate amount of a sperm disruptive agent onto the transfer medium. In related embodiments the transfer medium may be inserting the swab into a rapid DNA analysis system or otherwise processed for STR analysis.

In another embodiment, A process and kits for isolating female epithelial cells from sperm cells in post-coital vaginal swabs comprising: lysis of epithelial cells from transfer medium; physical separation of intact sperm cells from lysed epithelial cells; removal of the aqueous female fraction from the intact sperm cells; washing of the pelleted intact sperm cells by wash buffer; degradation of any soluble DNA by nuclease treatment; inactivation of nuclease, lysis of sperm cells by a sperm disruption agent (e.g. DTT or TCEP, other chemicals, or physical methods); and collection of the lysed sperm fraction.

In yet another embodiment, we provide a process for extracting nucleic acids from a sample suspected of containing sperm, the process comprising: inserting said sample into a sample container containing a first lysis solution and agitating to make a first mixture; centrifuging said first mixture; washing the pellet in said first container with buffer; second centrifuging the first container to repelletize any sperm present in said sample; transferring at least a portion of the sperm to a second container containing nuclease in a sufficient amount, and under sufficient conditions to degrade DNA; adding a sperm disruption agent; recovering the disrupted sperm fraction for further processing.

As will be apparent to persons of ordinary skill in the art the inventive processes for extraction, purification and analysis of nucleic acids result in outputs that are suitable for further analysis, including without limitation, downstream processing in integrated biochips. The embodiments mentioned in this summary are not intended to limit the claims of this or any related or unrelated application. Other aspects, embodiments, modifications to and features of the claimed invention will be apparent to persons of ordinary skill in the art in view of the disclosures herein.

BRIEF DESCRIPTION OF THE DRAWING

FIG. 27 lists the components of the SAK kit based on developed protocols.

DETAILED DESCRIPTION OF THE INVENTION

Figure 1:
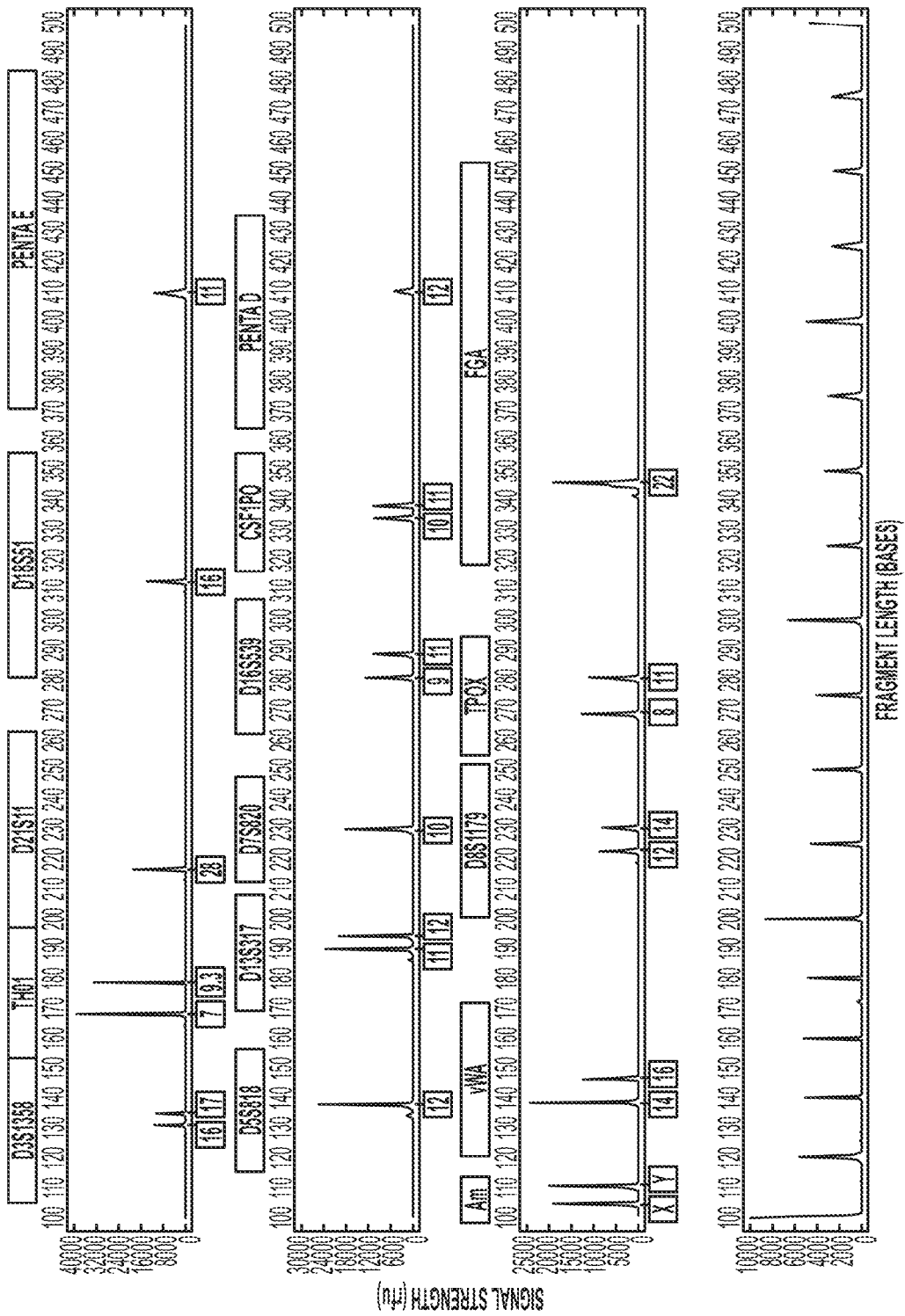
FIG. 1 shows a full 16-locus STR profile of nucleic acid purified from 200 mg freeze-milled bone powder of fresh femur sample. Sample was demineralized for 1 minute and analyzed in an A-Chip.
Figure 2:
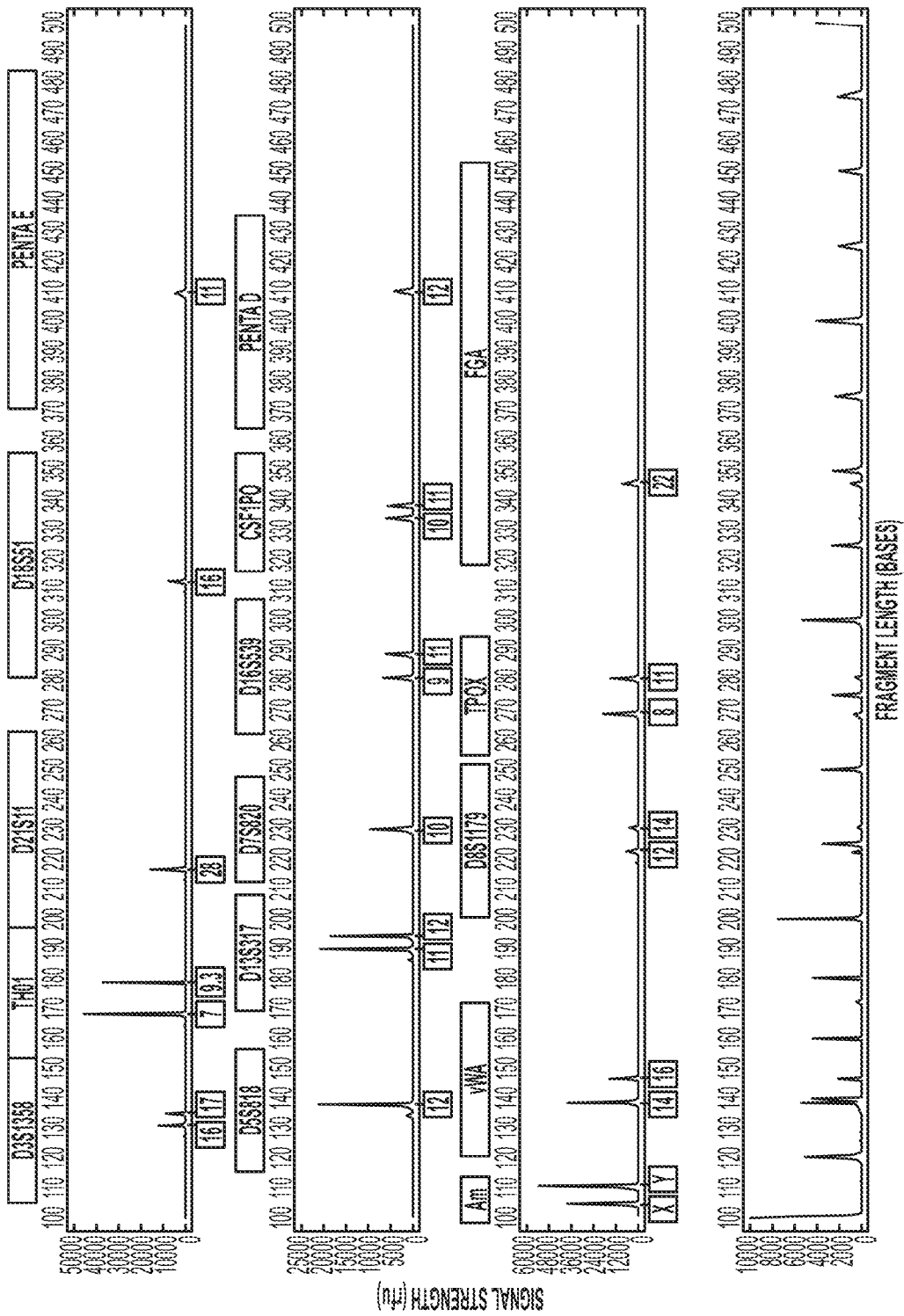
FIG. 2 shows a full 16-locus STR profile of nucleic acid purified from 10 mg freeze-milled bone powder of fresh femur sample. Sample was demineralized for 1 minute and analyzed in an I-Chip.
Figure 3:
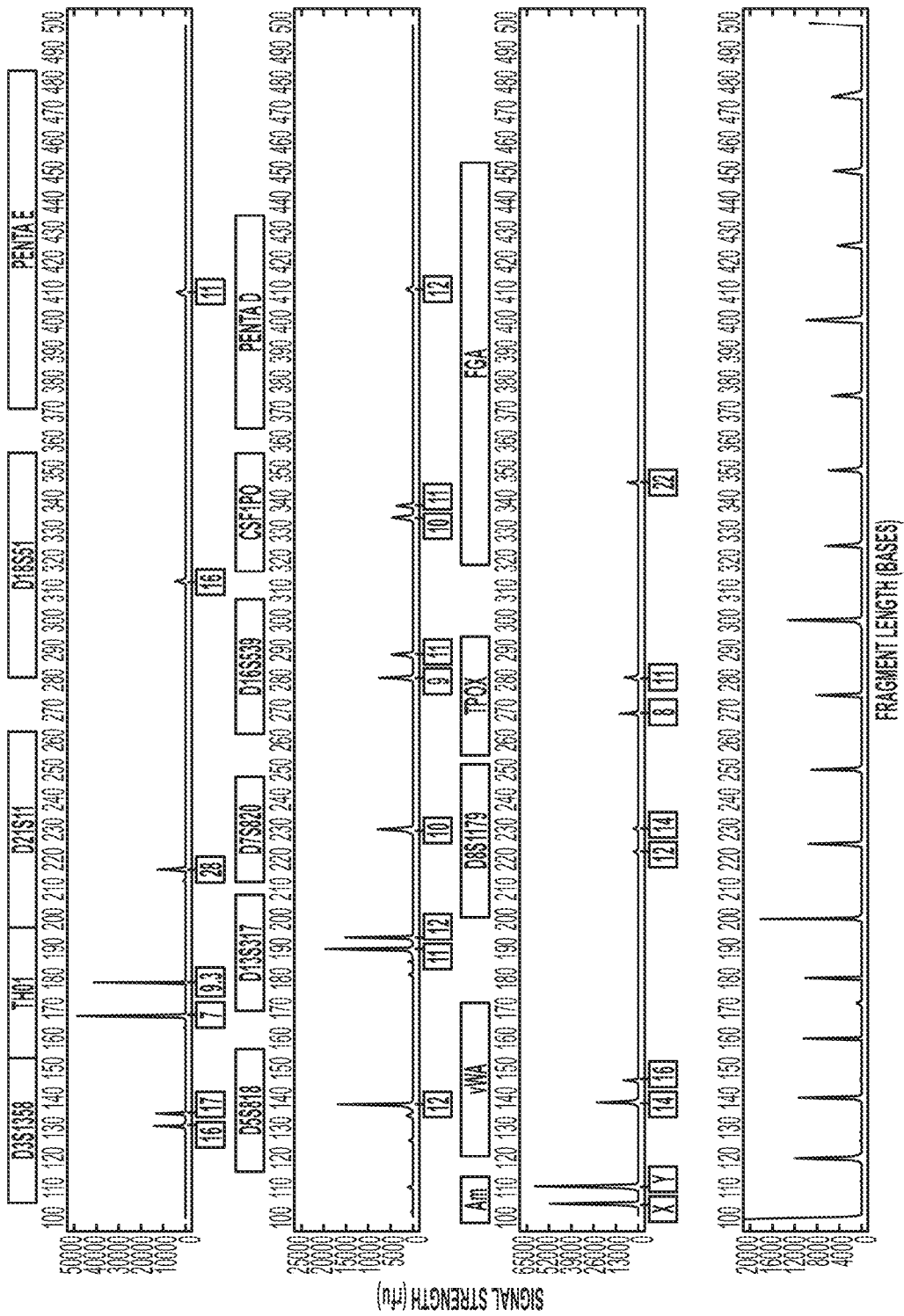
FIG. 3 shows a full 16-locus STR profile of nucleic acid purified from 500 mg freeze-milled bone powder of an artificially aged femur sample. Bone was soaked for 4 days in saltwater at 84° F., cleaned and dried, demineralized for 1 minute, and analyzed in an I-Chip.
Figure 4:
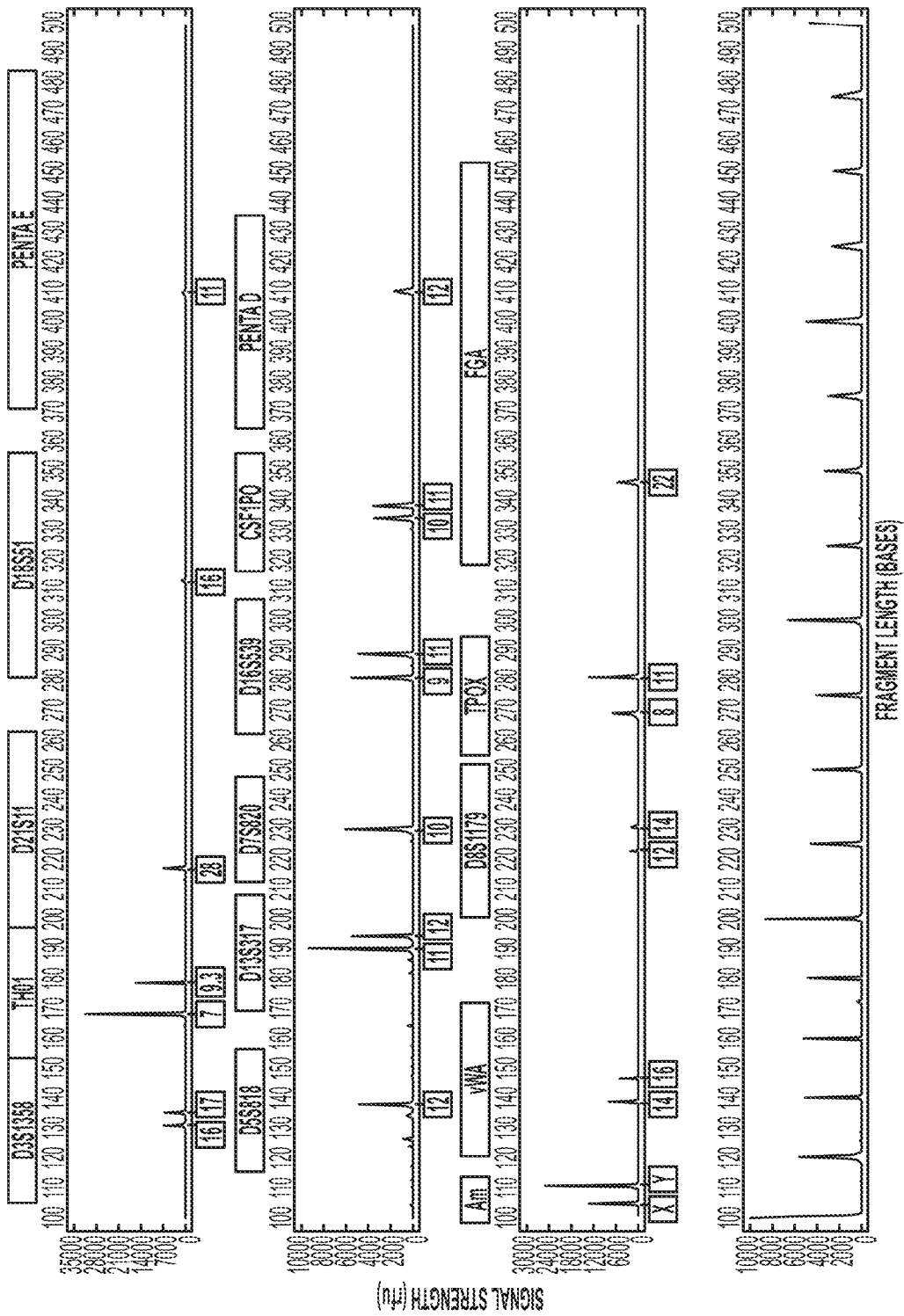
FIG. 4 shows a full 16-locus STR profile of nucleic acid purified from 200 mg freeze-milled bone powder of an artificially aged femur sample. Bone was soaked for 4 days in saltwater at 84° F., cleaned and dried, demineralized for 1 minute, and analyzed in an I-Chip.
Figure 5:
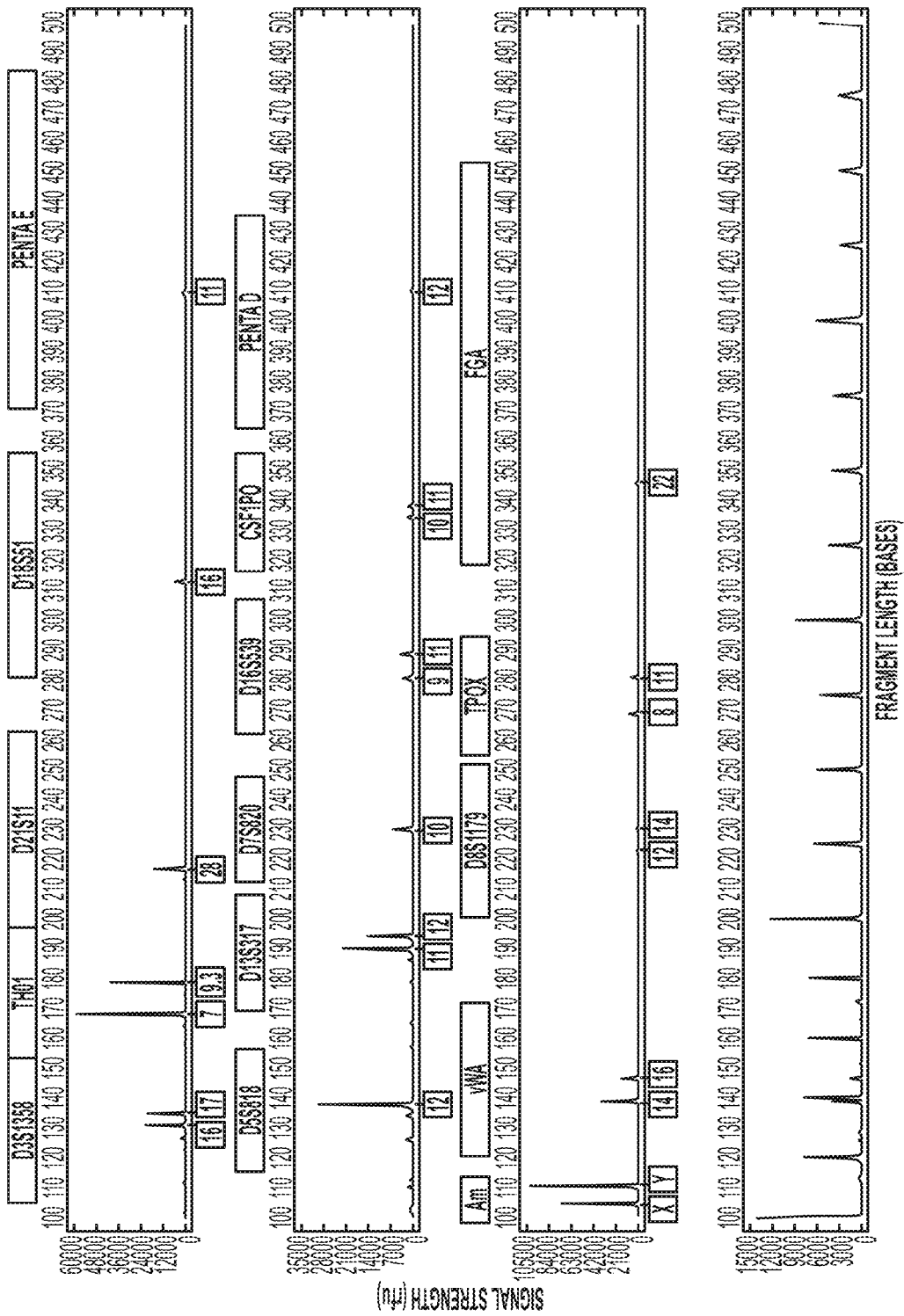
FIG. 5 shows a full 16-locus STR profile of nucleic acid purified from 500 mg hammered bone fragments of an artificially aged decomposed femur sample. Bone was soaked for 4 days in saltwater at 84° F., cleaned and dried, demineralized for 1 minute, and analyzed in an I-Chip.
Figure 6:
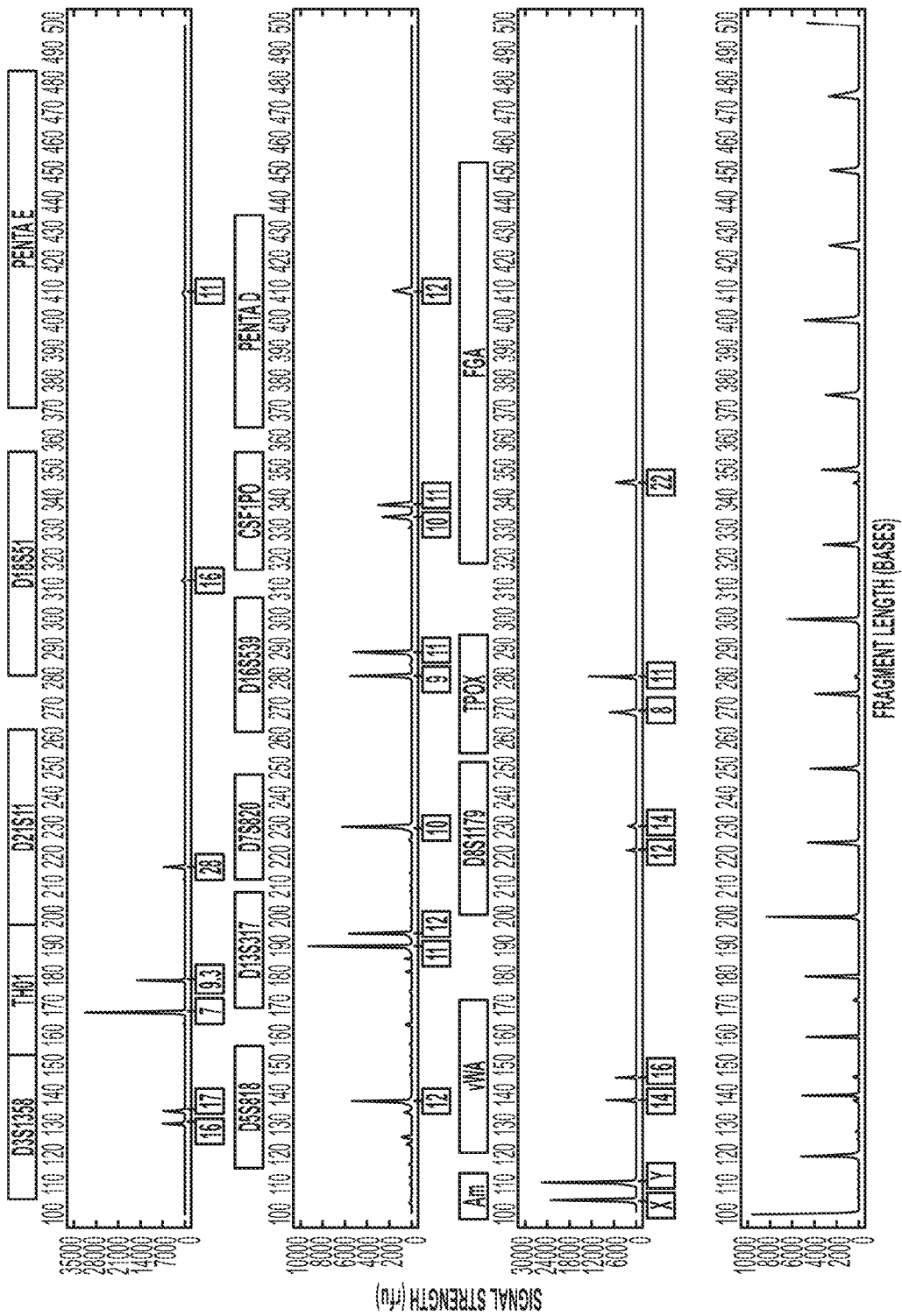
FIG. 6 shows a full 16-locus STR profile of nucleic acid purified from 200 mg hammered bone fragments of an artificially aged decomposed femur sample. Bone was soaked for 4 days in saltwater at 84° F., cleaned and dried, demineralized for 1 minute, and analyzed in an I-Chip.
Figure 7:
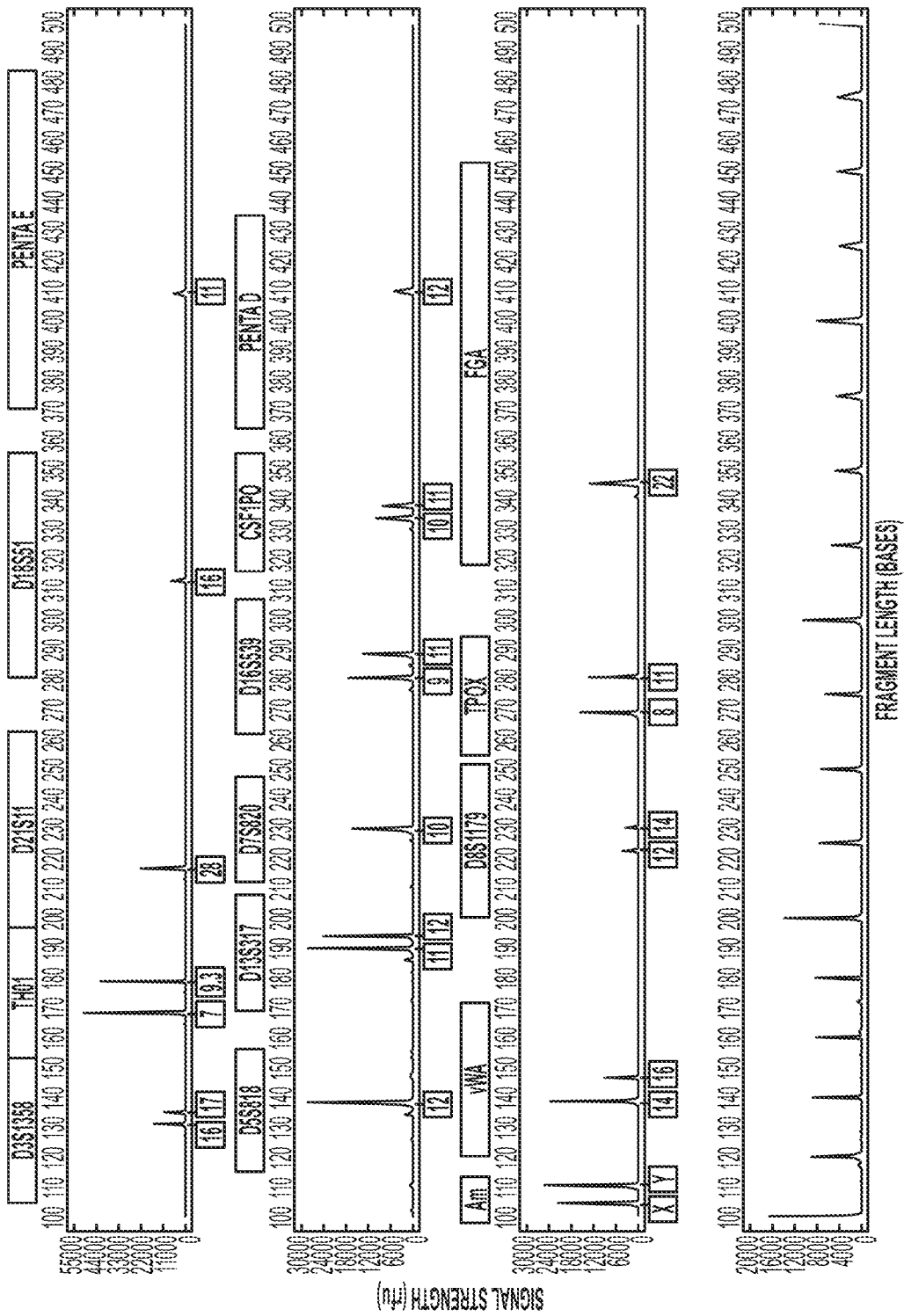
FIG. 7 shows a full 16-locus STR profile of nucleic acid purified from 500 mg freeze-milled bone powder of an artificially aged femur sample using the nucleic acid extraction method as reported by Loreille et al. Forensic Science International: Genetics 1 (2007) 191-195. Bone was soaked for 4 days in saltwater at 84° F., cleaned and dried, and analyzed in an I-Chip.

The inventors have discovered simpler and faster processes for extracting and purifying nucleic acids from a nucleic acid-containing material, particularly from bone, tooth, and semen (including vaginal swabs from Sexual Assault Kits). For bone and tooth, simple fragments generated by a hammer are suitable for processing, and bone/tooth powder is unnecessary. In one aspect, the invention is directed to a simplified and fast process for extracting nucleic acids from a nucleic acid-containing material. In another aspect, the invention is kits for performing the simplified and rapid processes for extracting nucleic acids from a nucleic acid-containing material. In yet another aspect, the invention is an integrated process for rapid nucleic acid analysis, e.g., Rapid DNA Identification based on STR profiling, where the sample processing, DNA extraction, purification, amplification, separation, detection, and analysis occur in a fast, efficient, and fully-integrated manner.

The inventions herein described are further explained and enabled, and may be used alone or in combination with other nucleic acid sequencing and sizing instruments, biochips and methods, co-owned with this application as set forth in the following patents, each of which is incorporated by reference in its entirety herein: U.S. Pat. Nos. 9,889,449 and 9,366,631 entitled "Integrated systems for the multiplexed amplification and detection of six and greater dye labeled fragments; U.S. Pat. Nos. 9,797,841 and 9,310,304 entitled "Methods and Compositions for Rapid multiplex amplification of STR loci," U.S. Pat. Nos. 9,606,083; 9,523,656; 8,206,974; 8,173,417 entitled "Ruggedized Apparatus for Analysis of Nucleic Acid and Proteins"; U.S. Pat. No. 9,550,985 entitled "Methods for Forensic DNA Quantitation"; U.S. Pat. Nos. 9,494,519 and 8,425,861 entitled "Methods for Rapid Multiplexed Amplification of Target Nucleic Acids"; U.S. Pat. No. 8,018,593 entitled "Integrated Nucleic Acid Analysis"; U.S. Pat. Nos. 9,354,199; 9,314,795; 8,720,036 entitled "Unitary Biochip Providing Sample-In to Results-Out Processing and Methods of Manufacture"; U.S. Pat. Nos. 9,174,210 and 9,012,208 entitled "Nucleic Acid Purification"; U.S. Pat. Nos. 8,961,765 and 8,858,770 entitled "Plastic Microfluidic Separation and Detection Platforms".

Processes for Nucleic Acid Extraction from Bone and Tooth

In one aspect, the invention is a simplified and fast process for extracting nucleic acids from a bone or tooth, and the process comprises the steps of providing the nucleic-acid containing material sample in a form suitable for nucleic acid extraction, mixing vigorously the sample in a demineralization buffer, e.g., 0.5 M EDTA, and separating the mixture to obtain a liquid portion of the mixture which contains the extracted nucleic acids.

In some embodiments, bone and tooth samples may be fresh samples from donors with post-mortem interval (PMI) less than 8 hours or relatively fresh samples from donors with post-mortem interval (PMI) of 2-6 days. In other embodiments, bone and tooth may be from casework, disaster, missing persons or related samples. Such samples may be obtained as degraded as is the case, for example, decayed bodies in fresh water, salt water, or soil or after a fire or explosion. Bone and tooth samples may be years, decades, or centuries old, often exposed to the elements. In mass disasters, missing persons cases, terrorist and criminal incidents, and atrocities committed by dictatorial regimes, this ability to generate STR profiles from such aged bone is critical.

In some embodiments, the samples are first cleaned and then grinded so that the samples are in a form suitable for nucleic acid extraction. For example, the samples may be washed with water and scrubbed to remove debris, soaked in 10% bleach solution, and washed again with sterile water before a final wash with 70% ethanol. After the final wash with ethanol, the samples may be dried at room temperature and grinded, for example, by freeze-mill to make powderized samples or hammering to make fragmented or granulated samples. Although not absolutely required, cleaning is advantageous in that it may remove large quantities of microbial contaminants and, just as importantly, human DNA introduced by human handling or mixtures from two or more sample donors (if cleaning is not utilized, potential mixed profiles may be deconvolved manually or using software). As will be discussed below, milling is not necessary, an important consideration when the work is to be performed outside the laboratory.

In some embodiments, the bone or tooth sample may be milled and powderized. By way of example, a piece of bone may be milled using many techniques, for example using the SPEX Sample Prep 6870 Large Freezer/Mill® (SPEX Sample Prep LLC, Metuchen, NJ) following a 3-cycle program, 10 minute pre-cool, 2 minute run time, 2 minute cool time, and with a rate of 10 cycles per second. Aged dried bone sample may be completely milled after this protocol, but a few smaller fragments may remain when using fresh bone. For fresh bone, the milled sample may be collected for further processing after the completion of milling cycle. Powderized bone or tooth samples may be transferred into sterile tube containers.

In other embodiments, the bone or tooth sample may be hammered and fragmented. Crude breakage of the bone or tooth may also be effective. For example, a piece of bone or tooth may be wrapped in a DurX®770 (Berkshire Corporation, Great Barrington, MA) wipe (a non-woven sheet of polyester/cellulose material) or equivalent. Using a clean hammer or a similar hard, blunt object, e.g. a rock (washed and wiped down with an ethanol wipe if available), the bone or tooth may be stroked several times until the sample piece is broken into smaller pieces. Hitting the bone or tooth sample at different angles with the hammer may facilitate the breakdown of the sample into smaller fragments. When hammering bone, small marrow pieces may be collected immediately. The harder bone bits (those refractory to initial hammering) can be hammered again into smaller pieces by wrapping the bone pieces with a new DurX®770 wipe and striking a few more times. The ideal size of bone fragments for processing is preferably about ⅛ inch or less. In general, the effect of milling or hammering is to generate small fragments and increase the exposed surface area of the bone accessible to further processing (thereby enhancing subsequent extraction and purification steps).

The ground or hammered bone or tooth samples may be mixed vigorously in a demineralization buffer to demineralize the bone matrix and consequently, release DNA. In some embodiments, a demineralization buffer can be simply an EDTA solution with an EDTA concentration of 0.1 M to 1 M, preferably 0.3-0.7 M, more preferably 0.5 M, without any other chemicals. In other embodiments, the demineralization buffer, e.g., 0.5 M EDTA, may further comprise a lysis buffer, DTT (0.02 M) and proteinase K. In still other embodiments, the demineralization buffer, e.g., 0.5 M EDTA, may further comprise a detergent, e.g., 0.5% SDS or 1% lauryl sarcosinate or equivalent, or proteinase K (3-4 mg), or both.

Figure 20:
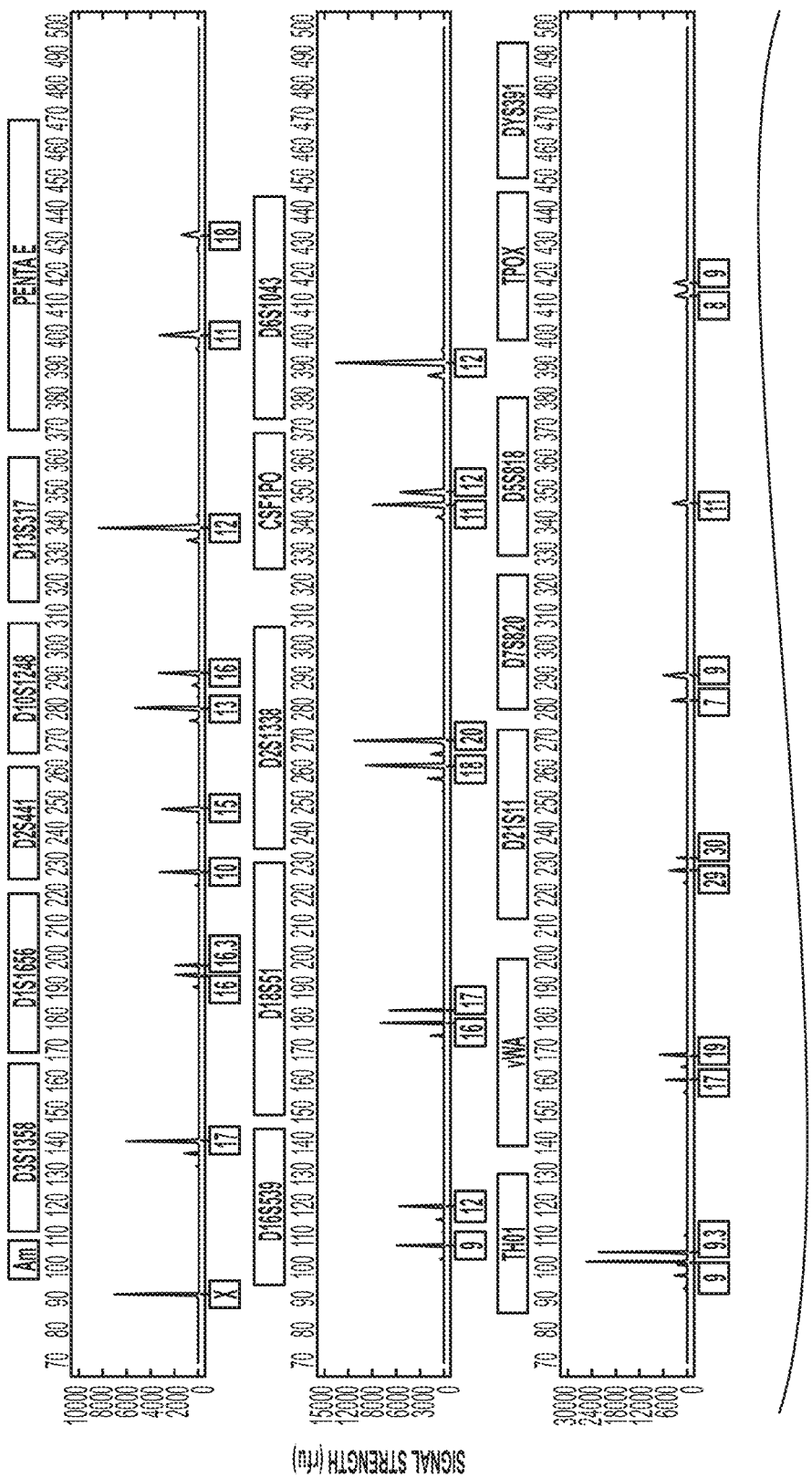
FIG. 20 shows a full 27-locus STR profile of nucleic acid purified from 10 mg hammered root fragments of fresh incisor tooth sample. Sample was demineralized for 10 minutes and analyzed in an I-Chip.
Figure 20:
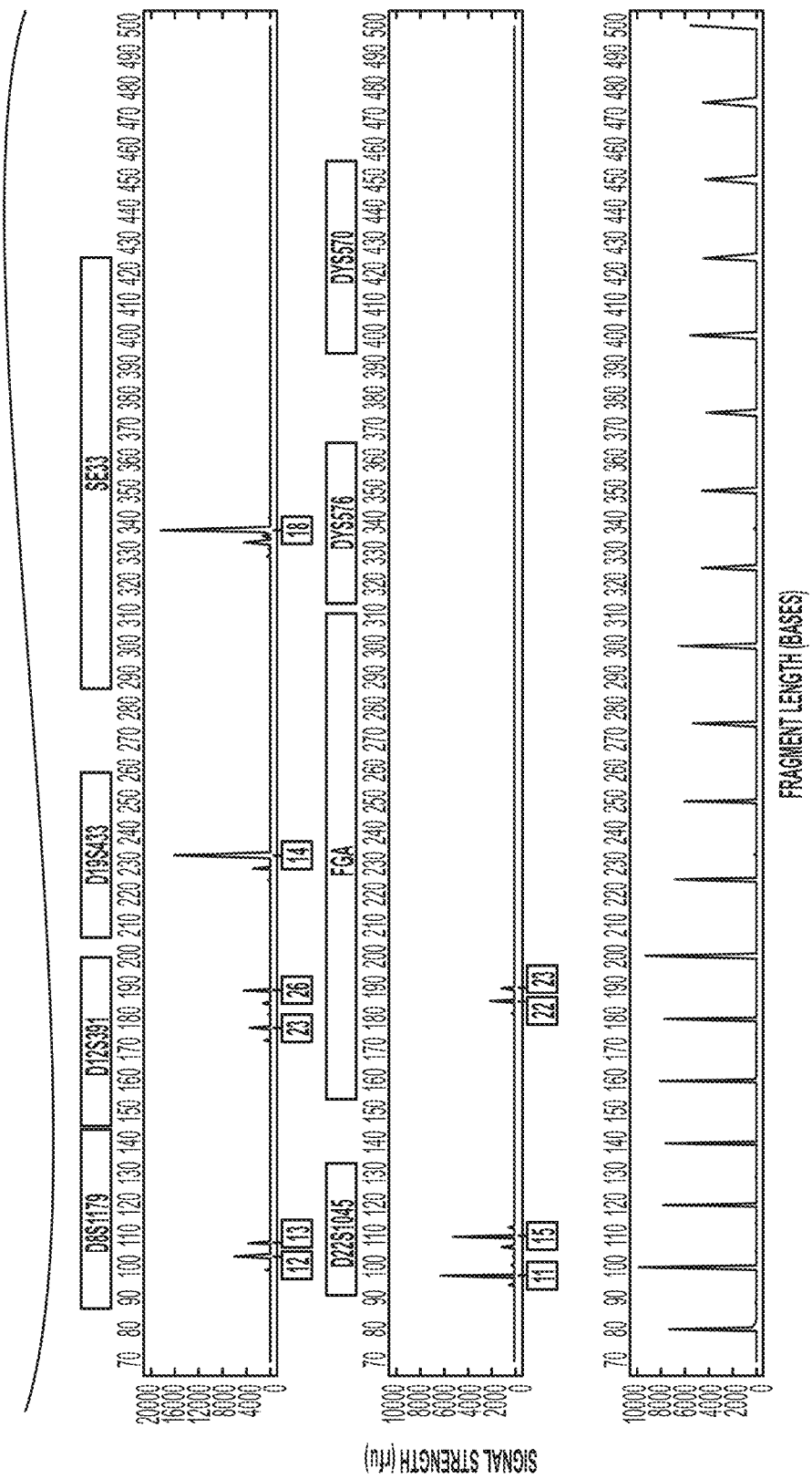
Figure 21:
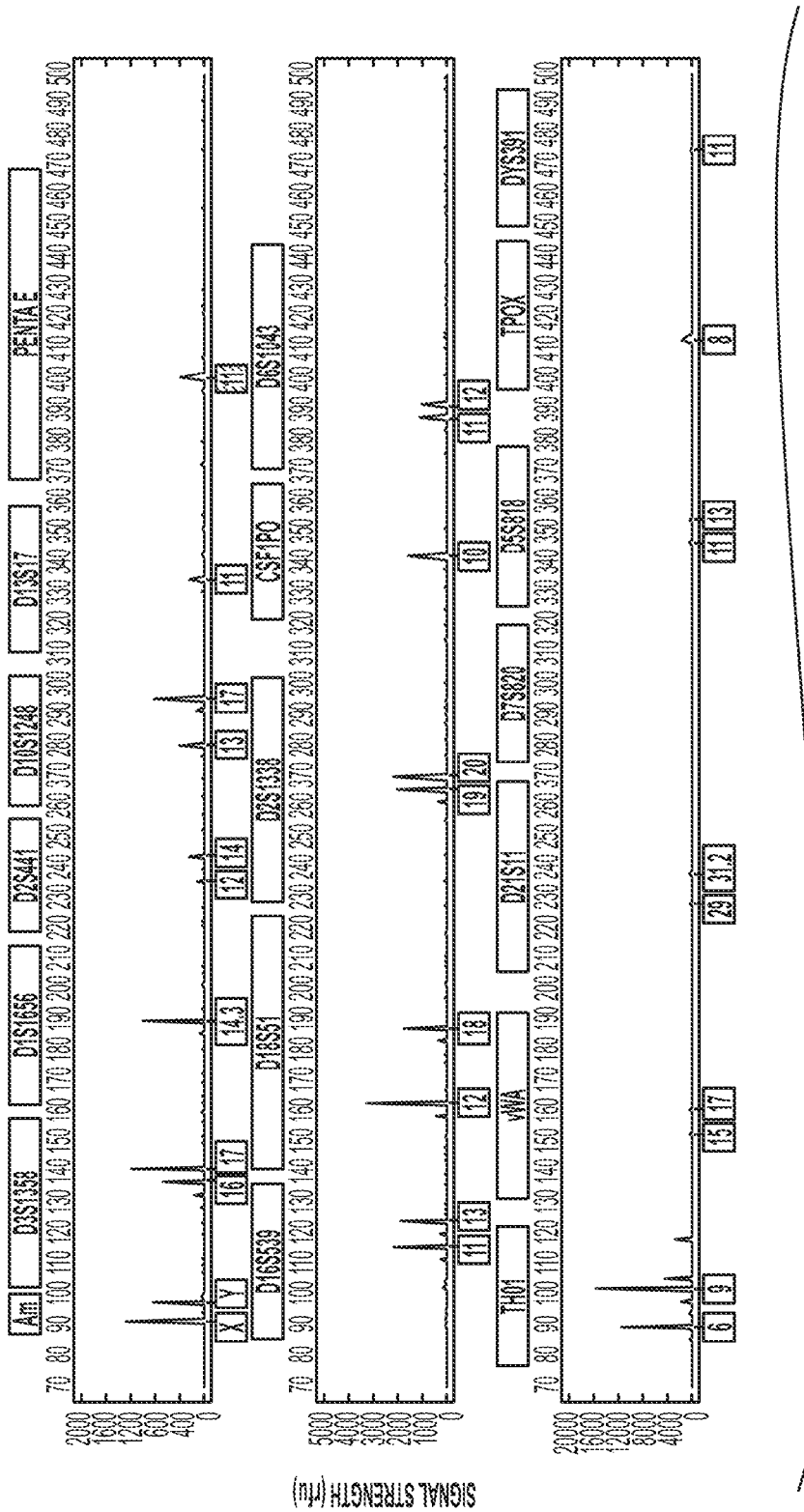
FIG. 21 shows a partial STR profile (24 of 27 loci) of nucleic acid purified from 200 mg hammered root fragments of aged molar tooth sample. Tooth was extracted from human body placed 120 days above field ground, cleaned and dried prior to separating the root from crown, demineralized for 180 minutes, and analyzed in I-Chip.
Figure 21:
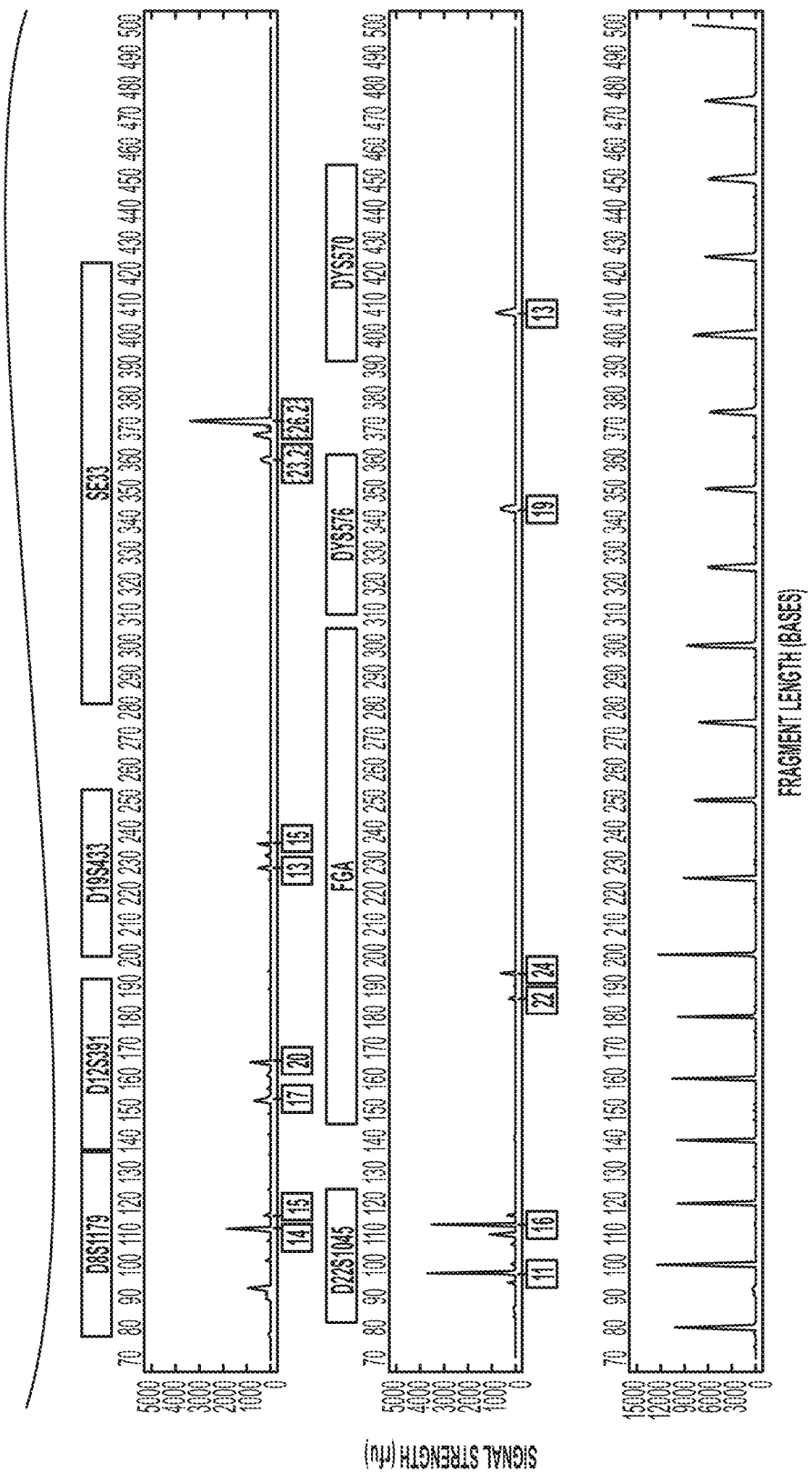

The volume of a demineralization buffer added to samples may vary depending on the amount of the sample to be processed, its size, and texture (hammered bone tends to absorb less than milled bone; aged dried bone tends to absorb more than fresher, red marrow-containing samples). FIG. 20 shows the average amount of purified DNA (in nanograms) as a function of the volume of demineralization buffer added to a 500 mg bone powder sample. The data was from quadruplicate measurements, with error bars representing 1 standard deviation. This data demonstrates that sufficient demineralization can be achieved with far less buffer than used by prior art methods. For <10 mg milled or hammered bone, 120 µl of buffer is sufficient. For 200 mg bone, 200-2200 of buffer is sufficient. For 500 mg bone, 320-3500 buffer is sufficient. Prior art methods were based on the incorrect assumption that complete dissolution of bone was required to allow DNA trapped in cells and bound to hydroxyapetite to be freed forensic samples and available for STR processing. We demonstrate herein that this is not the case and that partially demineralized bone using a simple demineralization solution enables generation of excellent STR profiles. FIG. 21 shows a demineralization time-course. DNA yield/200 mg bone powder (in nanograms) is plotted on the y-axis as a function of time on the x-axis. The data shows that overnight demineralization is not needed to obtain sufficient DNA for STR analysis. The data in the figure was from 6 measurements, with error bars representing one standard deviation.

The invention may be designed to eliminate a long process of sample concentration without compromising pretreatment efficiency and to maximize the volume of liquid to be analyzed by conventional laboratory or Rapid DNA analysis methodologies. In some embodiments, 300-350 µl of a demineralization buffer, e.g., 0.5 M EDTA, may be used for every 500 mg of bone or tooth; 150-220 µl of a demineralization buffer, e.g., 0.5 M EDTA, may be used for every 100-200 mg of bone or tooth, and 100-150 µl of a demineralization buffer, e.g., 0.5 M EDTA, for less than 100 mg bone or tooth.

Figure 22:
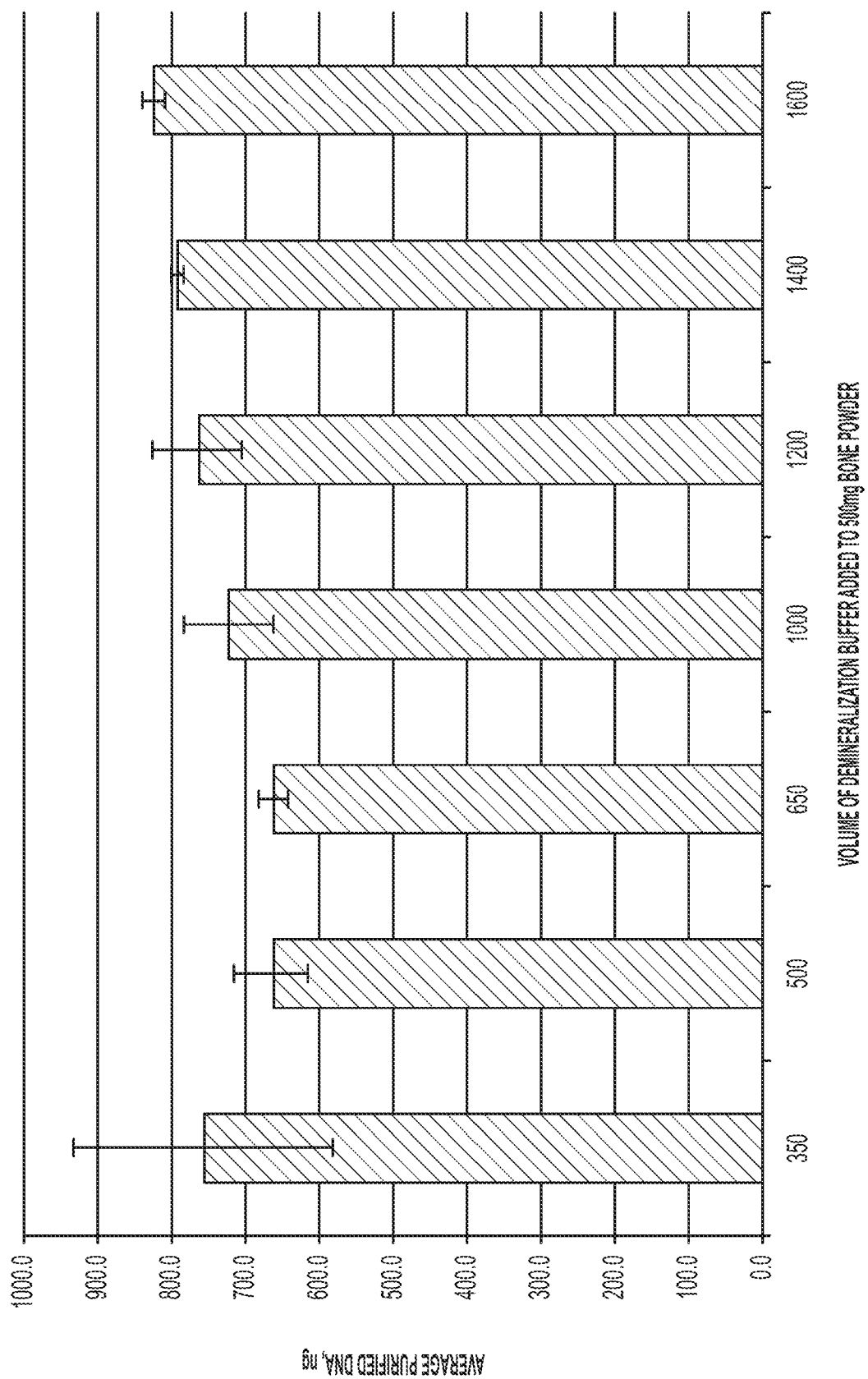
FIG. 22 is a plot showing the average amount of purified DNA (in nanograms) as a function of the volume of demineralization buffer (in microliters) added to a 500 mg bone powder sample. Data was taken from quadruplicate measurements, with error bars representing 1STDEV. This data led us to believe that we can use less buffer for less bone (or tooth) as starting material.

This invention may be practiced with several demineralization buffers, including without limitation, 1% sarcosine, 0.002% SDS, 0.5% SDS and others, with 0.5 M EDTA being preferred. Prior art methods suggest that 0.5% EDTA requires the use of detergents and proteinase K to obtain sufficient demineralization of bone to be useful in STR analysis. FIG. 22 demonstrates that this is not the case. FIG. 22 demonstrates that simplified demineralization buffers of this invention result in sufficient amounts of purified DNA for use in STR analysis.

The amount of the milled or hammered sample may be 1 mg-1 g, and preferably 200-500 mg for aged/degraded samples with an I-Chip. For fresh or intact bone samples in I-Chips, Chips, approximately 5-10 mg samples may be sufficient to obtain nucleic acids resulting in full STR profiles and less than 5 mg may generate full or useful partial STR profiles. The actual DNA content of the sample affects the result. Nevertheless, a degraded bone sample with no intact DNA will not generate a profile regardless of how much sample is utilized. A full STR profile or a useful partial profile of a person means that the profile is sufficient to identify the person's identity and match when submitted to a database or utilized in a kinship algorithm. We report herein STR profiles generated using 16-locus and 27-locus assays, the latter showing superior sensitivity. With standard analytical scales, it is impossible to measure minute samples, so one can adjust buffer volume to load onto swab for analysis without signal saturation. The sample input in the 27-locus STR profiles is theoretically equivalent to 0.6 mg sample.

Depending on the amount of genomic material expected to be present in the sample (high or low), one may select the type of rapid DNA chip that is best suited for processing. In the ANDE system, A-Chips are utilized if it is estimated that 100's of ngs or more are present in a sample whereas I-Chips are utilized if it is estimated that less than 100's of ngs of DNA are present. It follows that for hammered bone and teeth, for example, I-Chips would typically be utilized for processing in the ANDE Rapid DNA system. The identical selection process can be utilized in other rapid DNA systems. In the event that too much or too little sample is utilized (which can be determined by reviewing signal strength—peak heights—on the resulting electropherogram, repeat rapid DNA runs utilizing more or less starting material can be run. In addition, an Adaptive Expert System can be utilized to expand the dynamic range of the rapid DNA Identification system.

The quantity of DNA present in bone may be affected by several factors including time of collection (fresh versus decomposed remains), with and without red marrow, the type of bone from the body, and the age and health of donor. Nevertheless, the selection of chip type may be straightforward: relatively fresh bone may likely be processed effectively in the high DNA content chip, and older bone may likely be processed effectively in the high DNA content chip.

The simple and rapid demineralization may be facilitated by vortexing the mixture, for example, for 30 seconds to 1 minute on a benchtop vortex mixer (Vortex-Genie 2, Scientific Industries Model #G560) set at max setting (scale 10). This demineralization step in the presence of EDTA increases nucleic acid purification efficiency. In some embodiments, e.g., outside the laboratory, this vortexing may be replaced with vigorous shaking by hand for at least 1 min and tapping the tube several times to homogenize the contents.

In some embodiments, the liquid sample or the demineralized sample solution may be allowed to settle until a supernatant forms under the influence of gravity. In other embodiments, the settlement may be facilitated by spinning the tube by hand. In still other embodiments, the liquid sample or the demineralized sample solution may be obtained from the mixture, for example, by centrifugation. The centrifugation may be for 2 minutes at 20,000×g. The supernatant (in the case of milled samples) or sample liquid (in the case of hammered samples) contains the extracted nucleic acids.

In some embodiments, the supernatant containing the extracted nucleic acids may be used directly for further analysis without purification in a rapid DNA analysis system. In other embodiments, nucleic acids in the supernatant may be further purified before being used for further analysis.

Purification of nucleic acids from supernatant may be accomplished by various methods known in the art, for example, organic extraction using phenol/chloroform/isoamyl alcohol (25:24:1), or silica purification using filters such as those from MagAttract® (Quiagen, N.V., Venlo, NL) DNA mini M48 kit.

In one embodiment, a small portion of the supernatant may be directly transferred onto a transfer medium (e.g., a swab, pipette or filter paper or the like), which may then be inserted into a rapid DNA analysis system for nucleic acid analysis. The portion of the supernatant may be about 100-150 $\mu$. This invention may be practiced with a rapid DNA analysis system capable of processing small portions or the supernatant, for example the ANDE™ system available from ANDE, Corporation, Waltham, MA). See e.g., Tan et al., Investig Genet. 2013; 4: 16 and Turingan et al., Investig Genet. 2016; 7:2 and Grover et al., Int J Legal Med (2017) 131:1489-1501 which are herein incorporated by reference in entirety.

Kit for Nucleic Acid Extraction

In another aspect, the invention is a kit for performing the simplified and fast process for extracting nucleic acids from a nucleic acid-containing material, e.g., bone or tooth.

In one embodiment, the kit for extracting nucleic acids from bone and tooth comprises a buffer for demineralizing bone matrix and optionally a brochure detailing a rapid nucleic acid extraction process. In another embodiment, the demineralization buffer may contain only 0.5 M EDTA. In some embodiments, 0.5 M EDTA may be combined with lysis buffer DTT (0.02 M), and proteinase K. In other embodiments, 0.5 M EDTA may be combined with detergent (0.5% SDS or 1% lauryl sarcosinate or equivalent) and proteinase K (3-4 mg).

In some embodiments, the brochure may include an instruction of how to perform nucleic acid extraction using the lysis buffer from bone and tooth samples. In some instances, the brochure may further describe how to pre-treat the bone and tooth samples. In still some instances, the brochure may further describe how to analyze the extracted nucleic acids, for example, using a swab for analyzing the extracted nucleic acids in HDC BCS and/or LDC BCS system. In still some further instances, the brochure may describe the process for nucleic acid extraction supra in the present application.

In other embodiments, the kit may further include solutions for washing and cleaning the nucleic acid-containing material. In still other embodiments, the kit may further include a swab for analyzing the extracted nucleic acids in HDC and/or LDC BCS.

Processes for Determining STR Profiles of Nucleic Acids from a Bone or Tooth Sample In yet another aspect, the invention is a process for determining STR profiles of nucleic acids from a bone or tooth sample. In some embodiments, the process comprises providing the nucleic acid-containing material in a form suitable for nucleic acid extraction; adding EDTA to demineralize the nucleic acid-containing material to obtain a mixture; mixing the mixture vigorously; separating the mixture to obtain a liquid sample that contains the extracted nucleic acids; subjecting a portion, if not all, of the liquid supernatant for fully integrated nucleic acid purification and generation of an STR profile.

In some embodiments, bone and tooth samples may be fresh samples from donors with post-mortem interval (PMI) less than 8 hours or relatively fresh samples from donors with PMI of 2-6 days. In other embodiments, bone and tooth may be from casework, disaster, missing persons or related samples. Such samples may be obtained as degraded as is the case, for example, decayed bodies in fresh water, salt water, or soil or after a fire or explosion.

In some embodiments, the samples are first cleaned and then grinded so that the samples are in a form suitable for nucleic acid extraction. For example, the samples may be washed with water and scrubbed to remove debris, soaked in 10% bleach solution, and washed again with sterile water before a final wash with 70% ethanol. After the final wash with ethanol, the samples may be dried at room temperature and grinded, for example, by freeze-mill to make powderized samples or hammering to make fragmented or granulated samples. Although not absolutely required, cleaning is advantageous in that it may remove large quantities of microbial contaminants and, just as importantly, human DNA introduced by human handling or mixtures from two or more sample donors. Milling may be also advantageous, but not necessary, consideration when the work is to be performed outside the laboratory.

In some embodiments, the bone or tooth sample may be milled and powderized. By way of example, a piece of bone may be milled using many techniques, for example using the SPEX Sample Prep 6870 Large Freezer/Mill® following a 3-cycle program, 10 minute pre-cool, 2 minute run time, 2 minute cool time, and with a rate of 10 cycles per second. Aged dried bone sample may be completely milled after this protocol, but a few smaller fragments may remain when using fresh bone. For fresh bone, the available milled sample may be collected for further processing after the completion of milling cycle. Powderized bone or tooth samples may be transferred into sterile tube containers.

In other embodiments, the bone or tooth sample may be hammered and fragmented. Crude breakage of the bone or tooth may also be effective. For example, a piece of bone or tooth may be wrapped in a DurX®770 wipe (a non-woven sheet of polyester/cellulose material) or equivalent. Using a clean hammer or a similar hard, blunt object, e.g. a rock (washed and wiped down with an ethanol wipe if available), the bone or tooth may be stroked several times until the sample piece is broken into smaller pieces. Hitting the bone or tooth sample at different angles with the hammer may facilitate the breakdown of the sample into smaller fragments. When hammering bone, small marrow pieces may be collected immediately. The harder bone bits (those refractory to initial hammering) can be hammered again into smaller pieces by wrapping the bone pieces with a new DurX®770 wipe and striking a few more times. The ideal size of bone fragments for processing is preferably about ⅛ inch or less. In general, the effect of milling or hammering is to generate small fragments and increase the exposed surface area of the bone accessible to further processing (thereby enhancing subsequent extraction and purification steps).

The ground or hammered bone samples must be mixed vigorously in 0.5 M EDTA to demineralize the bone matrix. In some embodiment, 0.5 M EDTA may be combined with lysis buffer and DTT (0.02 M), and proteinase K (10 mg). In other embodiments, 0.5 M EDTA may be combined with detergent (0.5% SDS or 1% lauryl sarcosinate or equivalent) and proteinase K (3-4 mg).

The volume of demineralization buffer added to samples may vary depending on the amount of the sample to be processed, its size, and texture (hammered bone tends to absorb less than milled bone; aged dried bone tends to absorb more than fresher, red marrow-containing samples). The invention may be designed to eliminate a long process of sample concentration without compromising pre-treatment efficiency and to maximize the volume of liquid to be loaded onto the swab for analysis without over saturation. In some embodiments, 300-350 µl of 0.5 M EDTA may be used for every 500 mg of bone or tooth; 150-220 µl of 0.5 M EDTA may be used for every 100-200 mg of bone or tooth, and 100-150 W of 0.5 M EDTA for less than 100 mg bone or tooth. Tooth samples may require longer incubation than bone. In most cases, full STR profiles may be generated from bone with 1 min incubation while full STR profiles from tooth with 10 min incubation.

The amount of the milled or hammered sample can be 1 mg-1 g or more, and preferably 200-500 mg for aged/degraded samples in I-Chip. For fresher/intact bone samples in I-Chip, approximately 5-10 mg samples may be sufficient to obtain nucleic acids resulting in full STR profiles and less than 5 mg may generate full or useful partial profiles. The actual DNA content of the sample will determine the result. Nevertheless, a degraded bone sample with no intact DNA will not generate a profile regardless of how much sample is utilized. A full STR profile or a useful partial profile of a person means that the profile is sufficient to identify the person's identity and match when submitted to a database or utilized in a kinship algorithm.

Depending on the amount of genomic material expected to be present in the sample (high or low), one may select the type of chip, A-Chip or I-Chip, that is better suited for processing. The quantity of DNA present in bone may be affected by several factors including time of collection (fresh versus decomposed remains), with and without red marrow, the type of bone from the body, and the age and health of donor. Nevertheless, the selection of chip type may be straightforward: relatively fresh bone may likely be processed effectively in the high DNA content chip/A-Chip, and older bone may likely be processed effectively in the low DNA content chip/I-Chip.

The simple and rapid demineralization may be facilitated by vortexing the mixture, for example, for 30 seconds to 1 minute on a benchtop vortexer set at max setting (scale 10). This demineralization step in the presence of EDTA may help increase nucleic acid yield because decrease in nucleic acid yield is observed without treatment with EDTA. In some embodiments, e.g., outside the laboratory, this vortexing may be replaced with vigorous shaking by hand for at least 1 min and tapping the tube several times to homogenize the contents.

In some embodiments, the liquid sample or the demineralized sample solution may be allowed to settle until a supernatant forms under the laws of gravity. In other embodiments, the settlement may be facilitated by spinning the tube by hand. In still other embodiments, the liquid sample or the demineralized sample solution may be obtained from the mixture, for example, by centrifugation. The centrifugation may be for 2 minutes at 20,000×g. The supernatant (in the case of milled samples) or sample liquid (in the case of hammered samples) contains the extracted nucleic acids.

In some embodiments, the supernatant containing the extracted nucleic acids may be used directly for further analysis without purification. In other embodiments, nucleic acids in the supernatant may be further purified before being used for further analysis.

Purification of nucleic acids from supernatant may be accomplished by various methods known in the art, for example, organic extraction using phenol/chloroform/isoamyl alcohol (25:24:1), or silica purification using filters such as those from Qiagen MagAttract® DNA mini M48 kit.

Kit for Determining STR profiles of Nucleic Acids from a Bone or Tooth Sample In yet another aspect, the invention is a kit for determining STR profiles of nucleic acids from a bone or tooth sample. In some embodiments, the kit may include a 0.5 M EDTA as demineralization buffer; a brochure detailing a rapid nucleic acid extraction process; and a swab for analyzing the extracted nucleic acids in LDC BCS.

In some embodiments, the kit may further include solutions for washing and cleaning the bone or tooth sample to remove adhered tissue debris on surface, dirt, and exogenous DNA using water, followed by 10% bleach solution, then rinsing again with water, and finally with 70% ethanol.

In some embodiments, the kit is for profiling the STR multiplexes which include the following loci: D3S1358, TH01, D21S11, D18S51, Penta E, D5S818, D13S17, D7S820, D16D539, CSF1PO, Penta D, Amelogenin, vWA, D8S1179, TPOX, and FGA (the Powerplex 16 chemistry). In other embodiments, the kit is for profiling STR multiplexes including the following loci: D3S1358, D19S433, D2S1338, D22S1045, Penta B, TH01, D18S51, D1S1656, D10S1248, D2S441, Penta C, D16S539, vWA, D21S11, D12S391, Amelogenin, Penta D, D5S818, D13S317, D7S820, TPOX, CSF1PO, Penta E, D8S1179, FGA, SE33, DYS391, D6S1043, DYS439, DYS389II, DYS19, DYS392, DYS393, DYS389I, DYS390, DYS385a, DYS385b, DYS437, and DYS438. In still other embodiments, STR multiplexes will include the following loci: 23 autosomal loci (D1S1656, D2S1338, D2S441, D3S1358, D5S81, D6S1043, D7S820, D8S1179, D10S1248, D12S391, D13S317, D16S539, D18S51, D19S433, D21S11, D22S1045, FGA, CSF1PO, Penta E, TH01, vWA, TPOX, SE33), three Y-chromosomal loci (DYS391, DYS576, and DYS570), and Amelogenin. For all sample types discussed herein, there is no limit to the sets of STR multiplexes utilized for the generation of DNA IDs. Typically, at least 7 STR loci should be used in the generation of DNA IDs because the Random Match Probability with this number is sufficiently low (one in tens of thousands to one in millions) to allow positive DNA identifications. The specific STR multiplexed utilized is based on the application (e.g. search of a very large DNA database [ten million or more samples as in the US, UK, and Chinese databases] to match a DNA from a potential rapist]; or search of a relatively small database [hundreds to thousands of samples for disaster victim identification in a plane crash]).

Processes for Simplified and Fast Semen DNA Analysis

In another aspect, the invention is a process for analyzing nucleic acids from a semen sample. A semen sample may be neat semen or a semen stain on a fabric. Alternatively, a semen sample may be directly or indirectly collected from an individual. In some instances, the semen sample may be a forensic semen sample, e.g., a casework semen sample. Even though the form of a semen sample may vary, the present invention is equally applicable as long as the semen sample may be collected onto a swab head.

In some embodiments, the process for determining STR profiles of nucleic acids from a semen sample comprises the steps of collecting the semen sample onto a swab, applying an appropriate amount of a dithiothreitol (DTT) or Tris(2-carboxyethyl)phosphine hydrochloride (TCEP) solution onto the swab head; and inserting the swab into a rapid nucleic acid analysis system for STR analysis. The inventive processes herein may be used with any panel of STR loci. In some embodiments, the kit is for profiling the STR multiplexes which include the following loci: D3S1358, TH01, D21S11, D18S51, Penta E, D5S818, D13S17, D7S820, D16D539, CSF1PO, Penta D, Am, vWA, D8S1179, TPOX, and FGA. In other embodiments, the kit is for profiling STR multiplexes including the following loci: D3S1358, D19S433, D2S1338, D22S1045, Penta B, TH01, D18S51, D1S1656, D10S1248, D2S441, Penta C, D16S539, vWFA31, D21S11, D12S391, Amelogenin, Penta D, D5S818, D13S317, D7S820, TPOX, CSF1PO, Penta E, D8S1179, FGA, SE33, DYS391, D6S1043, DYS439, DYS389II, DYS19, DYS392, DYS393, DYS389I, DYS390, DYS385a, DYS385b, DYS437, and DYS438. In still other embodiments, STR multiplexes will include the following loci: 23 autosomal loci (D1S1656, D2S1338, D2S441, D3S1358, D5S81, D6S1043, D7S820, D8S1179, D10S1248, D12S391, D13S317, D16S539, D18S51, D19S433, D21S11, D22S1045, FGA, CSF1PO, Penta E, TH01, vWA, TPOX, SE33), three Y-chromosomal loci (DYS391, DYS576, and DYS570), and Amelogenin.

In other embodiments, the semen sample may be neat semen or dried semen sample on a piece of fabric and the process comprises the steps of collecting the nucleic acid-containing material sample onto a swab, applying DTT or TCEP to the swab, and subjecting the swab into the ANDE system, for example the I-Chip, for analysis. In some instances, the semen sample may be dried semen stain on a fabric and the process may further comprise the step of scraping the semen sample from the fabric with a scraping tool, such as a knife, a razor blade or a scalpel. In some instances, the semen stain on the fabric may be wetted with sterile water and the swab rubbed and pressed against the fabric.

In some embodiments, the collection step may be carried out by scraping the fabric with a tool such as a knife, a razor blade or a scalpel. The collection step may be to collect the fabric fibers that the semen sample has been dried on. In a preferred embodiment, the semen samples are collected onto swabs. The swabs may be wetted with water before being used to collect semen samples. In some instances, the swab may be wetted with a few drops of molecular grade water from a water dropper, preferably 1-2 drops. In other instance, the swab may be wetted with more water due to the increased size of the swab head. In other instance, the stain on the fabric may be wetted with a few drops of molecular grade water from a water dropper, preferably 1-2 drops. The wetting of the swab head and the fabric stain may facilitate the collection of semen samples.

In some embodiments, the wetted swab may be used to swab the surface of the scraped fabric material. In other embodiments, the swab may be further used to collect the clumps of the fabric fiber that was previously scraped off the fabric material. It is preferred to secure the clumps of fabric fibers onto the swab head before further processing the swab.

In some embodiments, the swab head may be applied with 50 µl 150 mM DTT or 50 µl 50 mM TCEP. The presence of DTT or TCEP may facilitate the breakdown of disulfide bonds on sperm nuclear membranes in the semen sample. The application of the 150 mM DTT or 50 mM TCEP is preferably applied in a manner so that DTT/TCEP cover the entire swab head to facilitate the recovery of nucleic acids.

In some embodiments, nucleic acids from the swabs may be extracted and analyzed by using the I-Chip in the ANDE Rapid DNA Analysis System. The I-Chip was developed by maximizing the efficiency of the purification module and incorporating a post purification DNA concentration module. These modifications allowed the system to generate STR profiles from samples containing a few nanograms of DNA or less.

Kit for Determining STR Profiles of Nucleic Acids from a Semen Sample

In still yet another aspect, the invention is a kit for determining STR profiles of nucleic acids from a semen sample. In one embodiment, the kit includes a DTT or TCEP solution, a brochure detailing a rapid nucleic acid extraction process from a semen sample as disclosed in the present application, and a swab used for collecting and analyzing the extracted nucleic acids in I-Chip. In some instances, the DTT solution has a DTT concentration equal or close to 150 mM and TCEP solution has a TCEP concentration equal or close to 50 mM. When the semen sample is a semen stain on a fabric, the kit may further comprise a tool, for example, a knife, a razor blade, or a scalpel, for collecting semen samples from a fabric. The kit also contains a dropper bottle containing sterile water or an ampoule containing sterile water. In some embodiments, the kit may be used to generate profiles of the following STRs: D3S1358, TH01, D21S11, D18S51, Penta E, D5S818, D13S17, D7S820, D16D539, CSF1PO, PentaD, Am, vWA, D8S1179, TPOX, and FGA.

Further Analysis of Nucleic Acids Extracted Using this Invention

Extracted nucleic acids may be analyzed in various nucleic acid analysis systems, e.g., ANDE™ Rapid DNA Analysis System (ANDE Corporation). The ANDE™ System is a fully automated system with on-board expert system software for automated data analysis. The system can generate called STR profiles from high DNA content samples (e.g. buccal swabs) in approximately 90 minutes and from casework, sensitive site exploitation, and mass disaster samples (e.g. bloodstains, chewing gum, drinking containers, clothing, touched items such as steering wheels, door handles, cell phones, and keyboards, liver, lung, brain, bone, and teeth) in approximately 105 minutes. The system is designed for use with the high and low DNA content chips ("A-Chip" and "I-Chip" as referred to herein). The A-Chip and I-Chip consumables are "all-in-one" disposable cassettes, factory pre-loaded with all reagents needed for STR analysis. The A-Chip is designed for samples with large quantities of DNA—for example, buccal swabs, and the I-Chip is designed for samples that typically contain smaller quantities of DNA—for example, a small blood stain, a cigarette butt, or a steering wheel swab. Both of these consumables are suitable for the processing of bone, teeth, semen, and other samples prepared using the teachings herein. The quantity of DNA present in bone may be affected by several factors including PMI to collection, condition of remains (e.g. decomposed remains, burned), presence or absence of marrow, the type of bone from the body, and the age and health of donor. Relatively fresh and intact bone may likely contain greater quantities of DNA than older that has been exposed to the environment or insult.

In one embodiment, a small portion of the supernatant may be directly transferred onto a swab, which may then be inserted into a rapid DNA analysis system, for example, either an A-Chip or I-Chip, for nucleic acid analysis. The portion of the supernatant may be about 100-150 µl. The swab may be an ANDE® swab or a similar swab which would fit the swab cap and swab chamber in a Rapid DNA Analysis system. The A-Chip is described in Tan et al, Inv. Genetics 4 2013 and in Grover et al, Intg J Legal Med 2017; and the I-Chip in Turingan et al, Inv Genetics 7 2016, both of which are incorporated in their entirety herein.

Example 1

Extraction, Purification, and Analysis of Nucleic Acids from Bone

In this example, we performed a rapid nucleic acid extraction from bone samples and analyzed the extracted nucleic acid using a swab and the I-Chip in the ANDE system.

Bone samples were artificially degraded to mimic casework and/or disaster victim identification in plane crash tragedies (e.g. Indonesia AirAsia Flight 8501). Mock decomposition of bone samples (femoral and humeral fragments) was performed by soaking the fragments in Atlantic coast salt water at 84° F. (average temperature of Java Sea) for 4 days. The bone samples were then washed with water, bleached, washed again with water, and then ethanol. After drying, the bones were grinded by either freezer mill to obtain powdered samples or simply hammered to obtain fragmented or granulated samples. The grinded bone samples were placed into four separate 2 ml centrifuge tubes containing 200 mg hammered bone, 500 mg hammered bone, 200 g freeze-milled bone, and 500 mg freeze-milled bone, respectively.

We then added 200-350 µl of 0.5 M EDTA into each of the tubes. EDTA was added to demineralize the bone sample and help release DNA. The tubes were then vortexed for 1 min using a benchtop vortexer at "10" speed setting. The tubes were then centrifuged (Centrifuge 5417R; Eppendorf North America, Hauppauge, NY, USA) at 20,000 rcf for 2 minutes to separate the bone particulates from the demineralized supernatant. About 1500 of each supernatant was pipetted onto an ANDE swab for sample insertion into I-Chip for analysis of STR profiles. The STRs were D3S1358, TH01, D21511, D18551, Penta E, D5S818, D13517, D7S820, D16D539, CSF1PO, Penta D, Am, vWA, D8S1179, TPOX, and FGA. As a result, we were able to obtain STR profiles for each of the four test samples. See FIGS. 1-4, nucleic acids extracted from each of the four test samples. Full STR profiles (PP16) were generated from either milled or hammered samples and with decreased in bone input from 500 mg to 200 mg.

Figure 8:
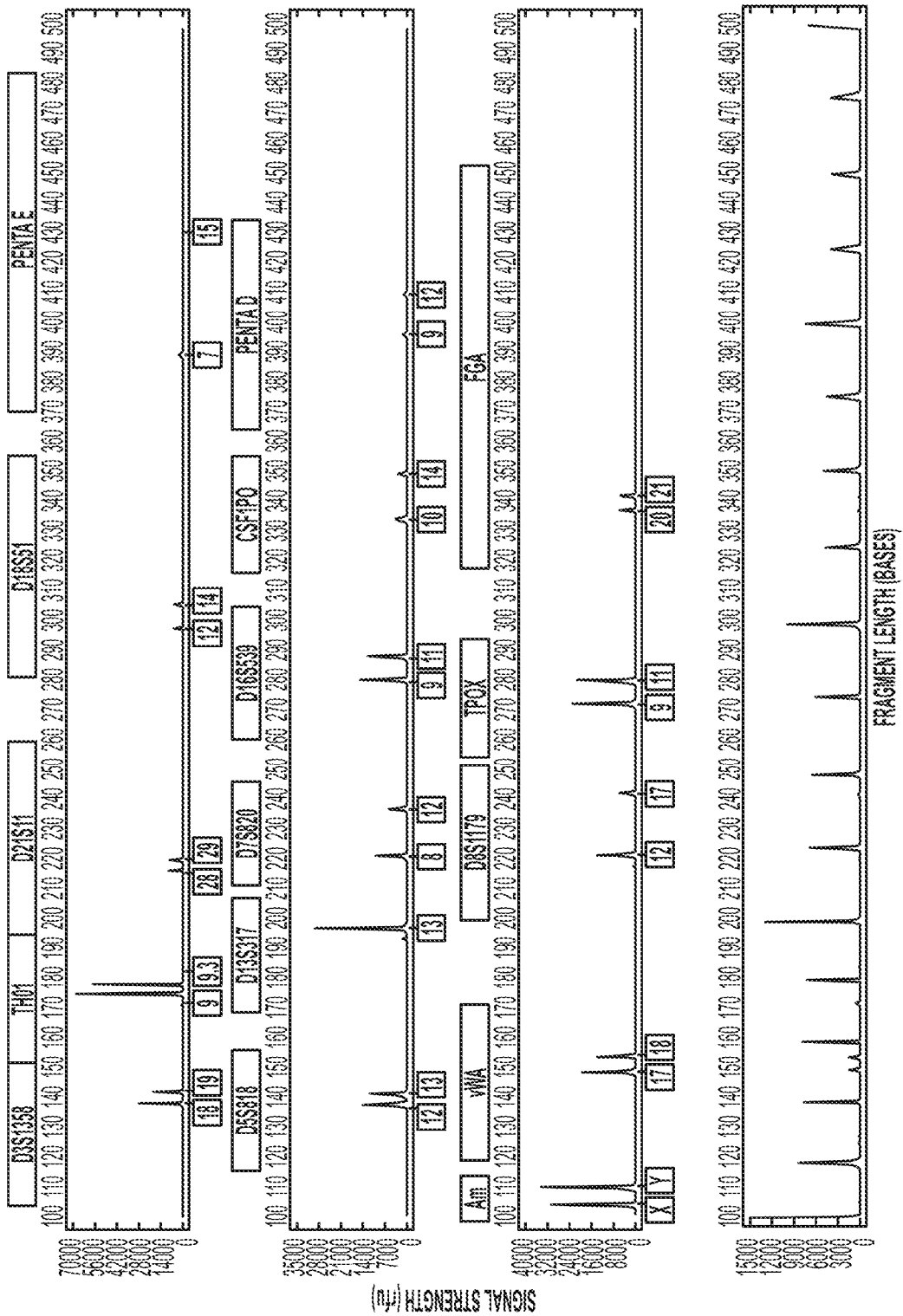
FIG. 8 shows a full 16-locus STR profile of nucleic acid purified from 200 mg freeze-milled root of fresh molar tooth sample. Sample was demineralized for 10 minutes and analyzed in an I-Chip.

As a positive control, we performed nucleic acid extraction from 500 mg freeze-milled bone from the same source following the total demineralization method reported in Loreille et al., Forensic Science International: Genetics 1 (2007) 191-195. Specifically, the bone powder was incubated overnight in 7.5 ml of extraction buffer (EDTA 0.5 M and 1% laurylsarcosinate) and 200 ul 20 mg/mL proteinase K in a rotary shaker at 56° C. Supernatant was transferred to an Amicon 30 centrifugal filter unit (Millipore) for concentration to approximately 150 µl and loaded onto a NetBio swab for a fully-integrated run in an I-CHIP. As a result, we were able to obtain a STR profile from the purified DNA. See FIG. 8. Full STR profile was generated using the long process of total demineralization. Overall signal strength was comparable to profiles generated from the simplified and fast bone analysis method.

In the traditional method, the demineralization buffer contains EDTA, detergent, and proteinase K, high initial buffer volume (7.5 ml for 500 mg of powder) is used, the demineralization requires overnight incubation at 56° C. with agitation in a rotary shaker, and the process requires sample concentration and washing using centrifugal units.

In contrast, in the present invention, the demineralization solution is simply an EDTA solution without any detergent or proteinase K. In addition, there is no requirement of incubation for extended period of time or heating. Indeed, the demineralization process takes less than 5 mins including sample handling and solution transfer. The resultant supernatant contains the extracted nucleic acids that can be used directly to generate profiles using our HDC or LDC BCS and ANDE system.

Example 2

Extraction and Analysis of Nucleic Acids from Tooth

Figure 9:
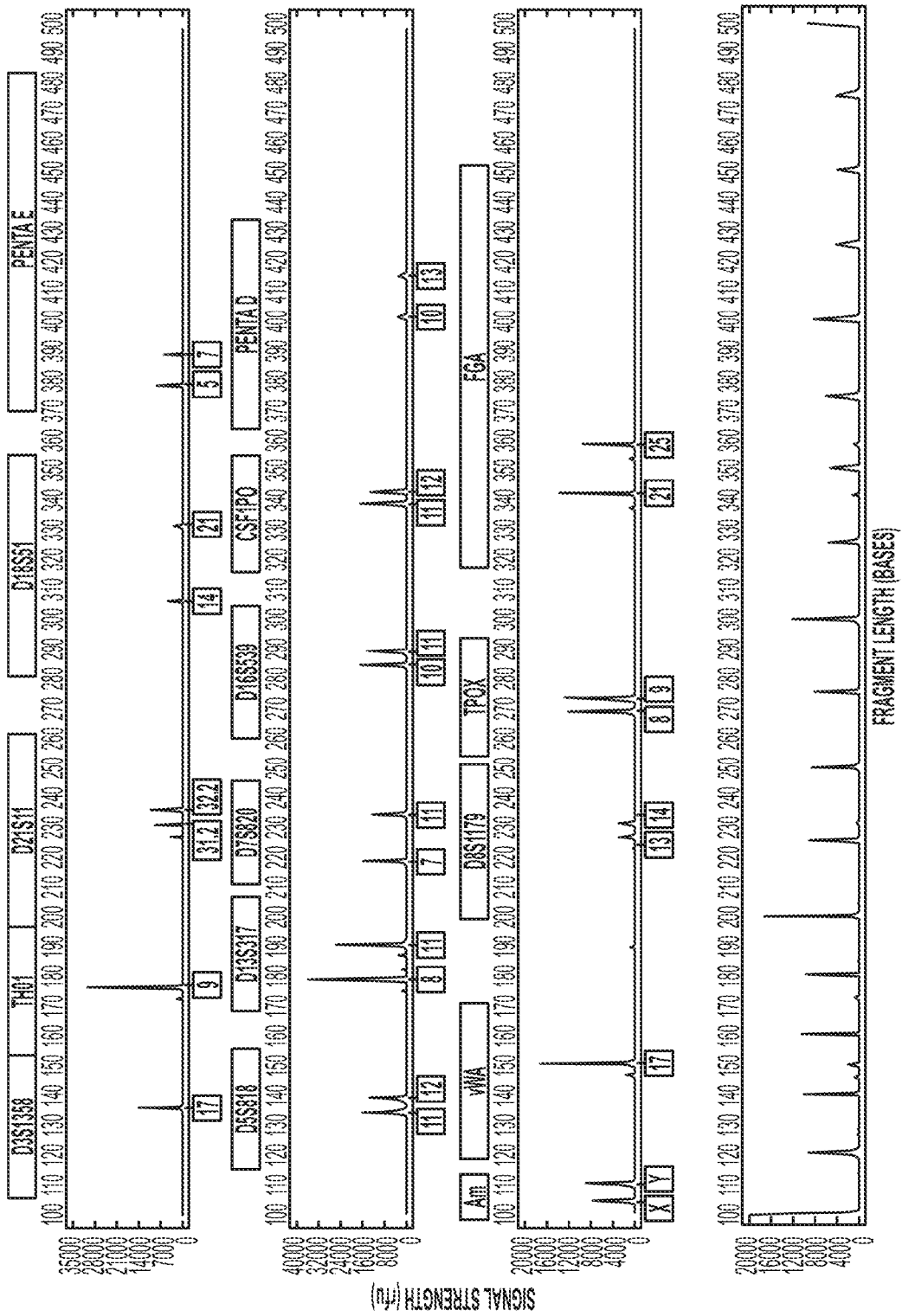
FIG. 9 shows a full 16-locus STR profile of nucleic acid purified from dried semen stain on denim and analyzed in an I-Chip.
Figure 10:
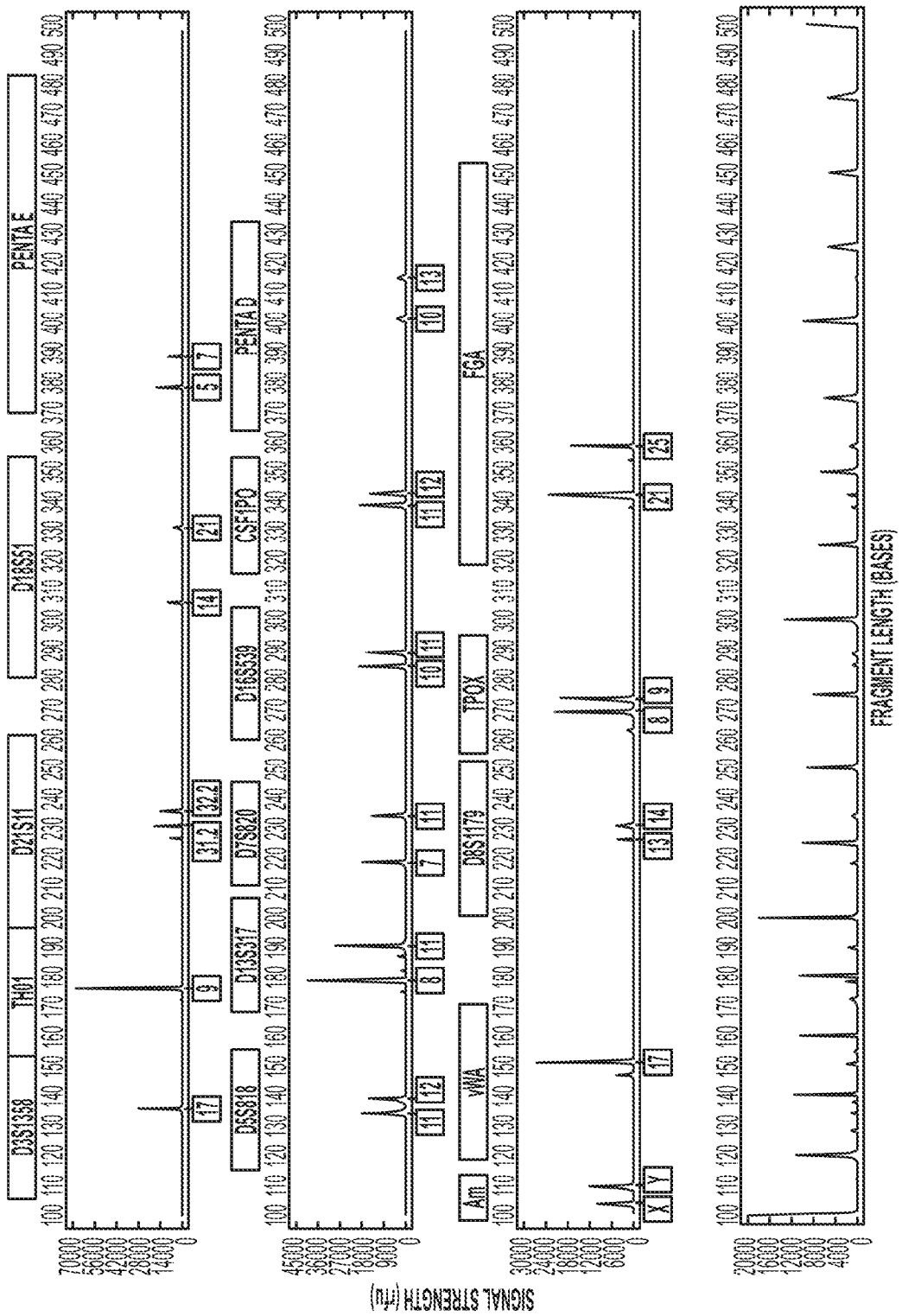
FIG. 10 shows a full 16-locus STR profile of nucleic acid purified from dried semen on cotton and analyzed in an I-Chip.
Figure 11:
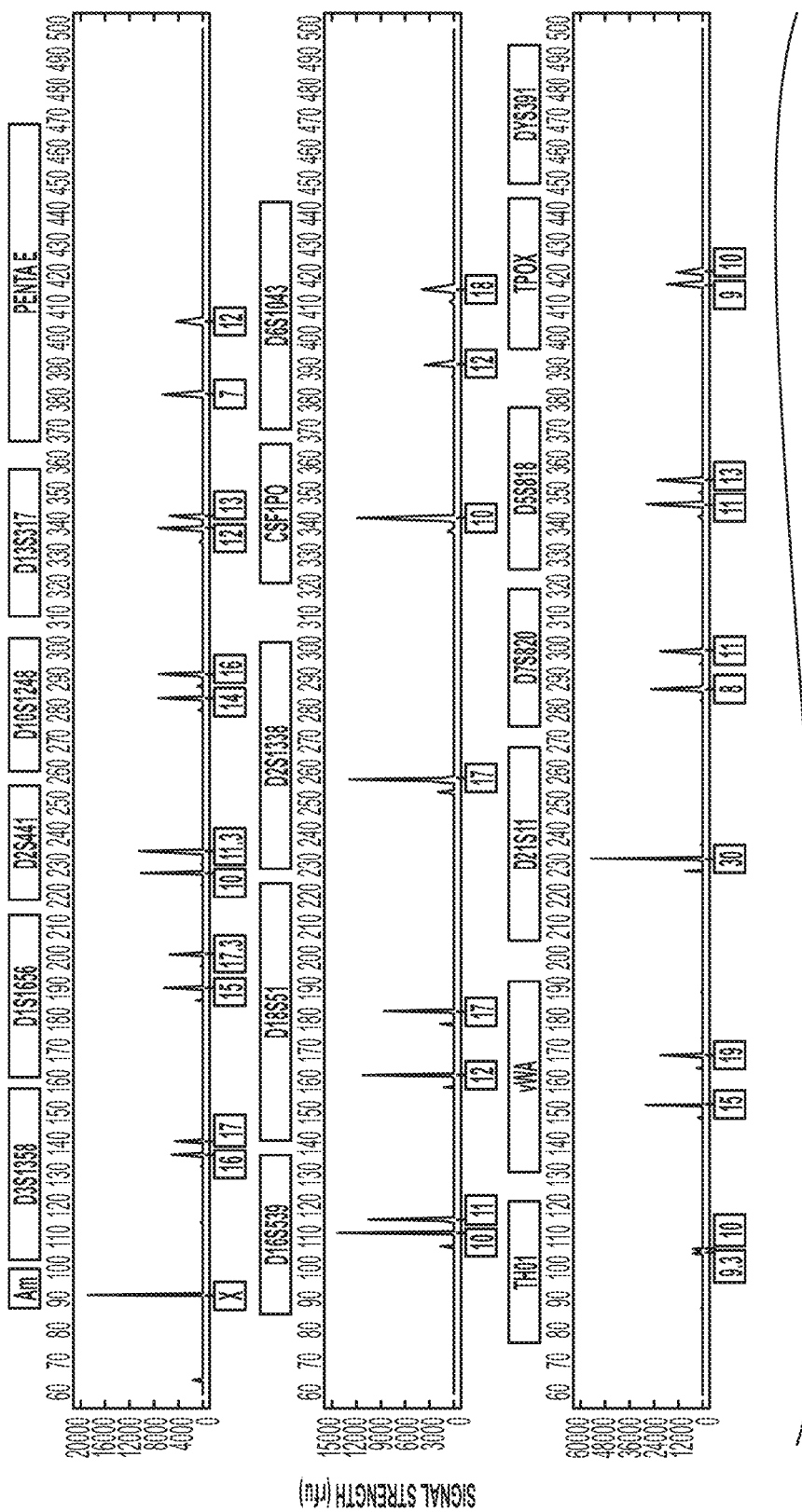
FIG. 11 shows a full 27-locus STR profile of nucleic acid purified from 5 mg freeze-milled bone powder of fresh femur sample. Sample was demineralized for 1 minute and analyzed in an A-Chip.
Figure 11:
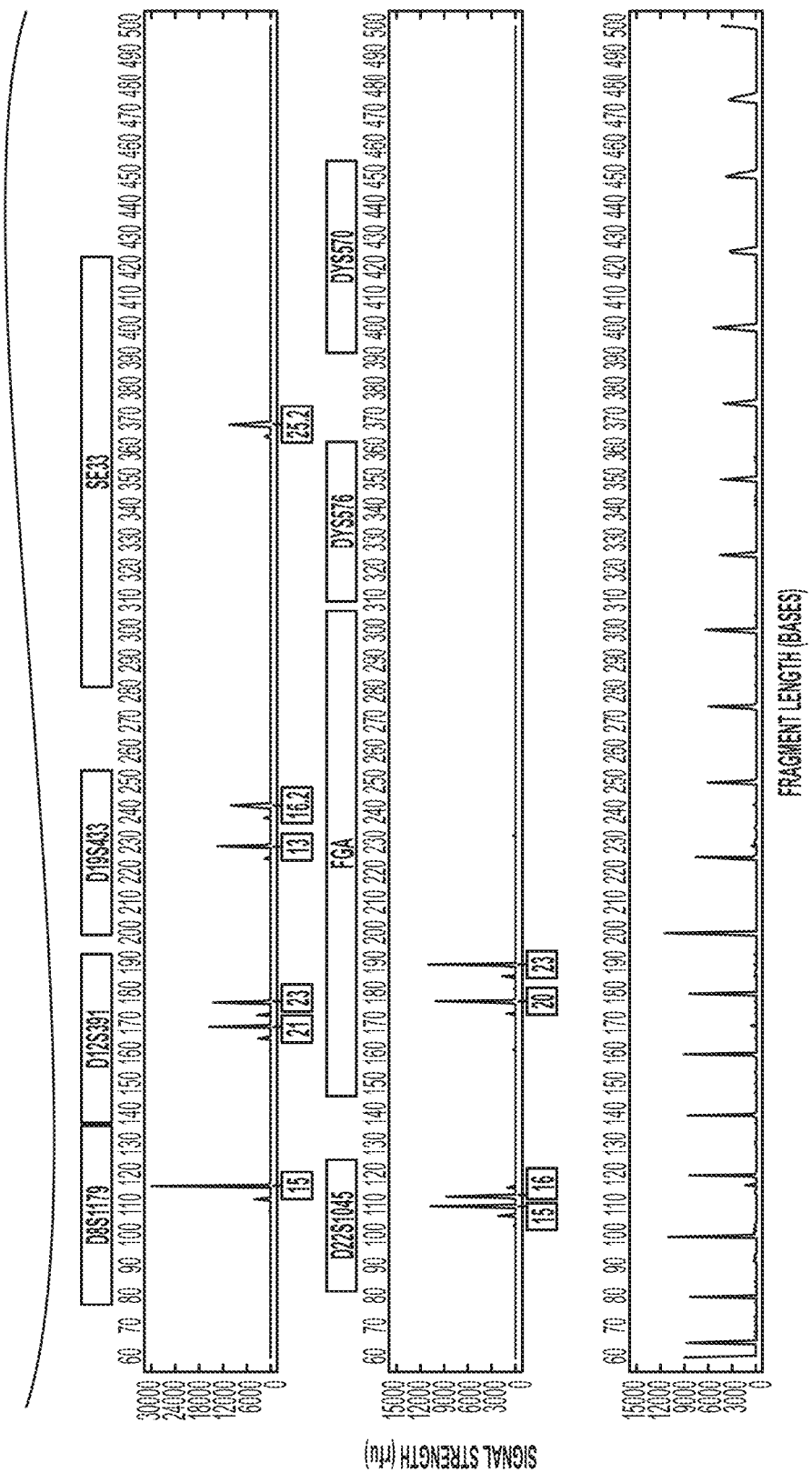
Figure 12:
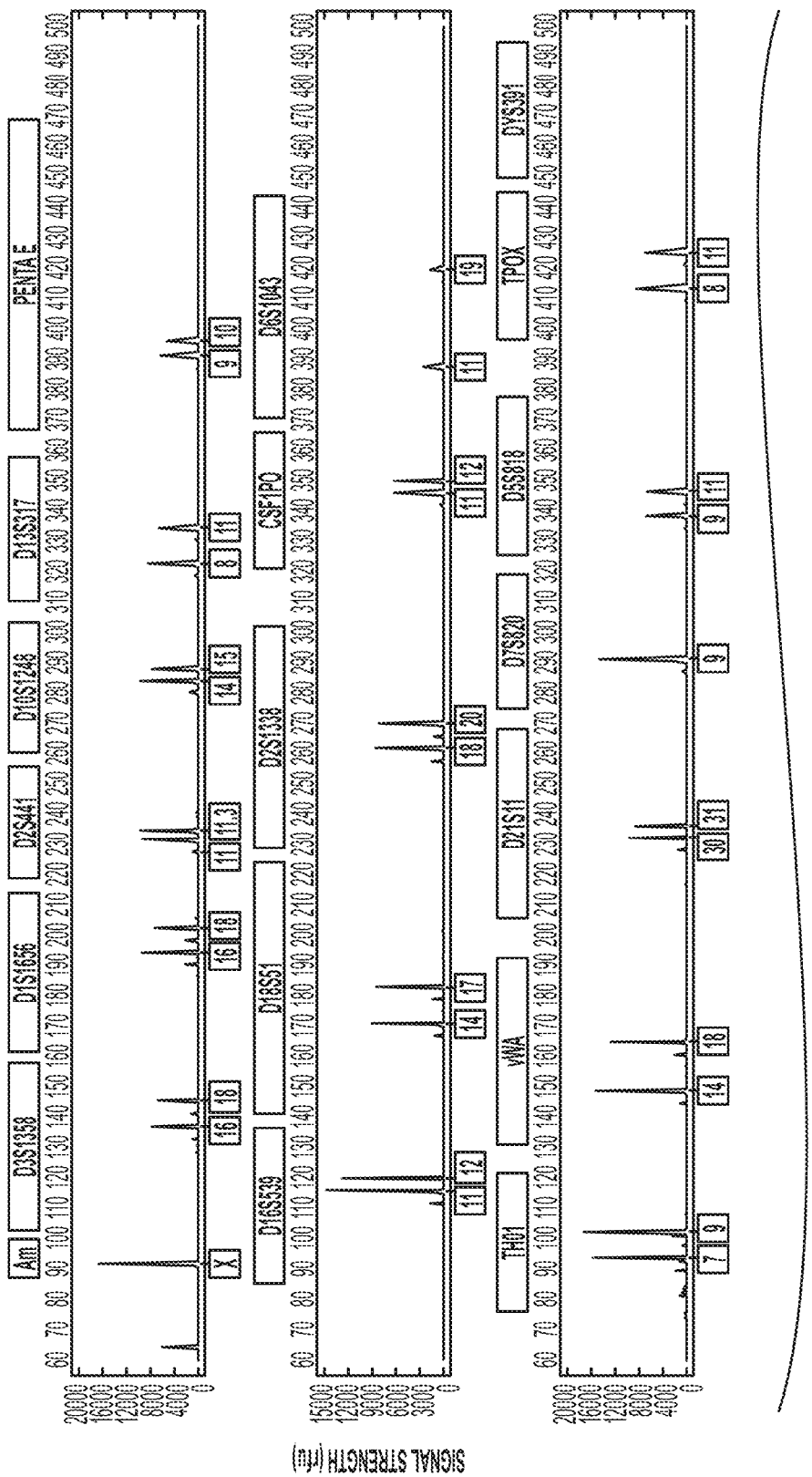
FIG. 12 shows a full 27-locus STR profile of nucleic acid purified from 5 mg hammered bone fragments of fresh femur sample. Sample was demineralized for 1 minute and analyzed in an A-Chip.
Figure 12:
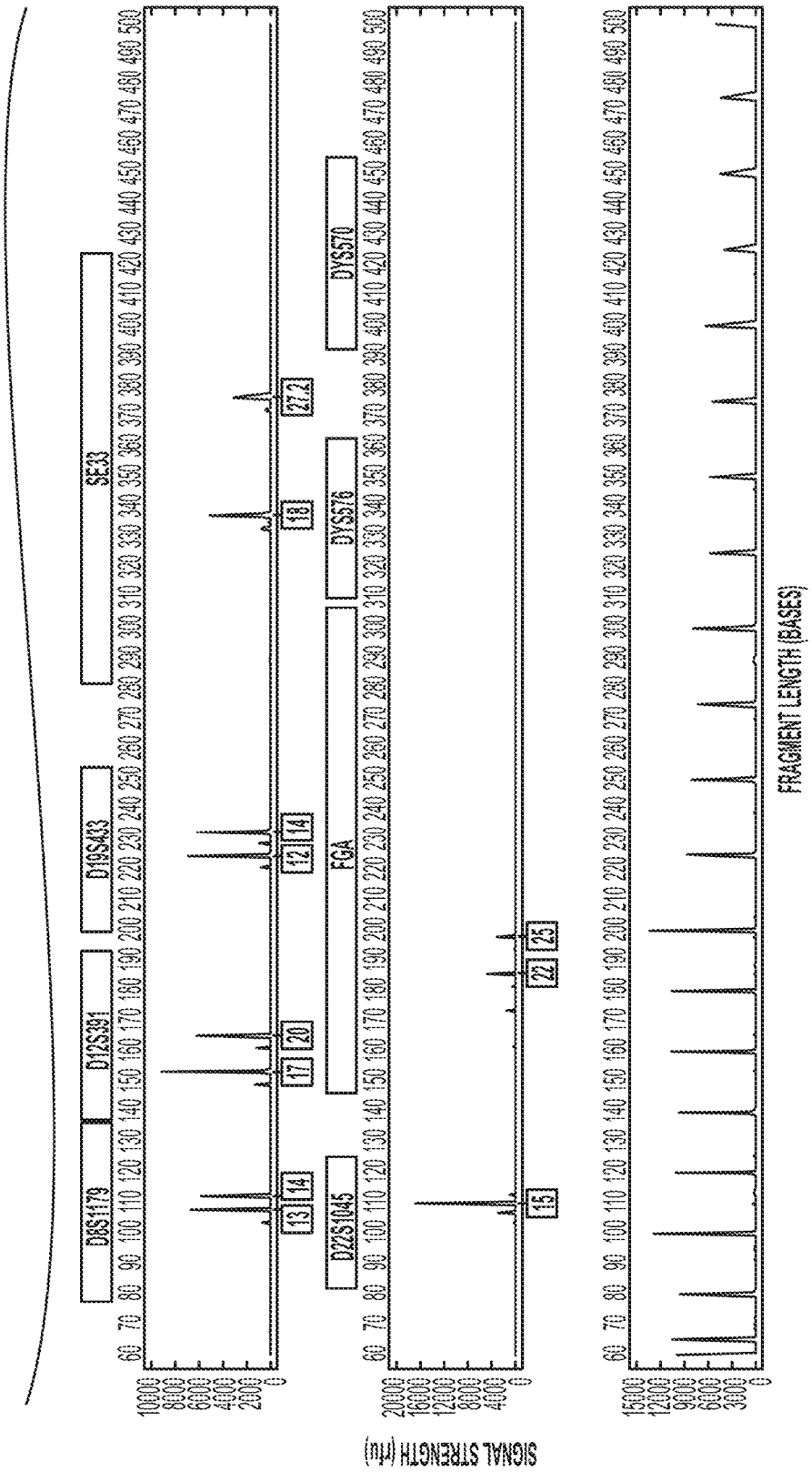
Figure 13:
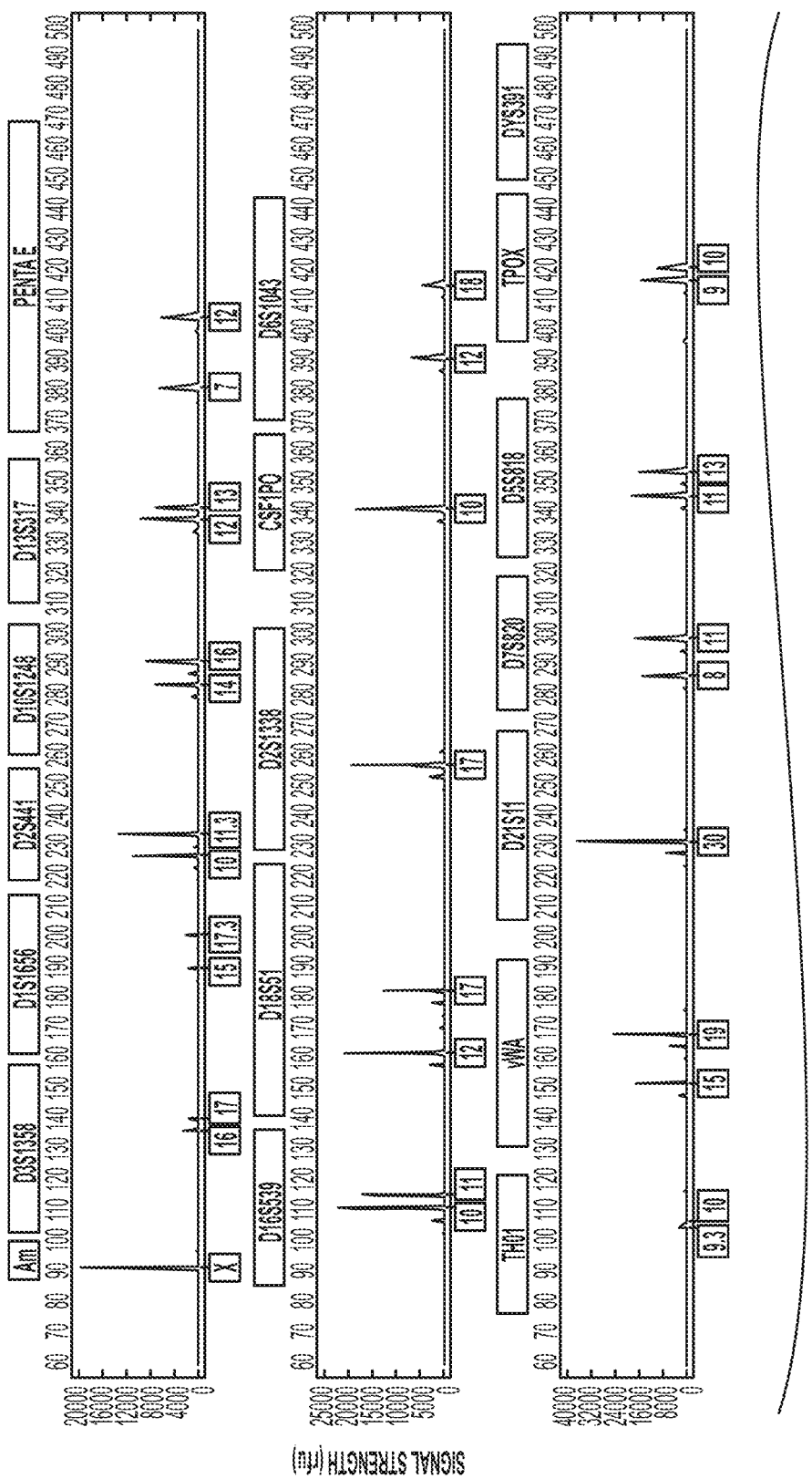
FIG. 13 shows a full 27-locus STR profile of nucleic acid purified from 5 mg freeze-milled bone powder of fresh femur sample and using only 15 μl of 120 μl bone demineralized solution for analysis in an I-Chip. The sample input is theoretically equivalent to 0.6 mg sample. Sample was demineralized for 1 minute.
Figure 13:
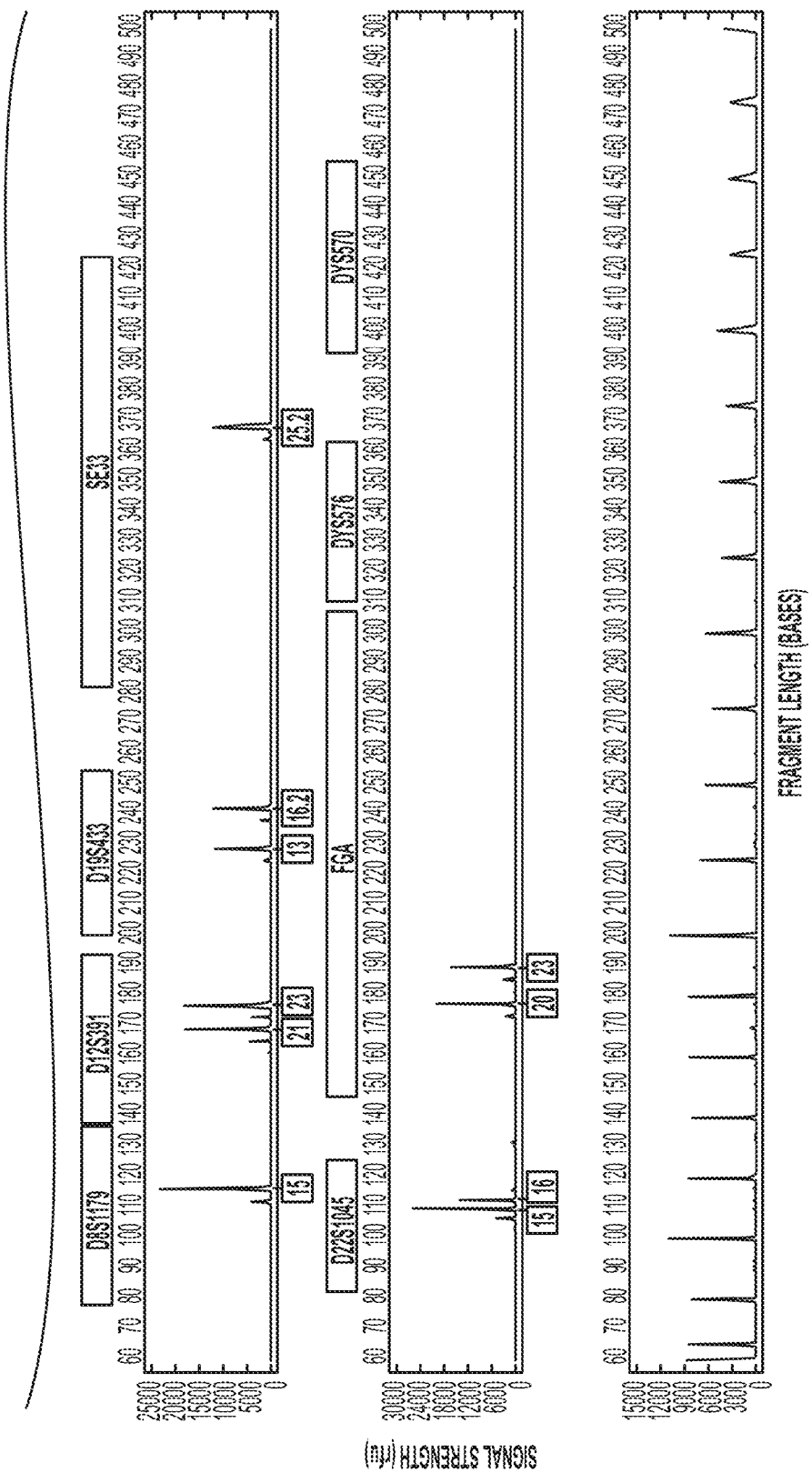
Figure 14:
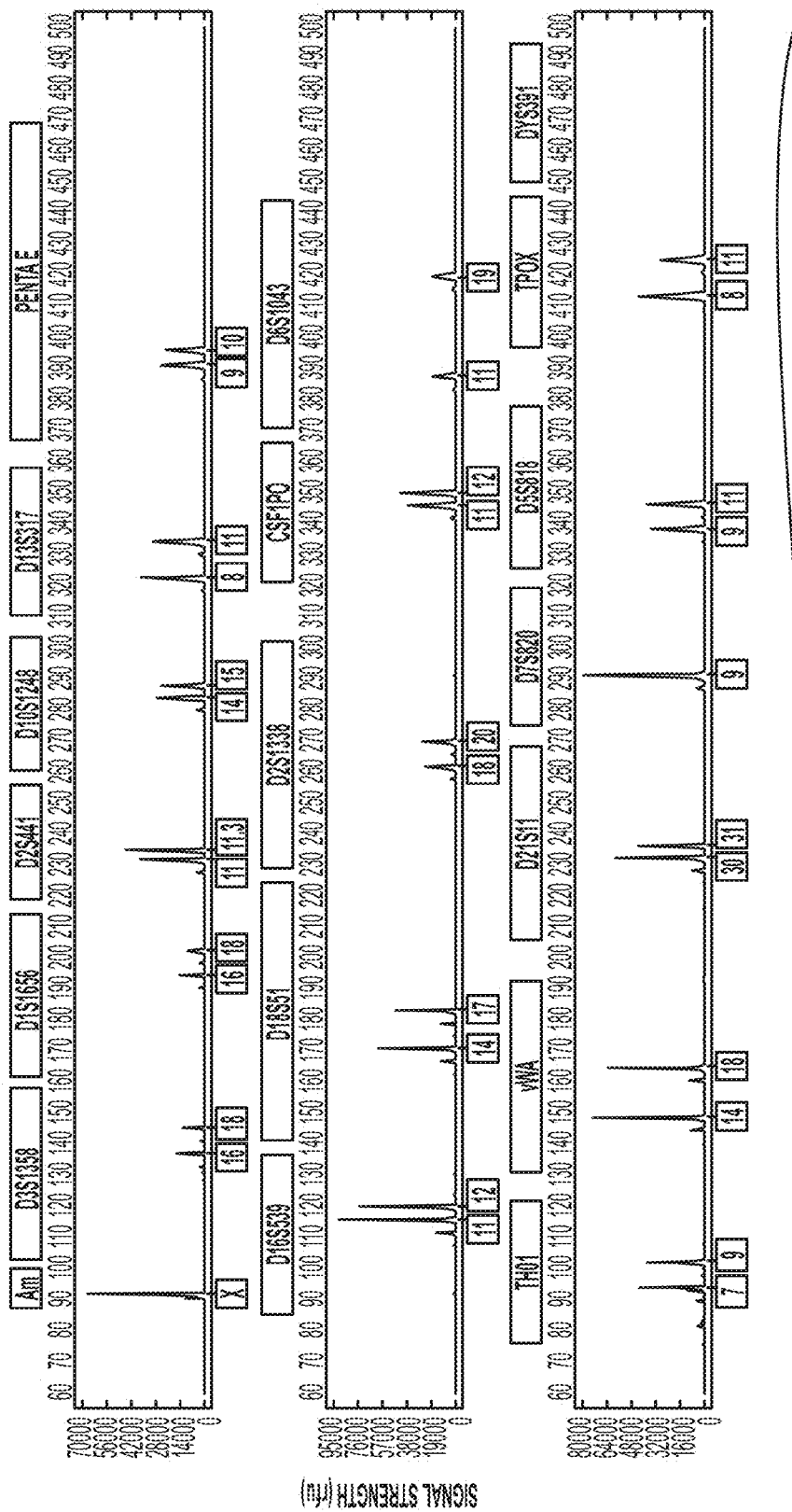
FIG. 14 shows a full 27-locus STR profile of nucleic acid purified from 5 mg hammered bone fragments of fresh femur sample and using only 15 μl of 120 μl bone demineralized solution for analysis in an I-Chip. The sample input is theoretically equivalent to 0.6 mg sample. Sample was demineralized for 1 minute.
Figure 14:
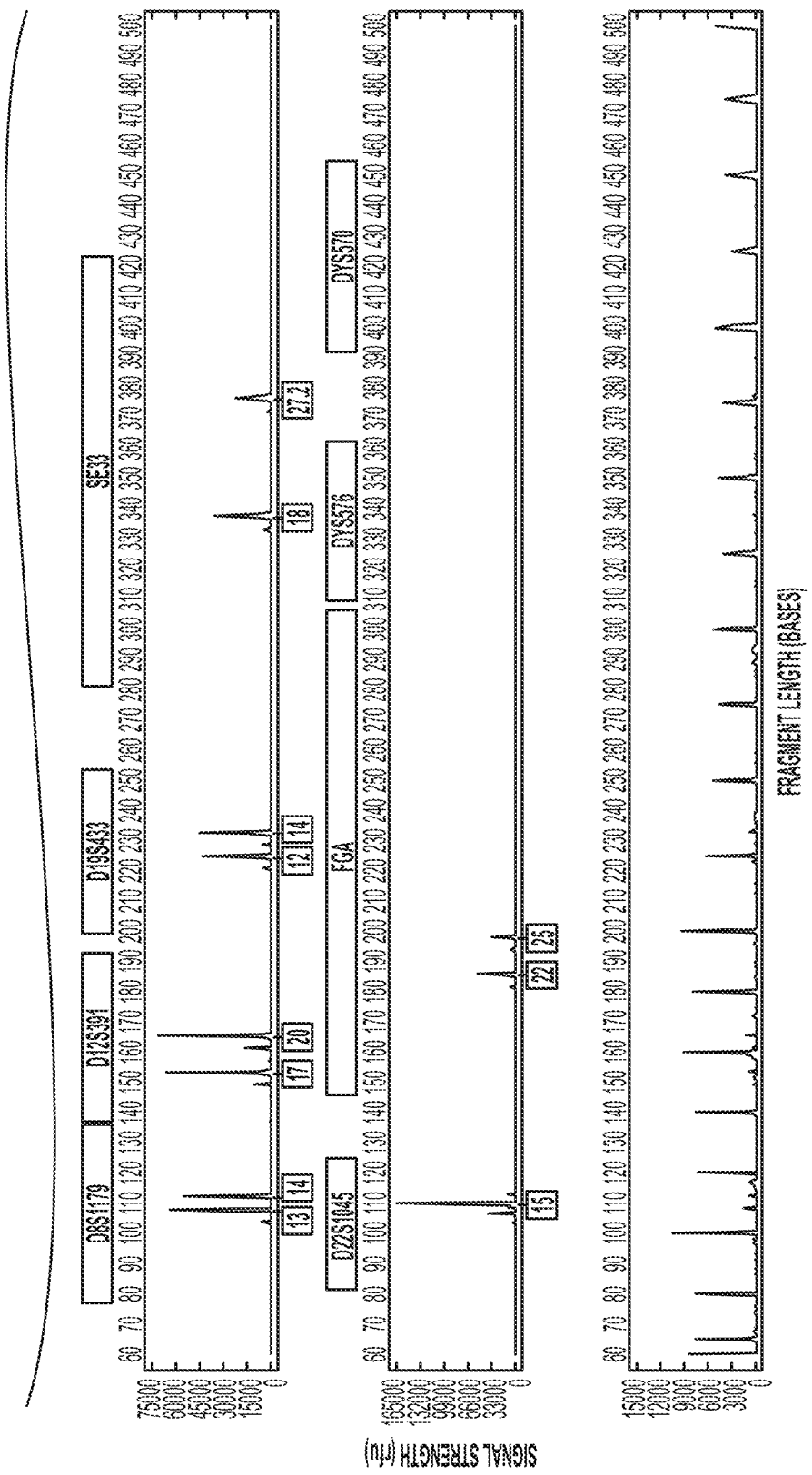
Figure 15:
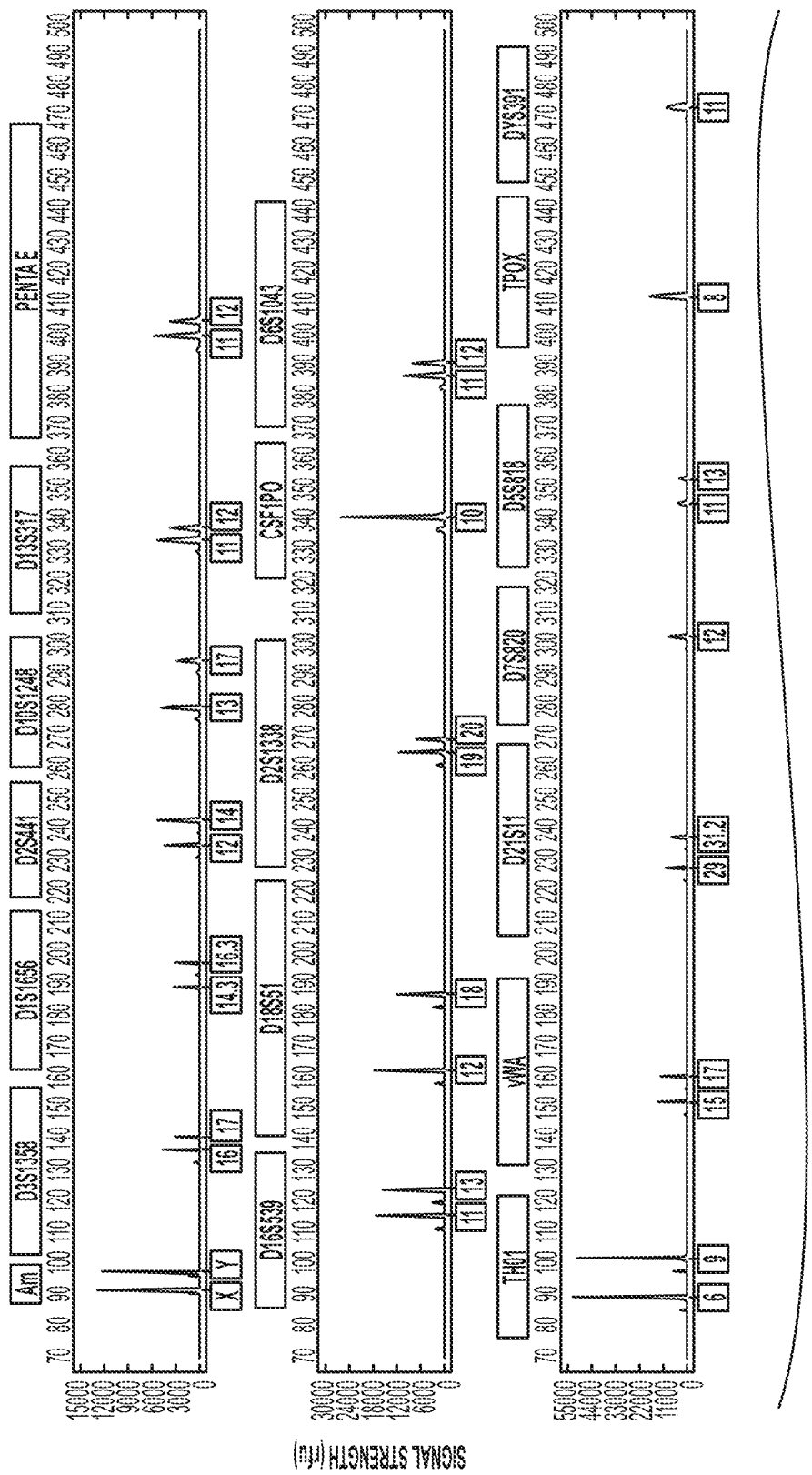
FIG. 15 shows a full 27-locus STR profile of nucleic acid purified from 5 mg hammered fresh distal phalanx bone sample and using only 15 μl of 120 μl bone demineralized solution for analysis in an I-Chip. The sample input is theoretically equivalent to 0.6 mg sample. Sample was demineralized for 1 minute.
Figure 15:
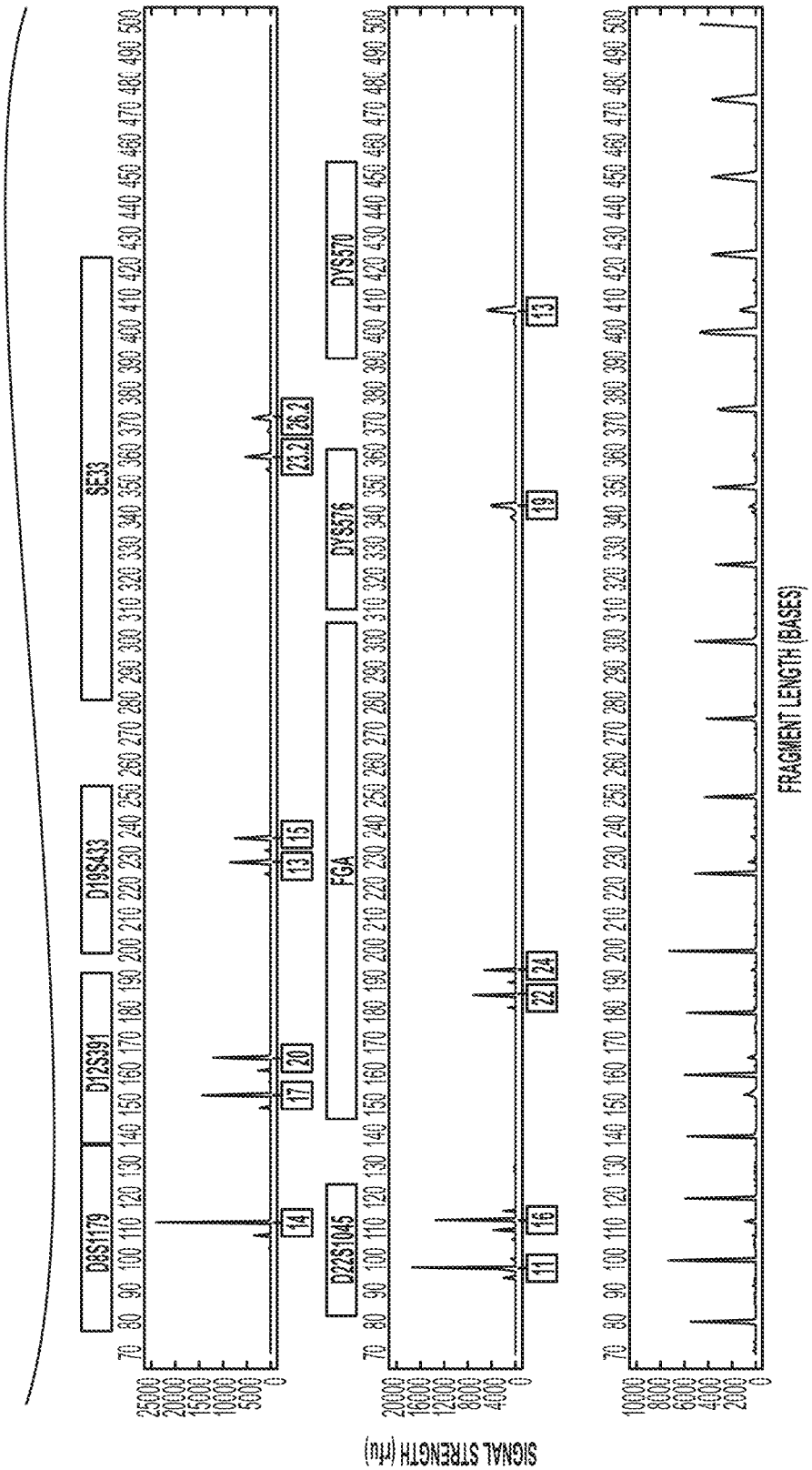
Figure 16:
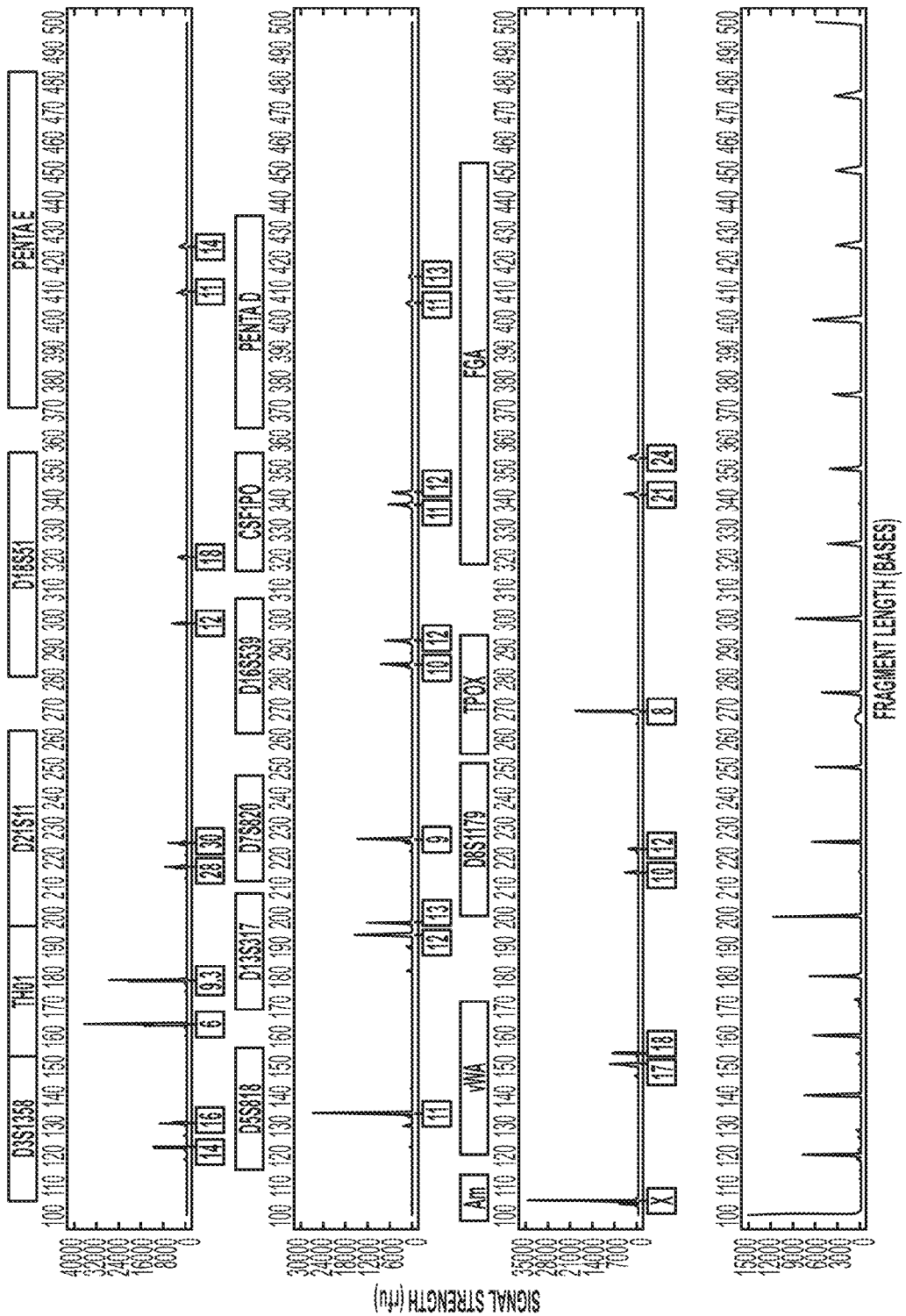
FIG. 16 shows a full 16-locus STR profile of nucleic acid purified from 200 mg freeze-milled fresh tooth root (not subjected to any form of degradation). Tooth was demineralized for 1 minute and analyzed in an I-Chip.

In this example, we performed a rapid nucleic acid extraction from tooth samples and analyzed the extracted nucleic acid in swab and LDC BCS system. The procedure is a modification of Example 1. After a 1 minute vortex, the tooth sample was incubated for 10 mins at 56° C. to enhance demineralization. As a result, we were able to obtain STR profiles of the nucleic acids extracted from the tooth sample. See FIG. 9 showing STR profile of the nucleic acids extracted from 200 mg freeze-milled tooth powder from root.

Our results indicate that a 1 minute demineralization process with tooth, was insufficient to obtain consistent full or good partial profiles. This is probably due to the more compact matrix of tooth compared to bone and a longer demineralization is needed for DNA release. The root of a tooth sample has been reported to contain more DNA than the crown or other parts of the tooth. We notice that when we process crown, as opposed to root tissue from the same tooth sample, we are more consistently able to obtain full STR profiles from root and not from crown tissue. For fresh tooth or tooth subjected to degradation, root is preferred over crown. If only crown is available for processing, one may put in more material (say 500 mg instead of 200 mg) and milled is preferred over hammered.

Figure 17:
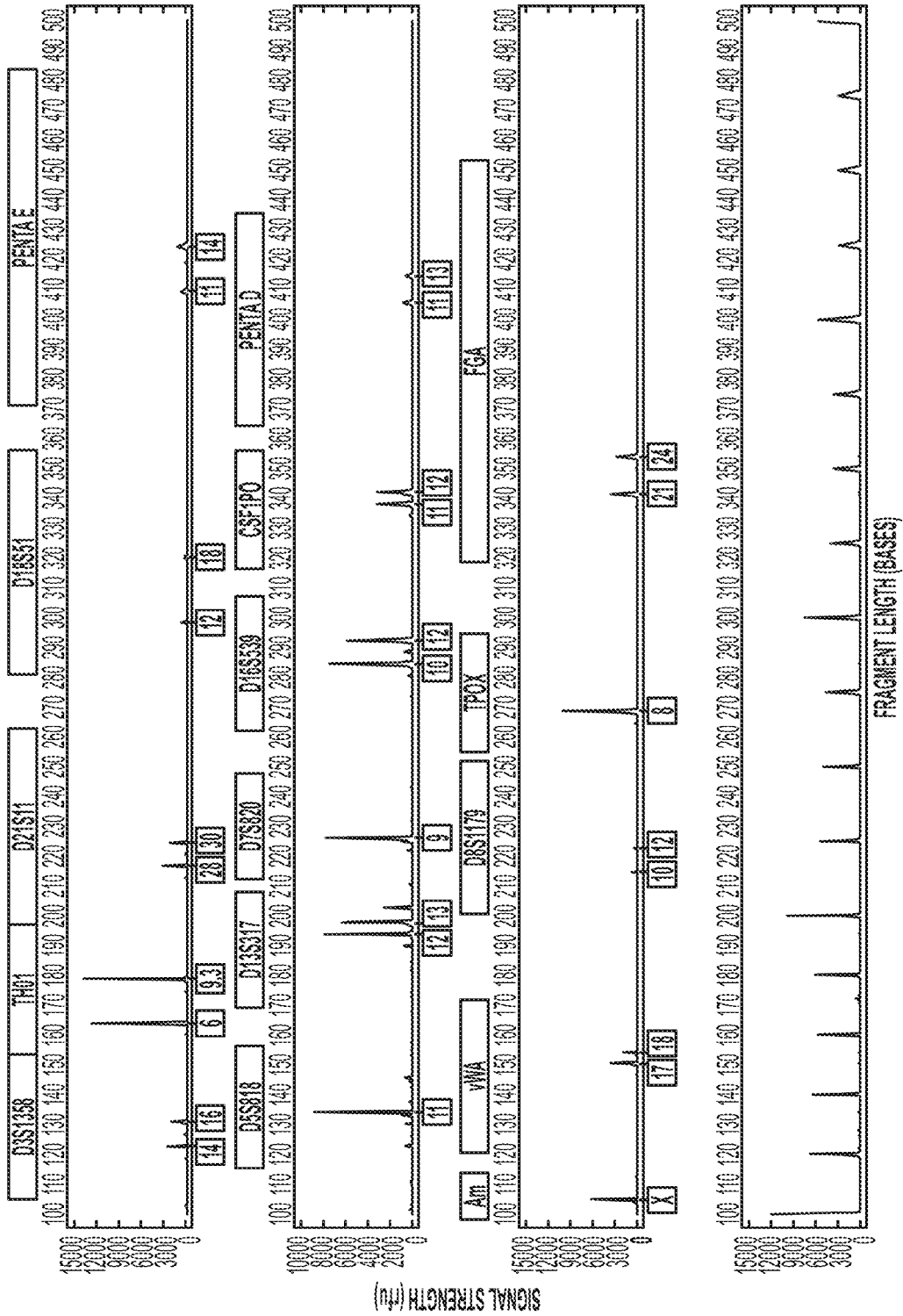
FIG. 17 shows a full 16-locus STR profile of nucleic acid purified from 200 mg freeze-milled root of an artificially aged molar tooth sample. Tooth was soaked for 1 month in saltwater at 84° F., cleaned and dried prior to separating the root from crown, demineralized for 10 minutes, and analyzed in I-Chip.
Figure 18:
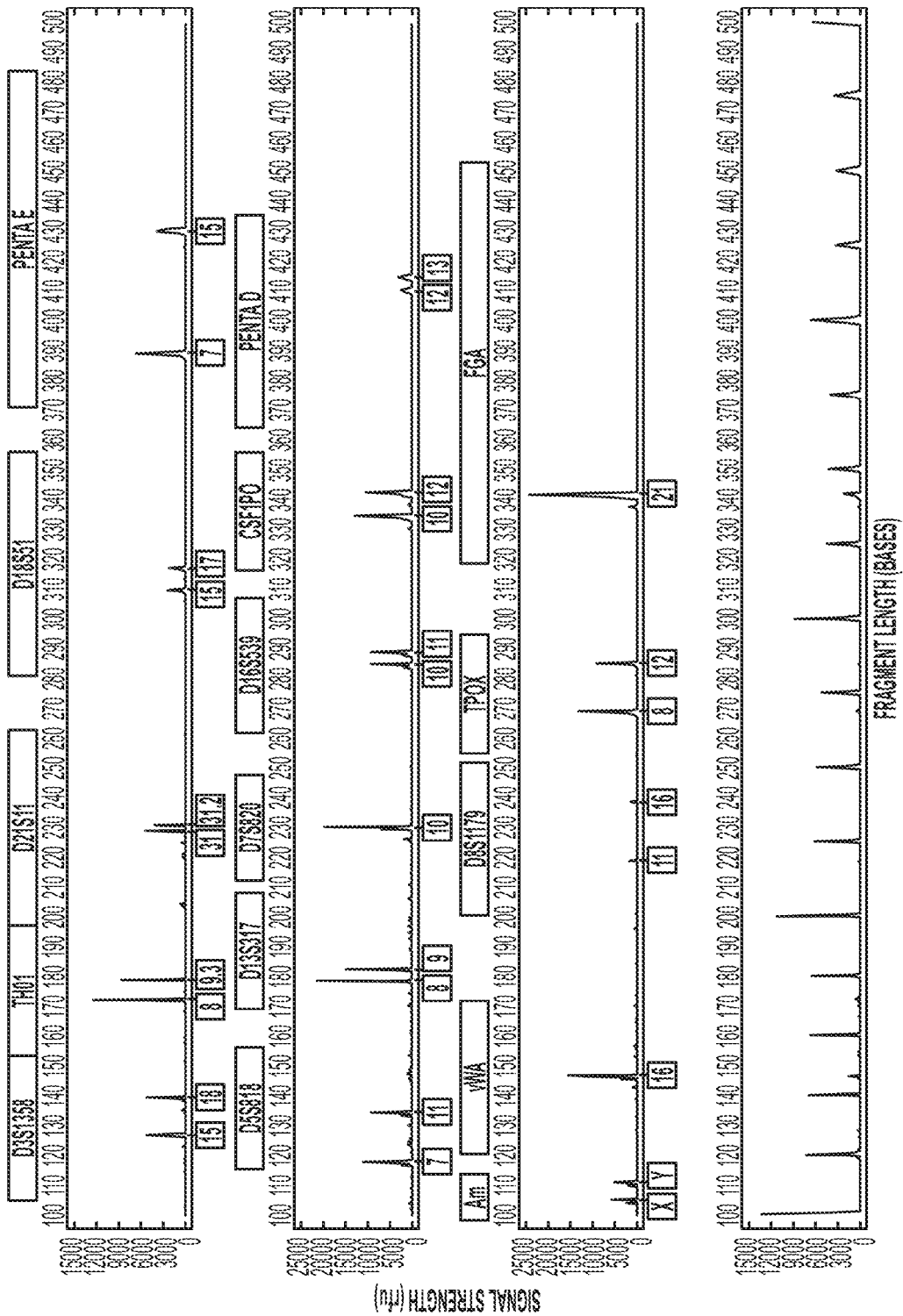
FIG. 18 shows a full 16-locus STR profile of nucleic acid purified from 200 mg milled root of a forensic molar tooth sample. Tooth was found buried in soil for at least 2 years, cleaned and dried prior to separating the root from crown, demineralized for 180 minutes, and analyzed in an I-Chip.
Figure 19:
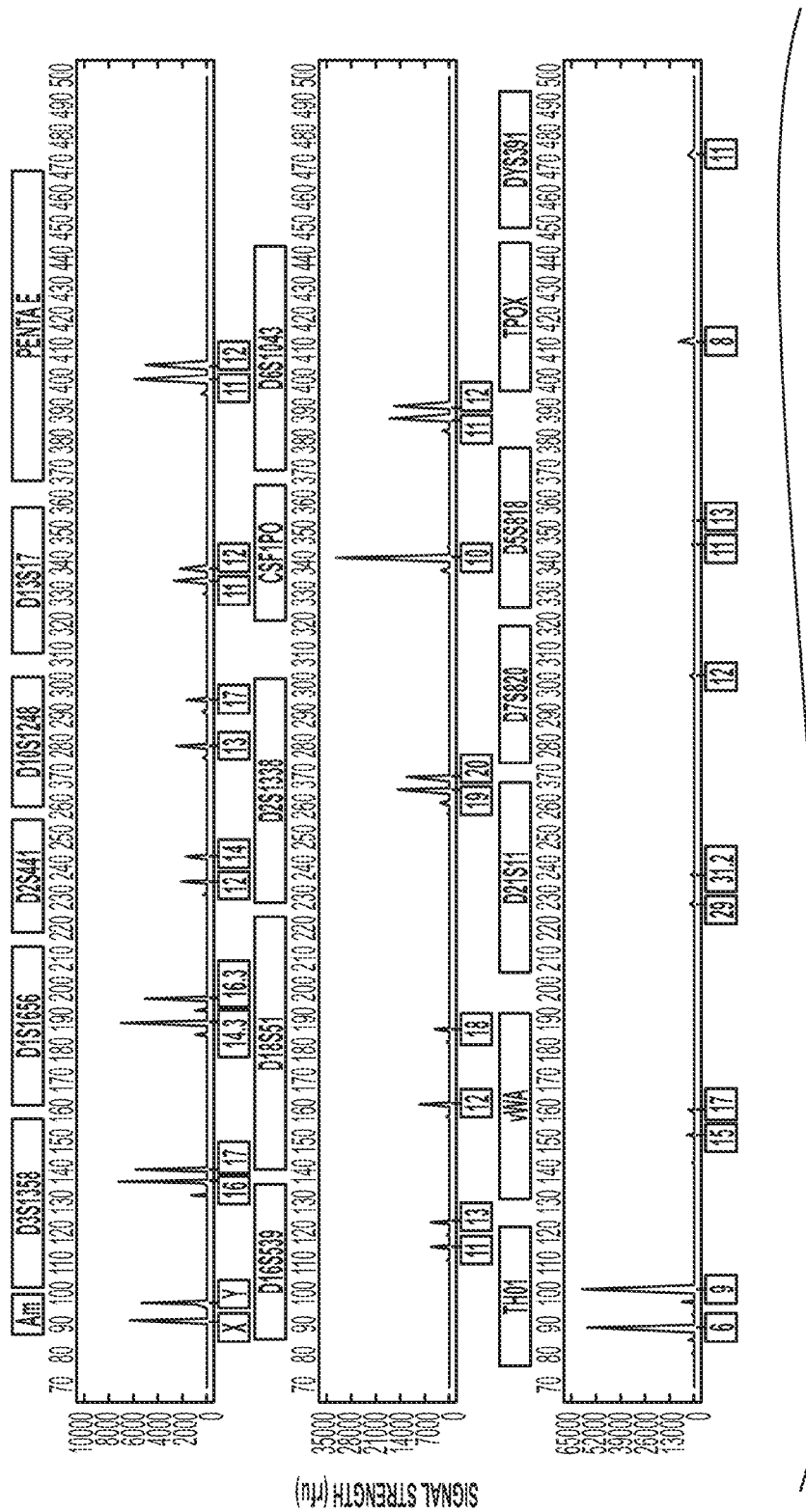
FIG. 19 shows a full 27-locus STR profile of nucleic acid purified from 10 mg hammered root fragments of fresh molar tooth sample. Sample was demineralized for 10 minutes and analyzed in an I-Chip.
Figure 19:
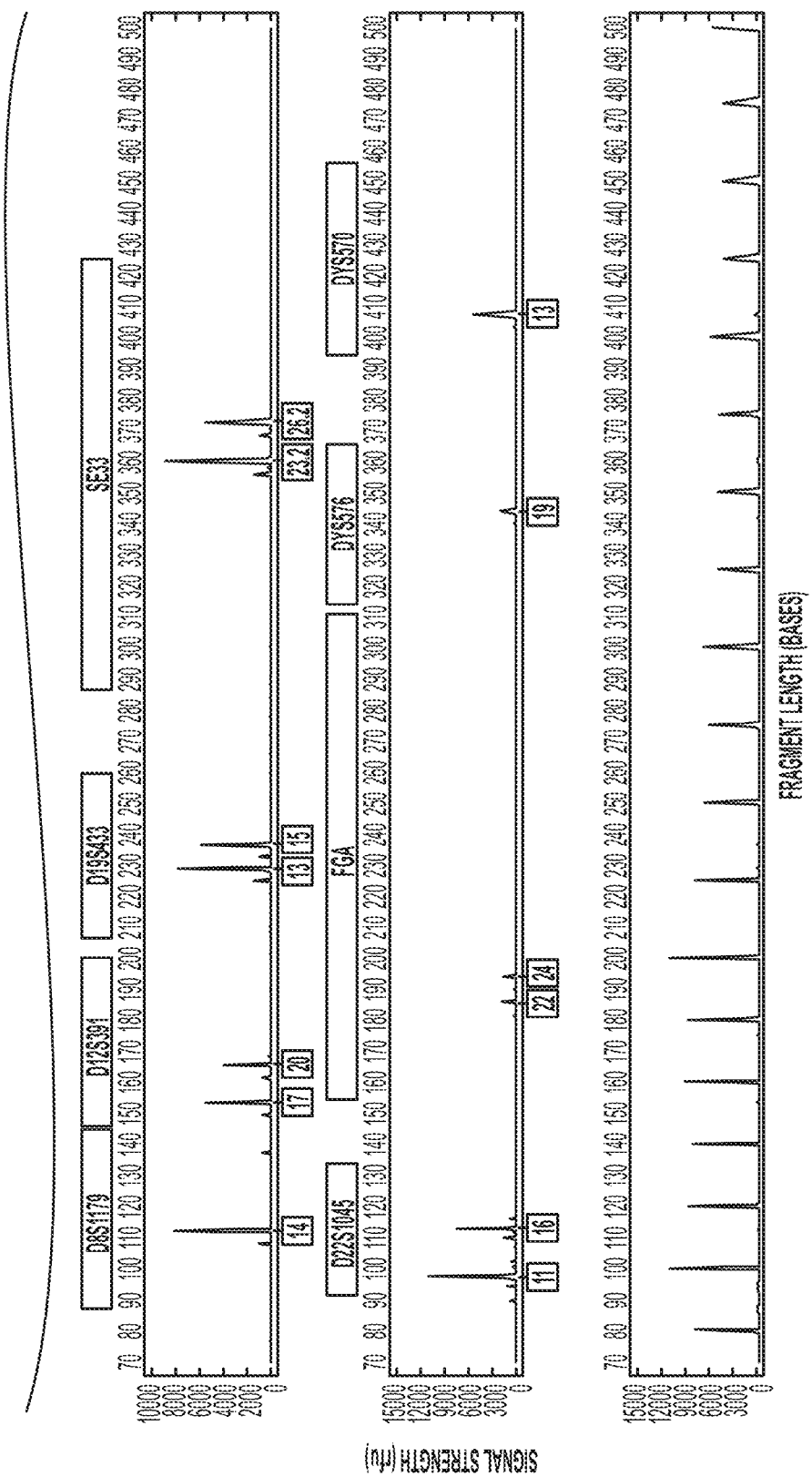

FIG. 17 is a 16-locus full profile on 200 mg tooth root (undegraded); FIG. 18 is a 16-locus profile from tooth root aged 1 month 84 F saltwater (200 mg); FIG. 19 is the artificially aged molar which was cleaned in bleach and dried prior to cutting/milling.

Example 3

Extraction and Analysis of Nucleic Acids from Casework Tooth Samples

Casework tooth samples were obtained from burnt bodies that had been buried for at least 2 years. Tooth samples were washed in running water and antibacterial soap while scraping the surface with cloth and bleach. The samples were then subjected to bleach-sterile-water-ethanol rinse, allowed to dry for 10 mins. The root was separated from the crown using a dremel. The root was then freeze-milled and 200 mg was demineralized.

Example 4

Extraction and Analysis of Nucleic Acids from Neat Semen

Typically, semen samples contain ~50 million cells per mL. After thawing on ice, the tube containing the semen sample was carefully opened and the sample was gently mixed by pipetting up and down prior to sample retrieval to ensure homogeneity of the sample. A 50 µl of semen diluted 10-100 folds in 1×PBS buffer was pipetted on an ANDE swab. To the swab, a final concentration of 150 mM DL-Dithiothreitol (DTT) (Sigma Aldrich; Catalog #43816) or 50 µl of 50 mM Tris(2-carboxyethyl)phosphine hydrochloride (TCEP) (Sigma Aldrich; Catalog #646547) was added and incubated for 1-10 minutes at room temperature prior to analysis in I-Chip.

Example 5

Extraction and Analysis of Nucleic Acids from Dried Semen on Fabric

In this example, we performed a rapid nucleic acid extraction from semen samples and analyzed the extracted nucleic acid in swab using the I-Chip. Here we used a mock semen sample which was prepared as described in step 1 below. For casework semen samples, this semen sample preparation step (step 1) is skipped.

Step 1: Preparing a Mock Semen Stained Clothing

Approximately 100 µl of neat semen was transferred onto a cotton fabric and/or denim. While the semen stain was still wet, the immediate area surrounding the stain was marked with a permanent marker to ensure that biological materials were collected from the correct location, as the dried stain may not be visible to the unaided eye. The semen stain on fabric was let dry overnight at room temperature.

Step 2: Collecting Dried Semen Samples from Clothing

This step was carried out to collect DNA-containing semen sample from the semen stained fabric pieces. The piece of fabric was placed onto a sterile workspace. We used a clean razor blade or sterile disposable scalpel to thoroughly scrape the entire marked stained fabric until clumps of fabric fibers formed. An ANDE swab pre-wetted with 2-3 drops of sterile water from a 30 mL drop-dispenser bottle (VWR; Catalog was used was used to collect the DNA-containing semen samples. #16354-421).

Figure 23:
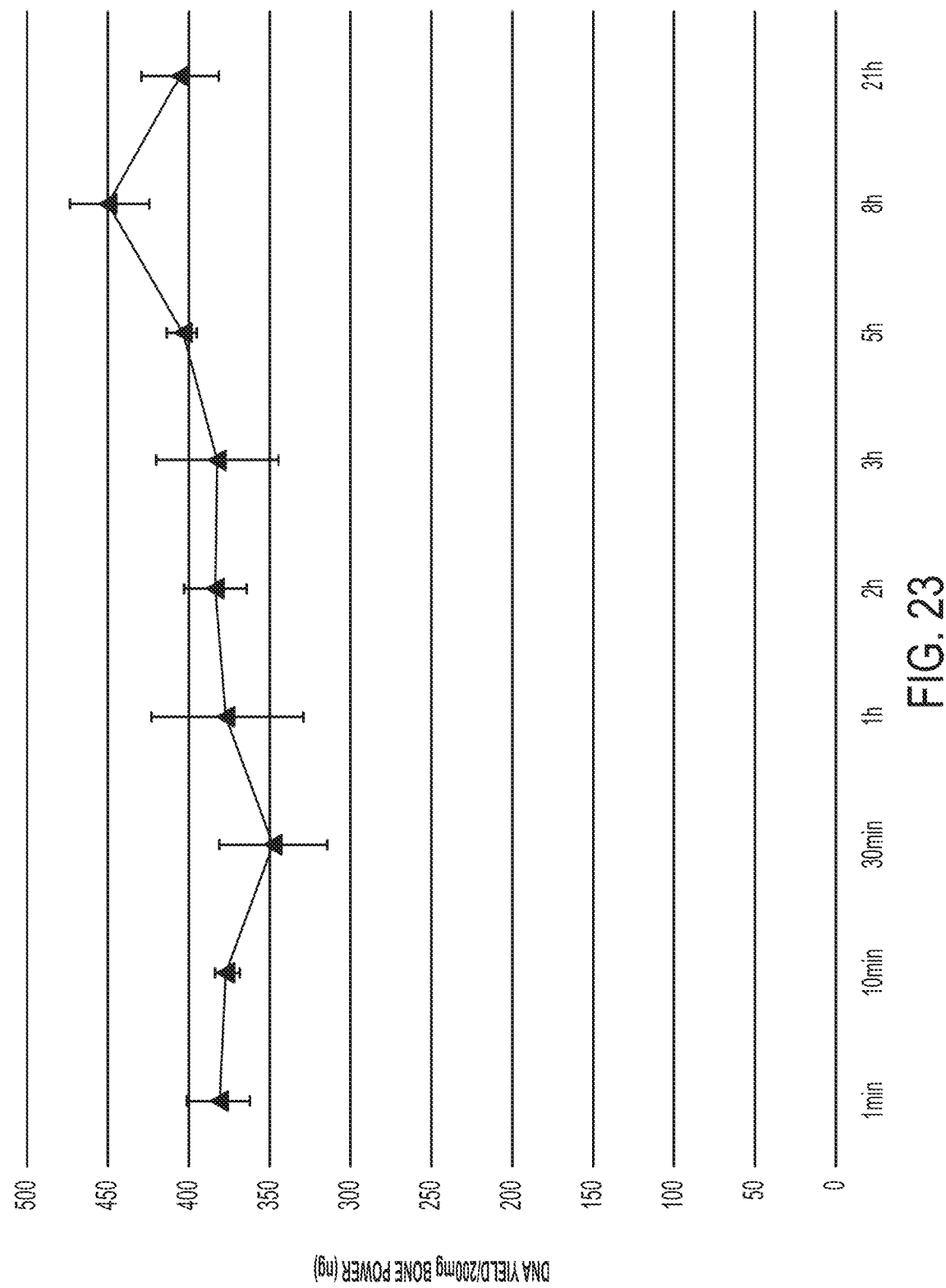
FIG. 23 is a time-course data showing demineralization of bone measured as purified DNA (in nanograms) as a function of time. The data demonstrates that overnight demineralization is not required for STR analysis. Demineralization times of one minute are sufficient for STR analysis using the inventive compositions and methods of this invention.

As shown in FIG. 23, to collect DNA-containing semen samples, we moved the clumps of fiber to one side of the stained fabric piece, and swabbed the surface of previously scraped material by moving the swab head back and forth to collect residual cellular materials. Next, 1 drop of molecular biology grade water was placed onto the swab head and collected the clumps of fiber. In some cases, an additional 1-2 drops of molecular biology grade water was placed onto the clumps of fiber to ensure they are securely attached to the swab head. We then smoothed the surface of the swab head with the razor blade or sterile scalpel to further secure the fibers. In addition, we also swabbed the razor blade or sterile scalpel that was used to scrape the article of clothing onto the dried portion of the swab head. Usually the dried portion of the swab head was closer to the plastic shaft. Finally, we loaded 50 µl of 150 mM DL-Dithiothreitol (DTT) (Sigma Aldrich; Catalog #43816) or 50 µl of 50 mM Tris(2-carboxyethyl)phosphine hydrochloride (TCEP) (Sigma Aldrich; Catalog #646547) onto the fabric bundles and then rotating the swab to ensure coverage of the entire swab and return the swab with the fiber bundle to the clear plastic tube. The DTT or TCEP was used to break down the disulfide bonds in sperm nuclear membranes.

Step 3: DNA Analysis by Performing a Rapid DNA Run on the ANDE System

We processed and analyzed nucleic acids on the swab using the ANDE I-Chip. Specifically, we removed the protective plastic seal from the first swab chamber (found on the top of the I-Chip), selected "Perform Run" on the ANDE instrument, followed the screens for scanning the swab RFID using the swab caps only, entered the sample ID, and inserted the swab into the swab chamber by pressing down the swab until the swab cap clicked securely into place.

Figure 24:
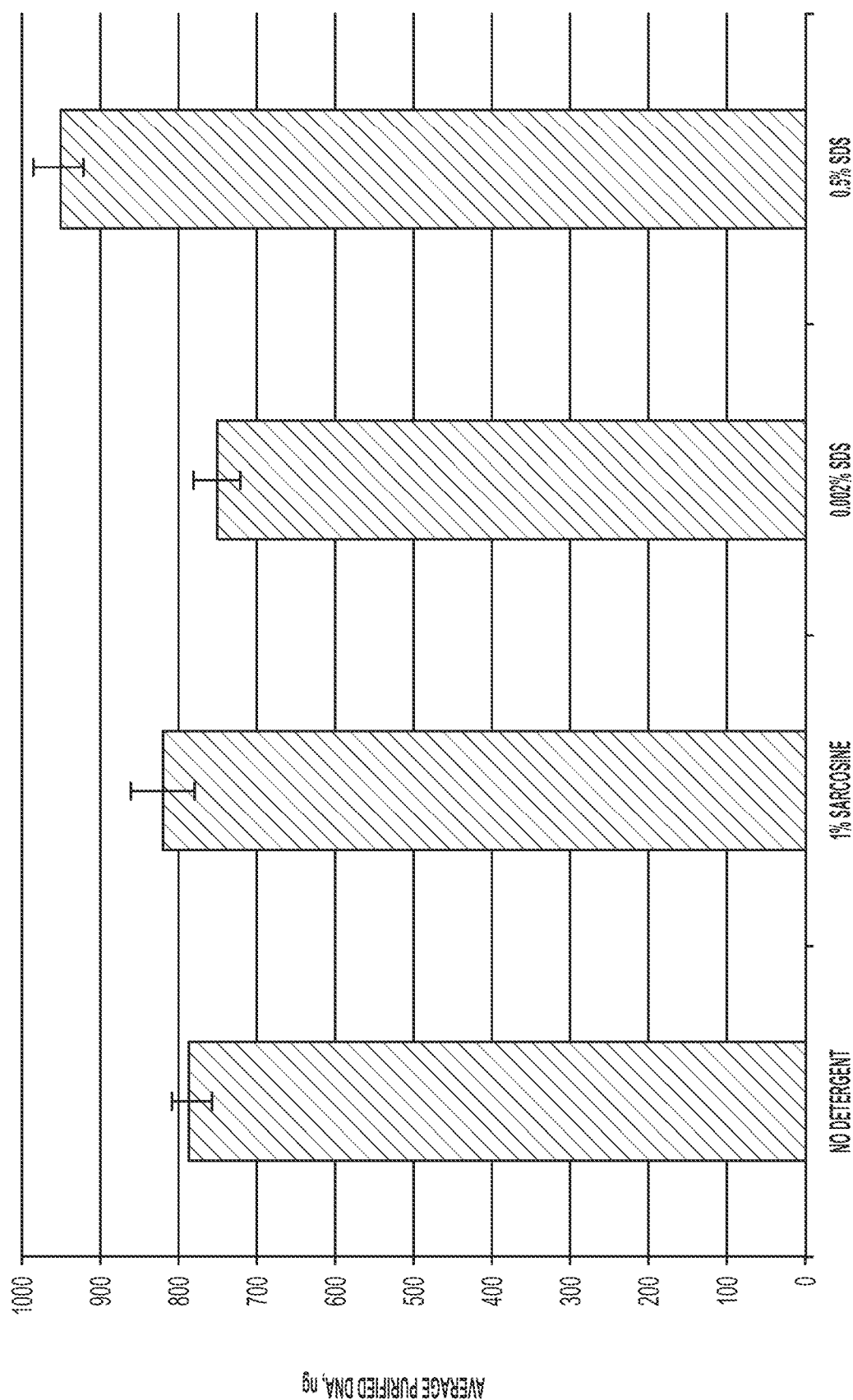
FIG. 24 is a plot showing the average amount of purified DNA (in nanograms) using EDTA with and without detergents. This data is a comparison of simplified demineralization buffers that can be used in this invention. Data also shows that a simple 0.5 M EDTA buffer is sufficient to demineralize bone and obtain sufficient amounts of DNA for STR analysis.
Figure 25:
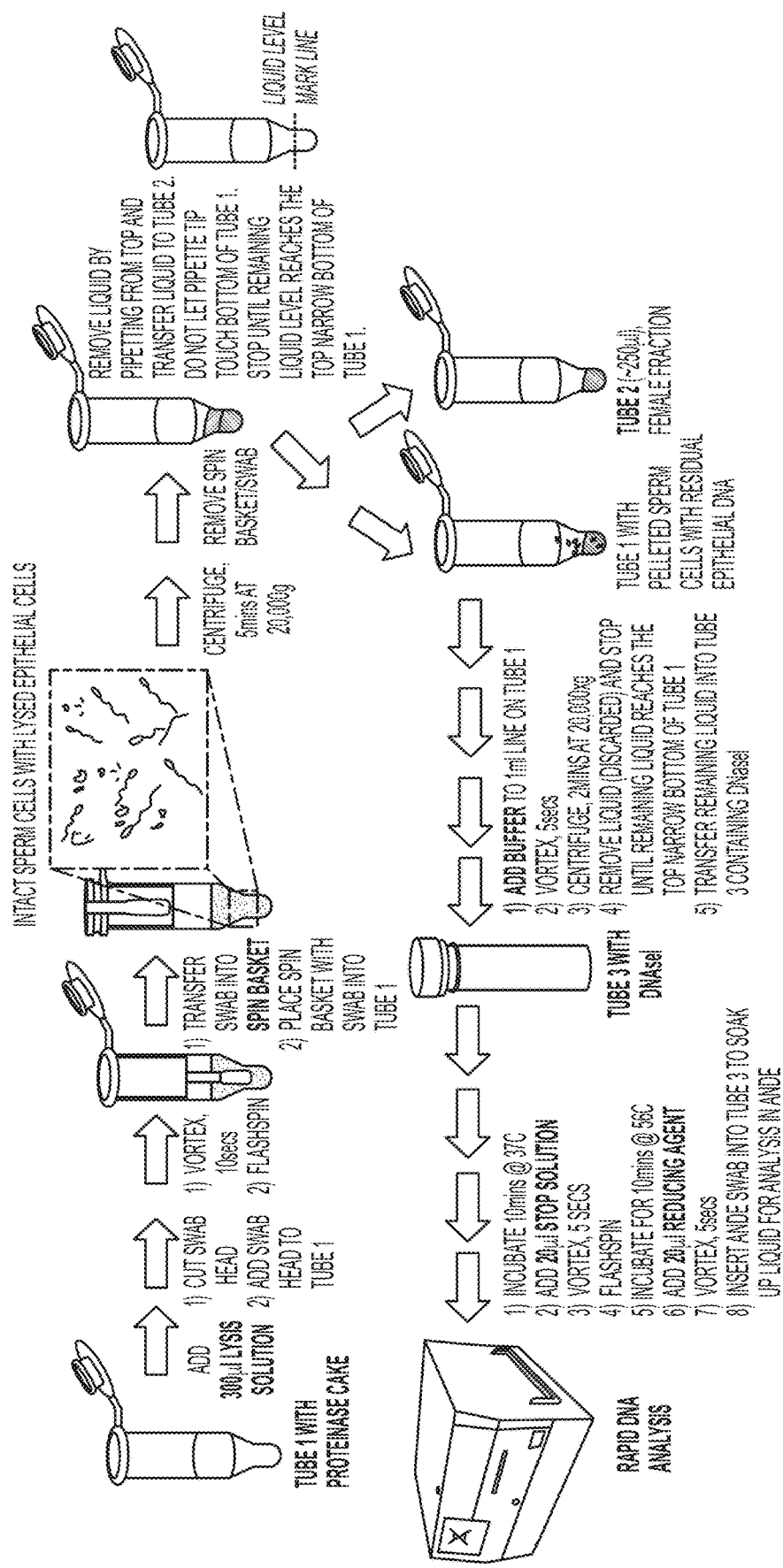
FIG. 25 shows the 32-minute protocol developed for processing sexual assault kits.
Figure 26:
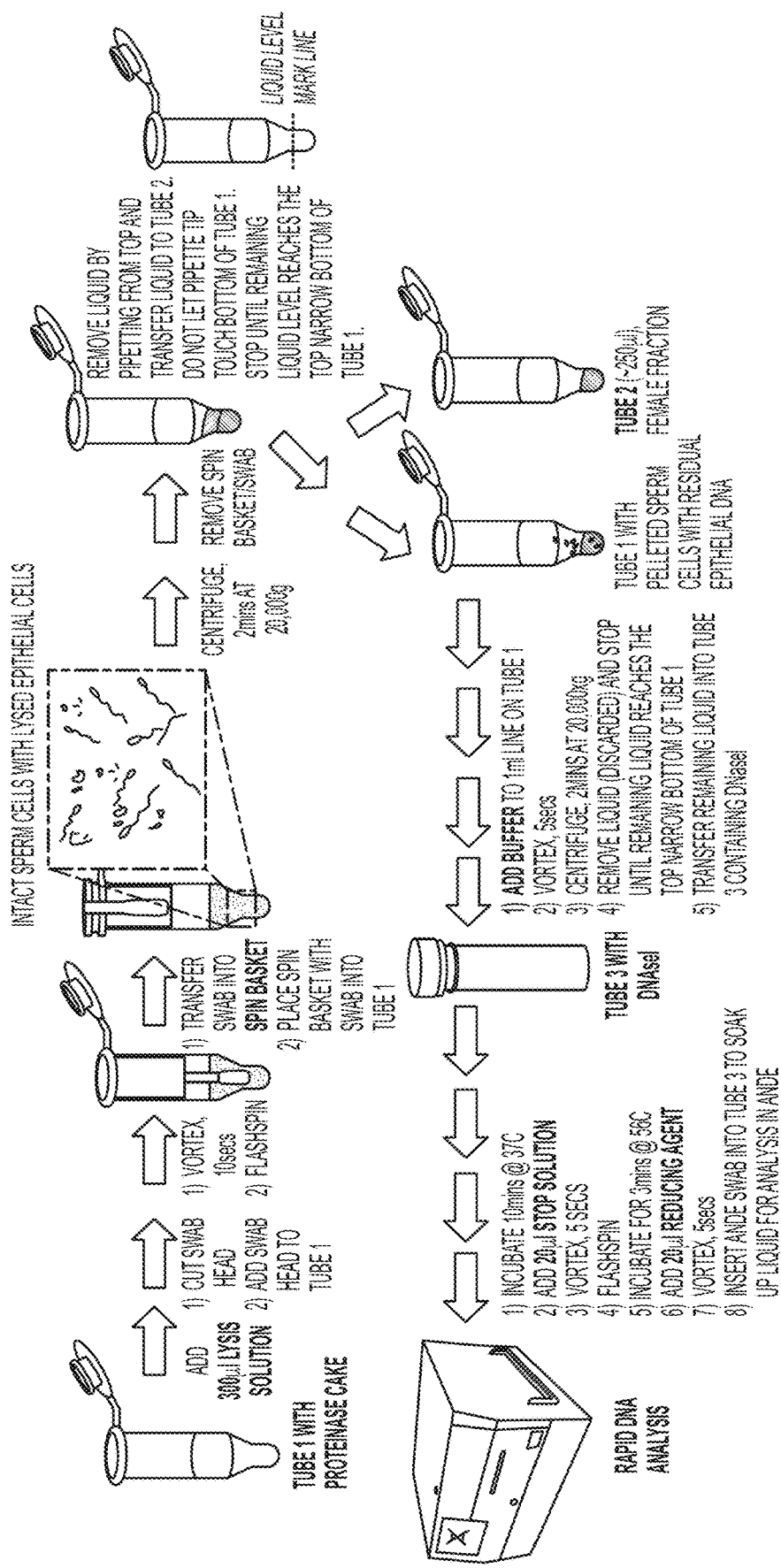
FIG. 26 shows the 22-minute protocol developed for processing sexual assault kits. Centrifugation time to separate intact sperm cells from the lysed epithelial fraction has been reduced from 5 minutes to 2 minutes at 20000×g. Incubation time for the stop solution to deactivate the nuclease was also reduced from 10 minutes to 3 minutes at 56 C.
Figure 28:
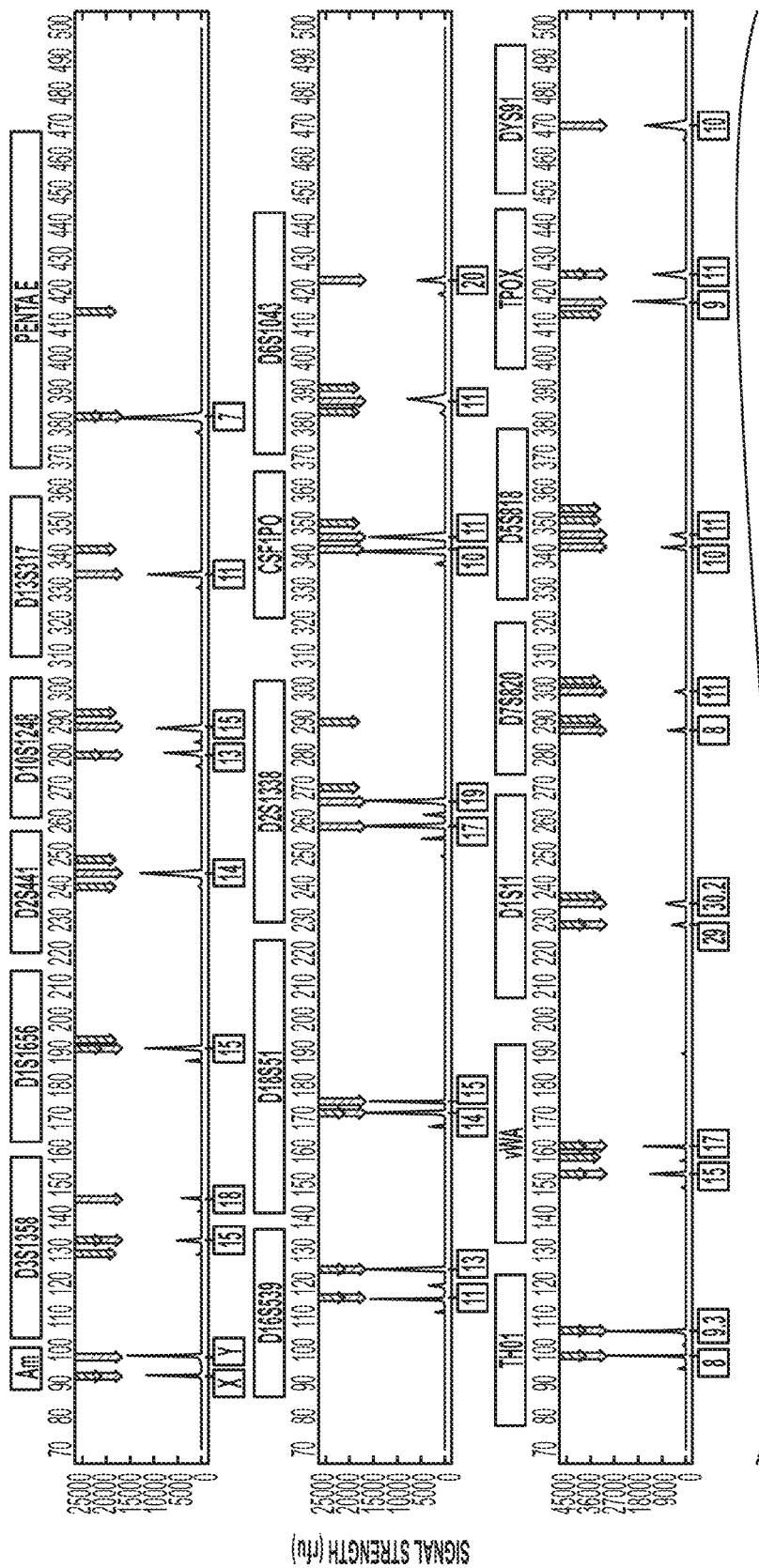
FIG. 28 shows a full 27-locus male STR profile of nucleic acid purified from male fraction isolated from vaginal swab (Donor couple A/B) collected 24 hrs post-coitus using the 32-minute protocol. Male genotype is indicated by blue arrows based on processed male buccal reference swab. Female genotype is indicated by red arrows based on processed female buccal reference swab.
Figure 28:
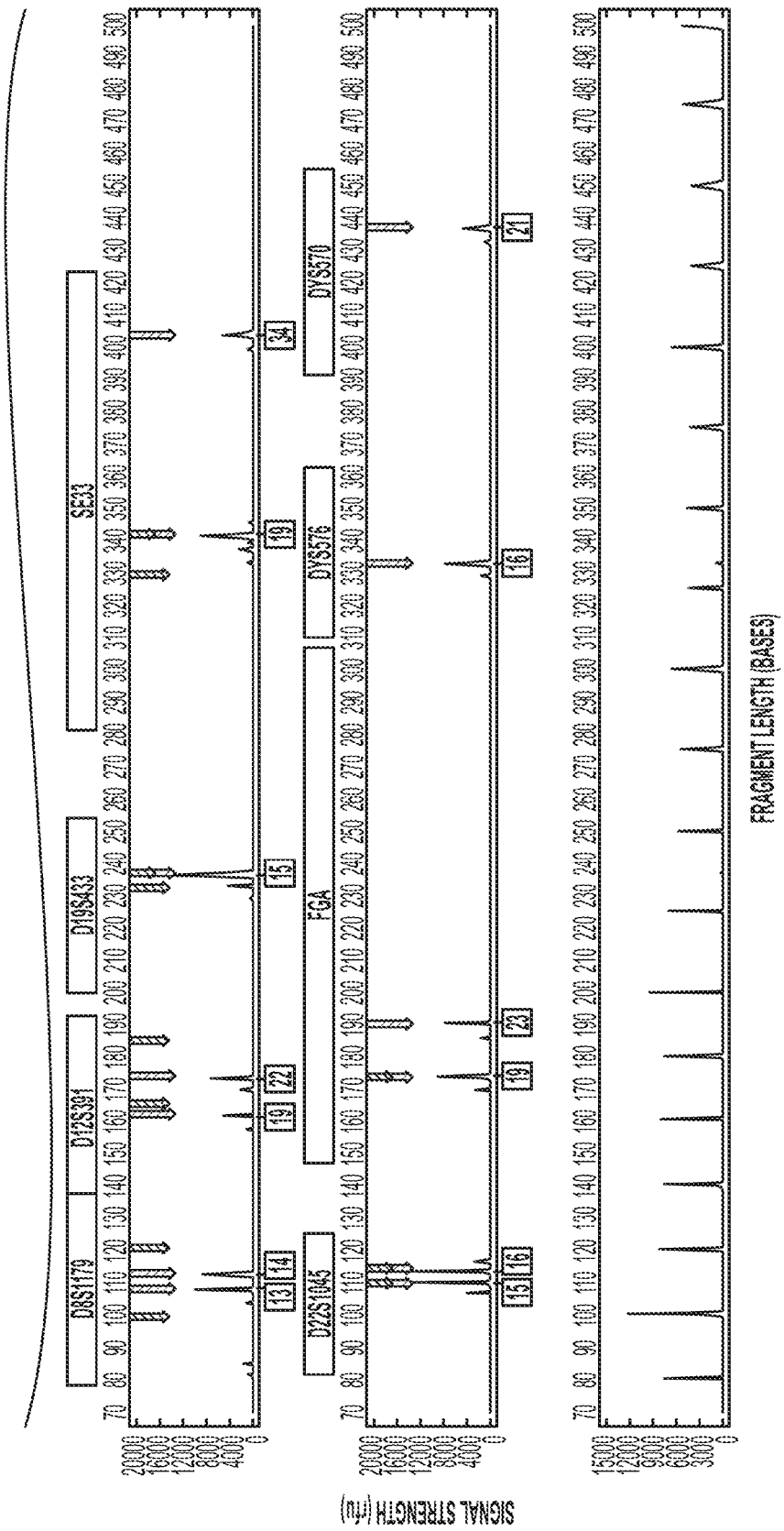
Figure 29:
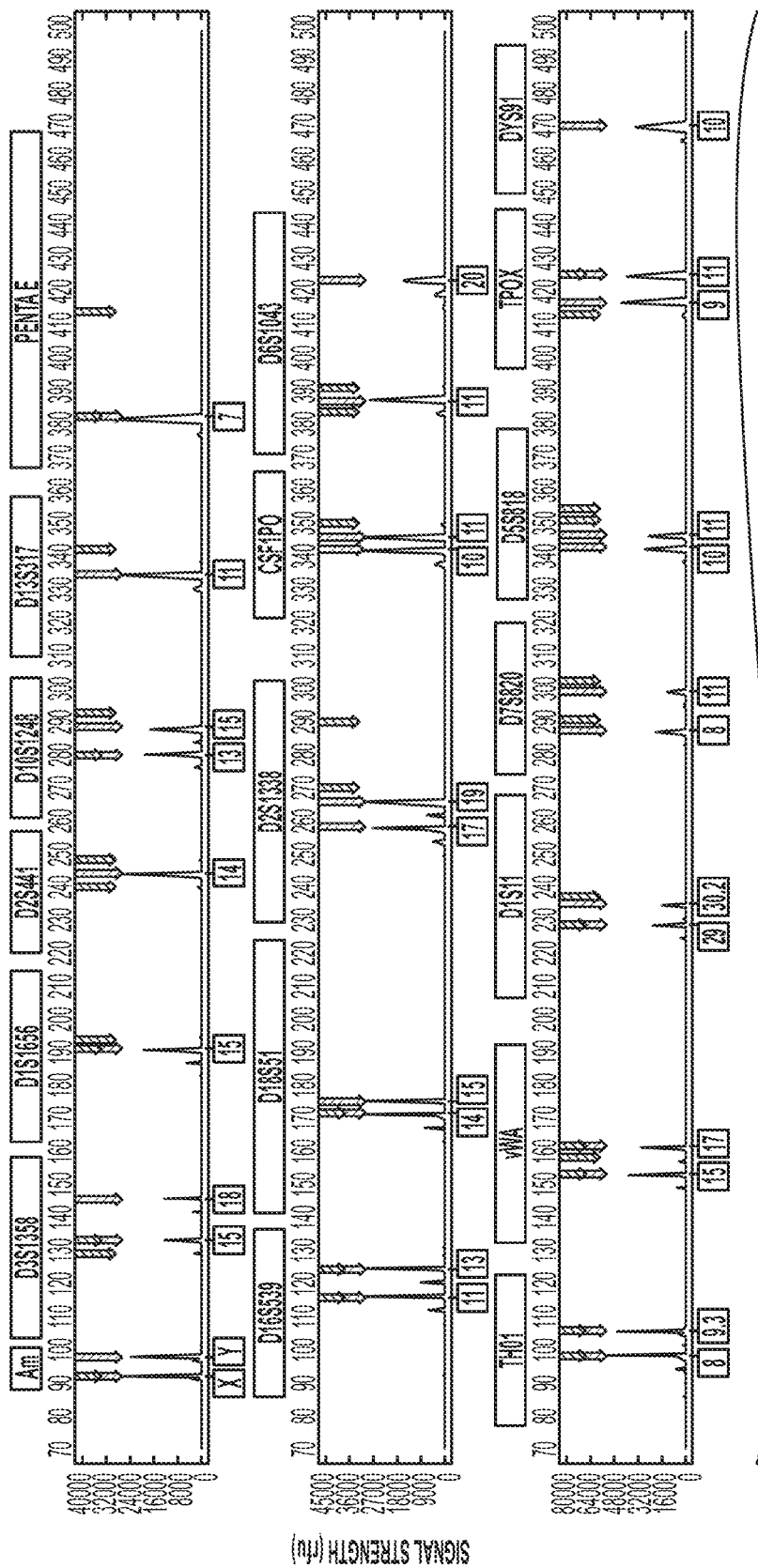
FIG. 29 shows a full 27-locus male STR profile of nucleic acid purified from male fraction isolated from vaginal swab (Donor couple A/B) collected 48 hrs post-coitus using the 32-minute protocol. Male genotype is indicated by blue arrows based on processed male buccal reference swab. Female genotype is indicated by red arrows based on processed female buccal reference swab.
Figure 29:
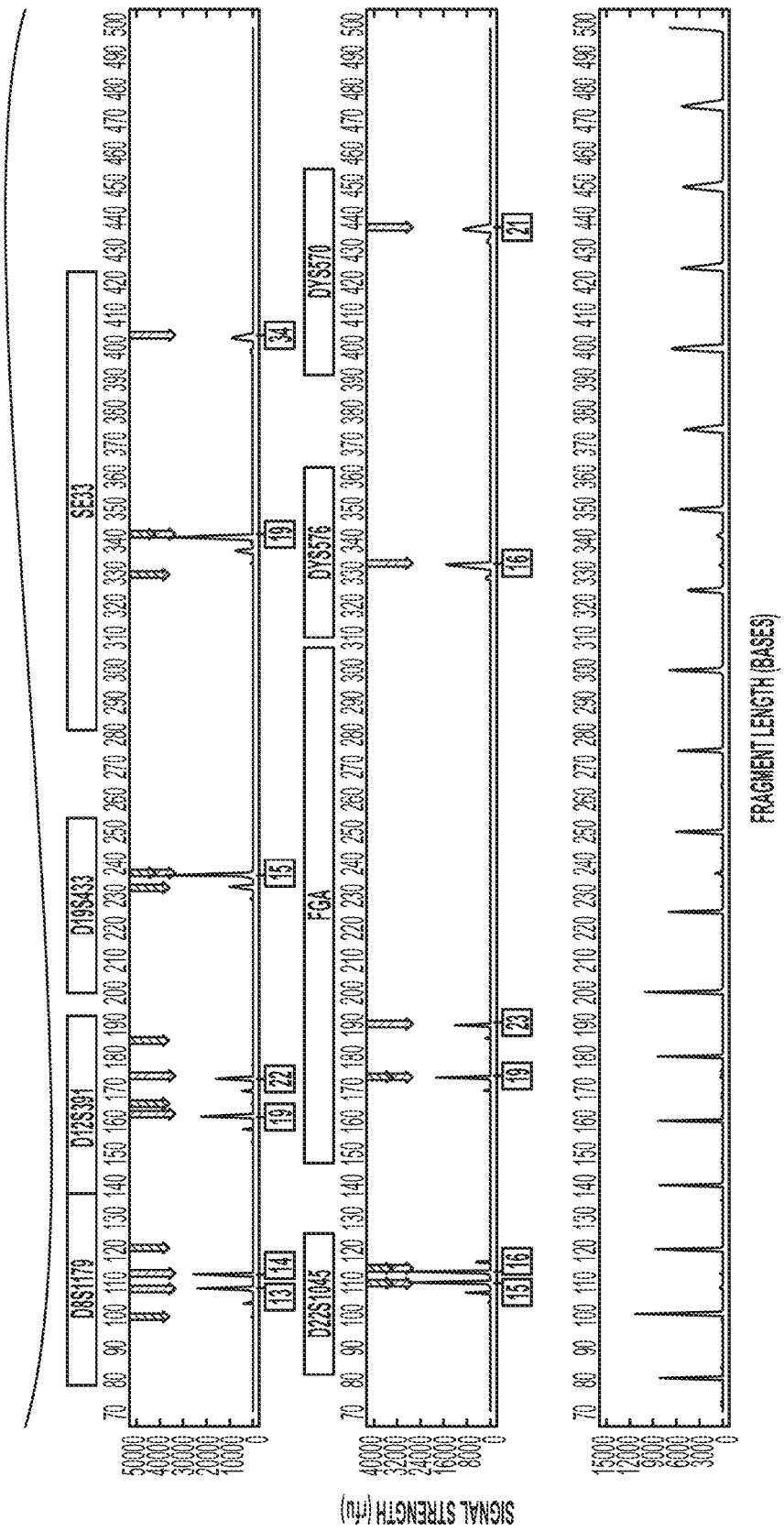
Figure 30:
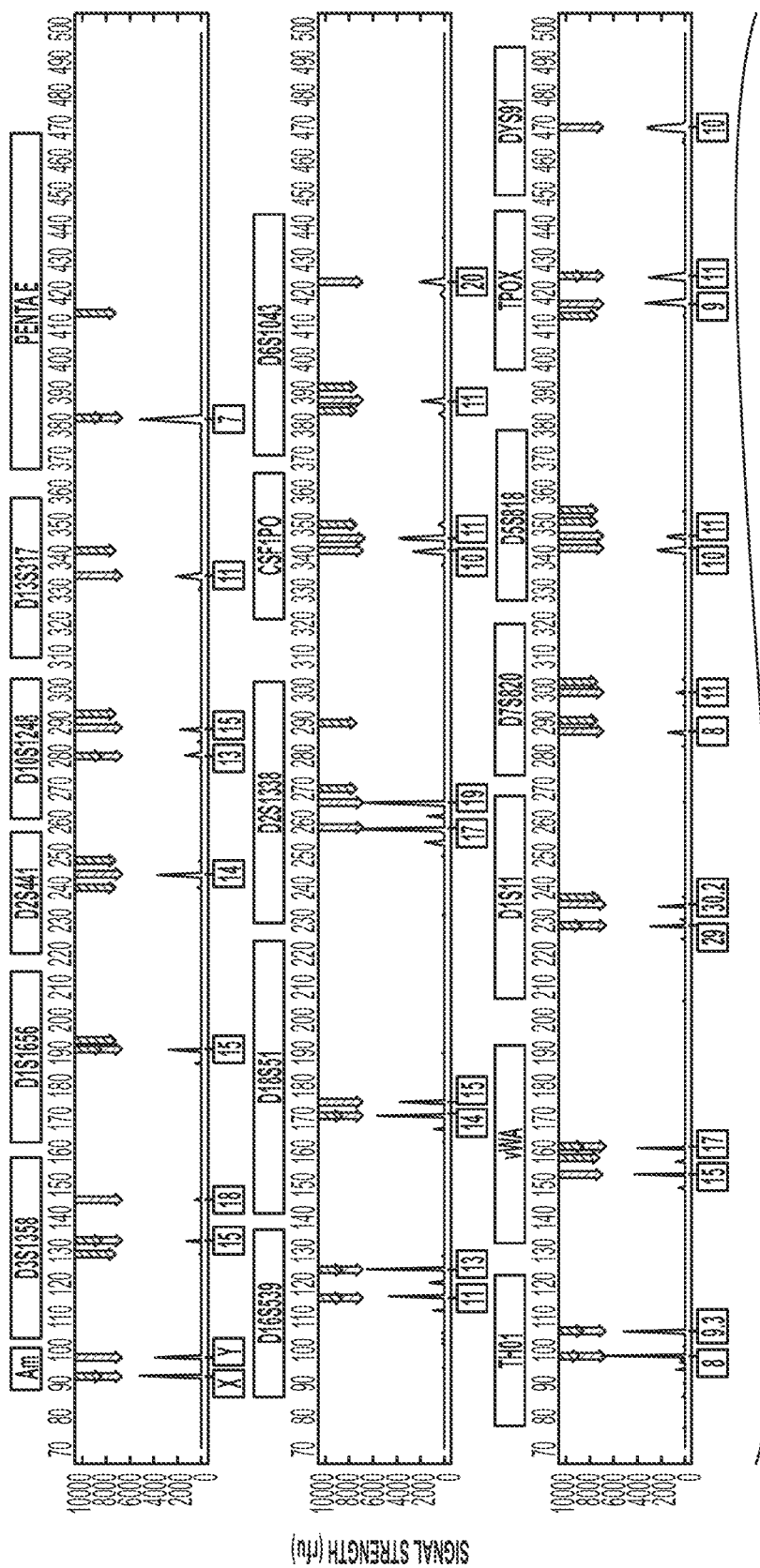
FIG. 30 shows a full 27-locus male STR profile of nucleic acid purified from male fraction isolated from vaginal swab (Donor couple A/B) collected 72 hrs post-coitus using the 32-minute protocol. Male genotype is indicated by blue arrows based on processed male buccal reference swab. Female genotype is indicated by red arrows based on processed female buccal reference swab.
Figure 30:
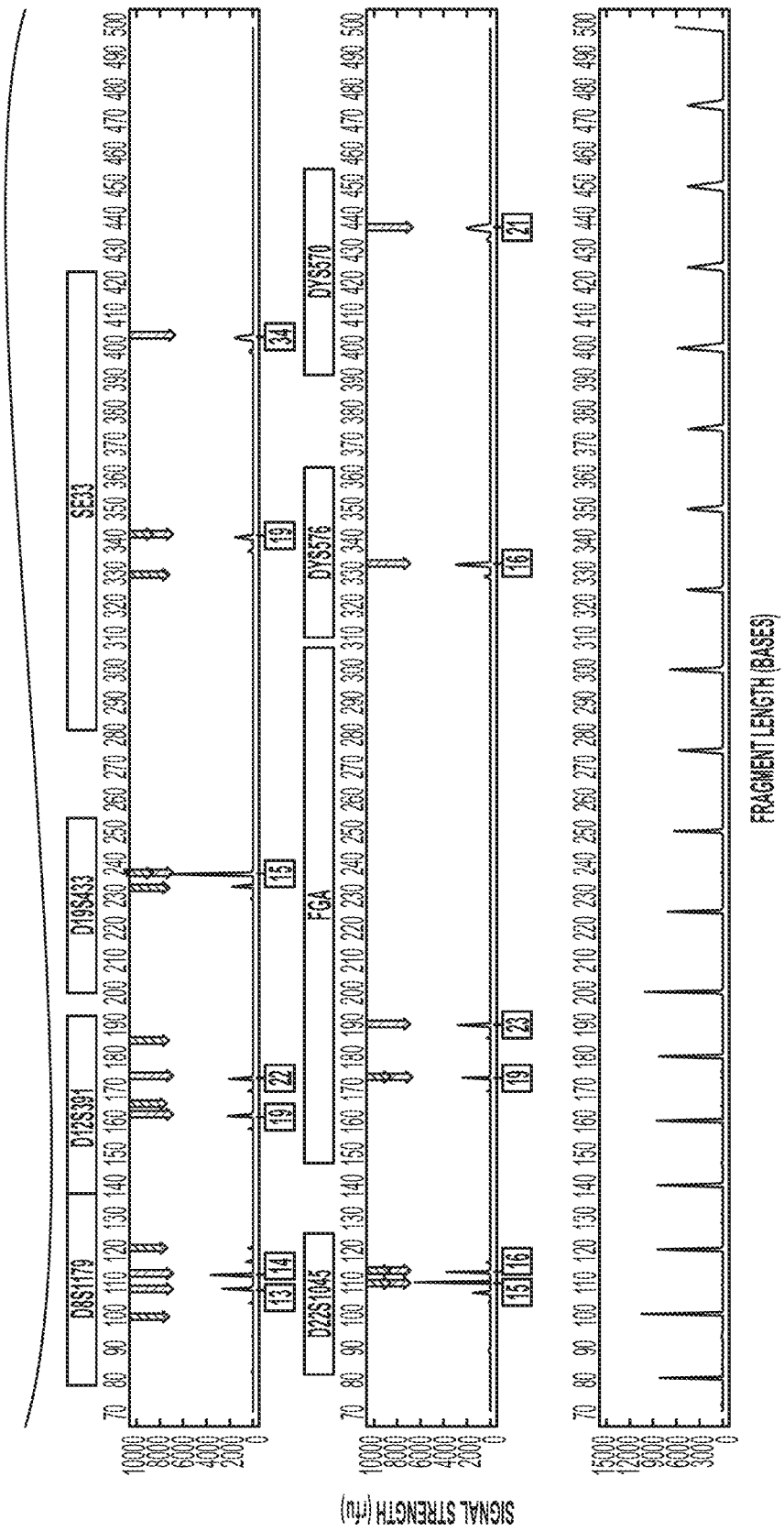
Figure 31:
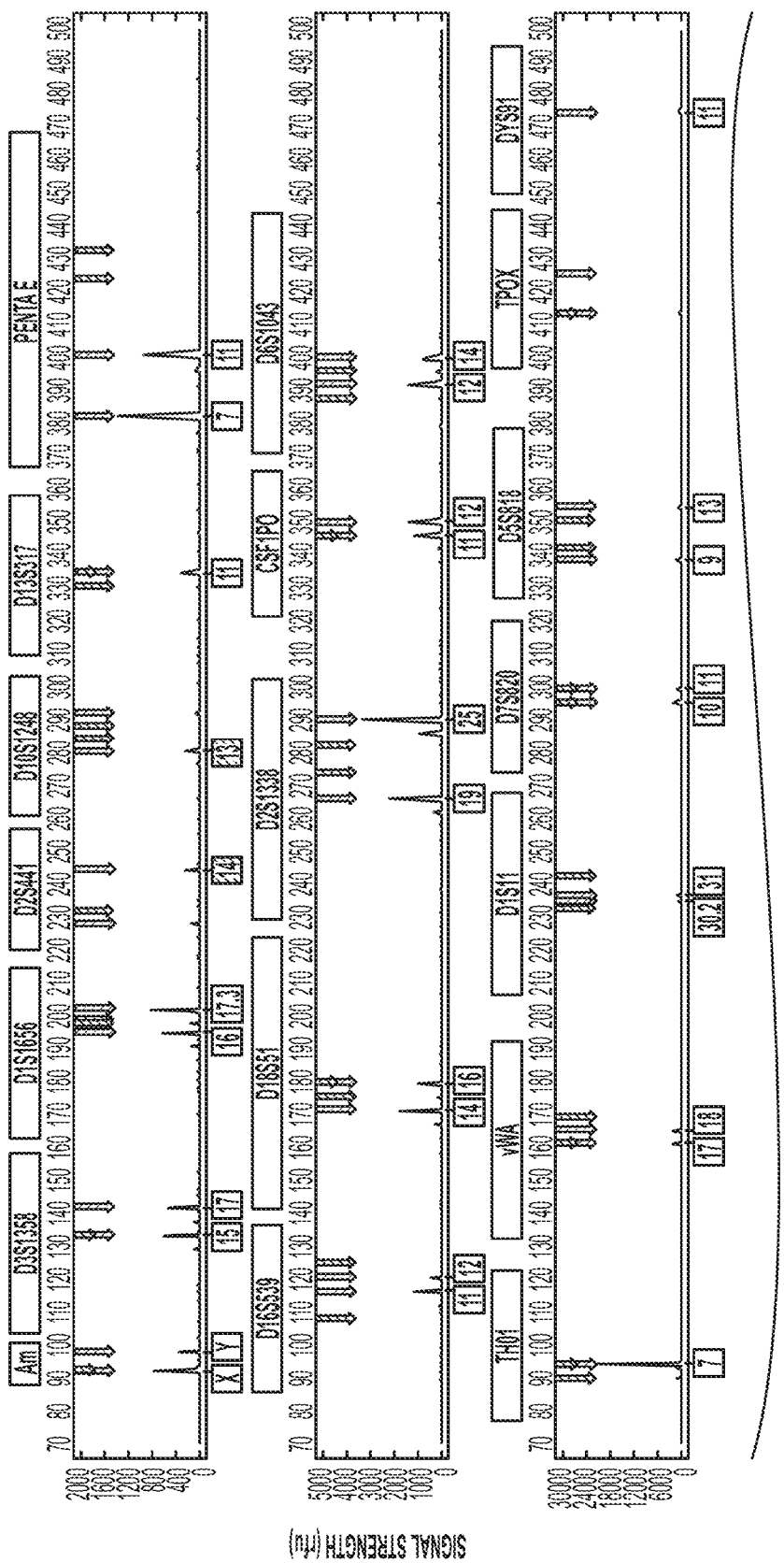
FIG. 31 shows a partial 27-locus male STR profile (24 of 27) of nucleic acid purified from male fraction isolated from vaginal swab (Donor couple C/D) collected 72 hrs post-coitus using the 32-minute protocol. STR profile is missing alleles for D2S441, D10S1248, and TPOX. Male genotype is indicated by blue arrows based on processed male buccal reference swab. Female genotype is indicated by red arrows based on processed female buccal reference swab.
Figure 31:
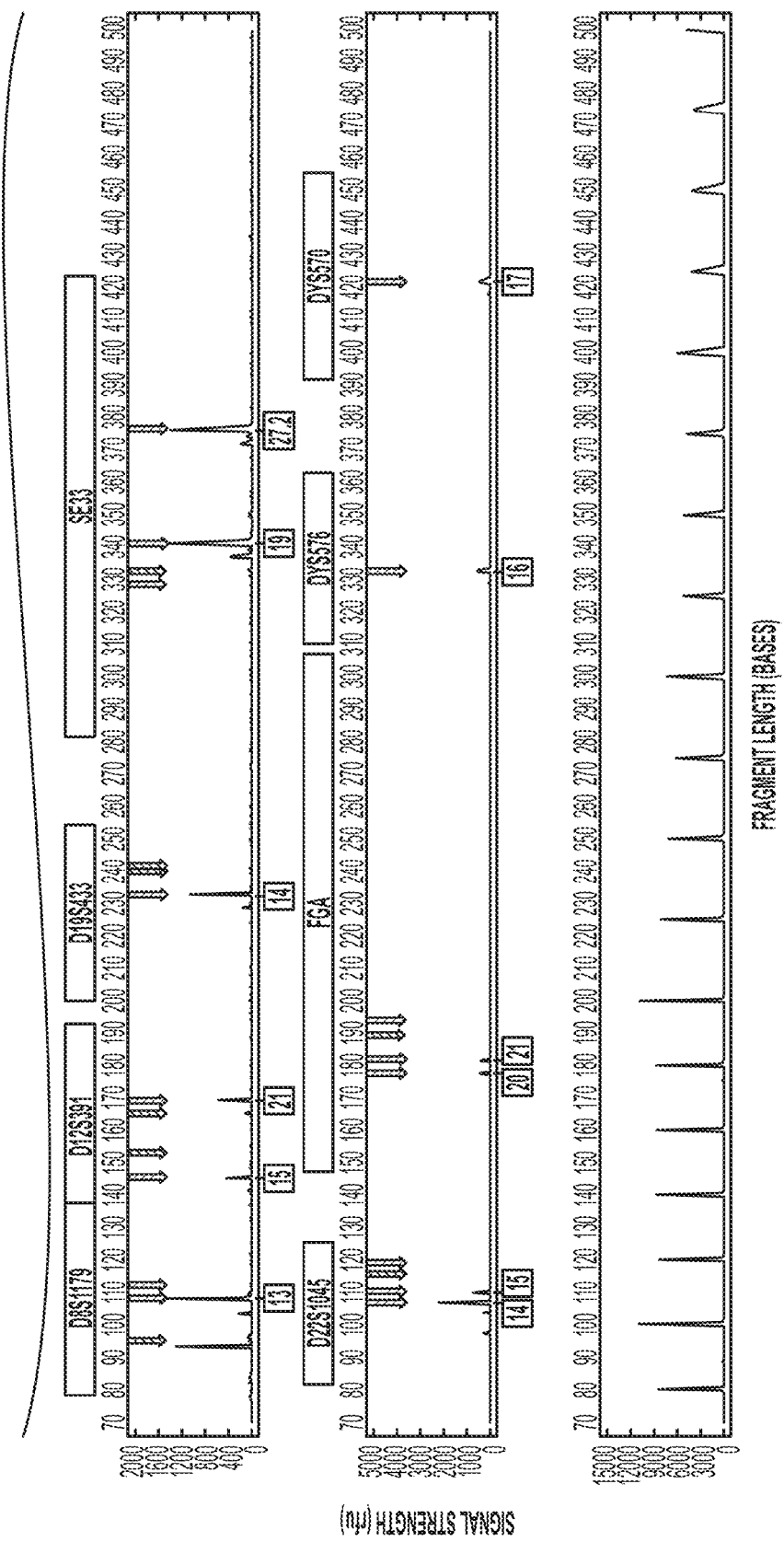
Figure 32:
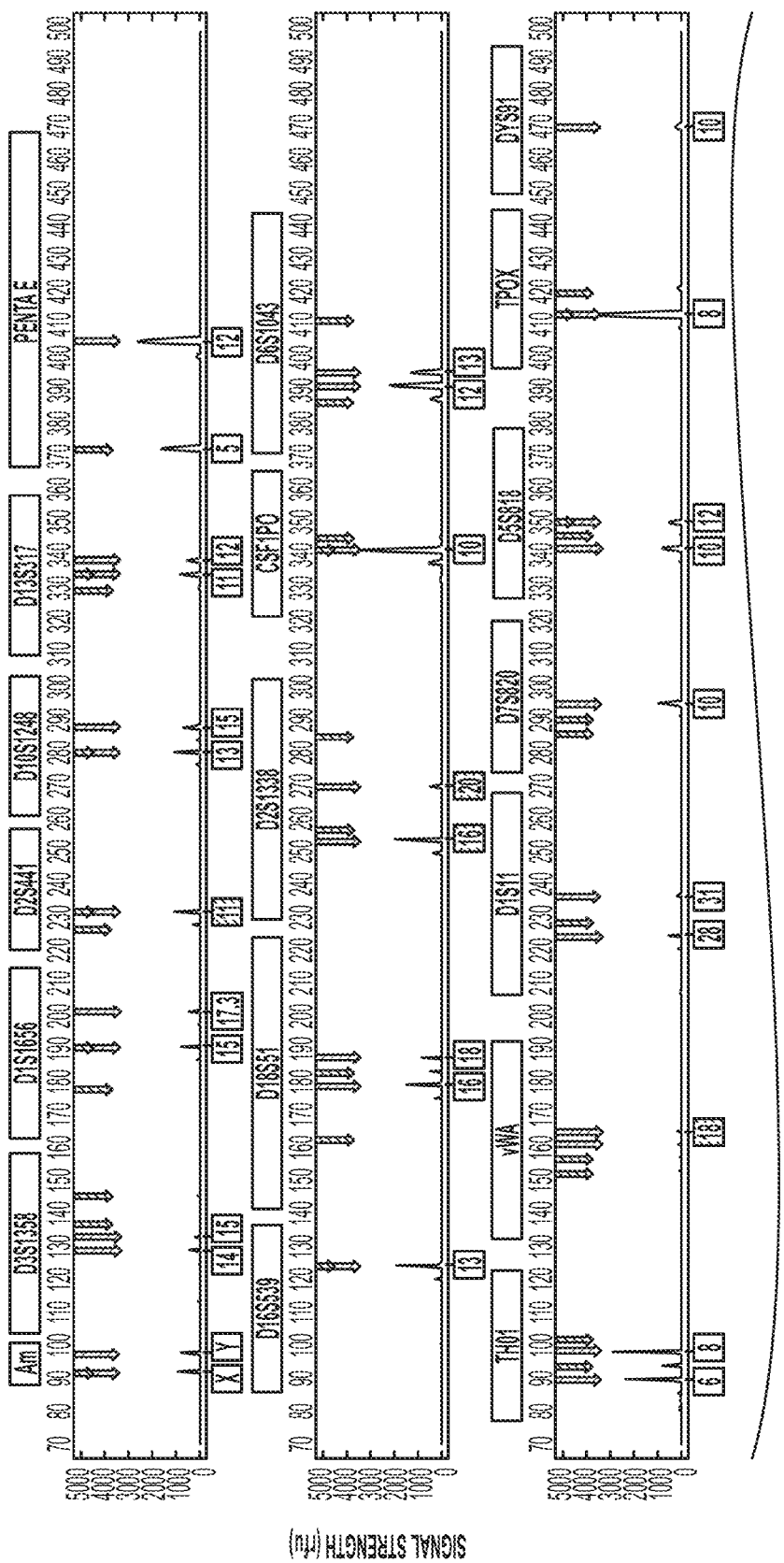
FIG. 32 shows a partial 27-locus male and female mixture (with female minor) STR profile of nucleic acid purified from male fraction isolated from vaginal swab (Donor couple E/F) collected 72 hrs post-coitus using the 32-minute protocol. Male STR profile is missing an allele for vWA. Male genotype is indicated by blue arrows based on processed male buccal reference swab. Female genotype is indicated by red arrows based on processed female buccal reference swab.
Figure 32:
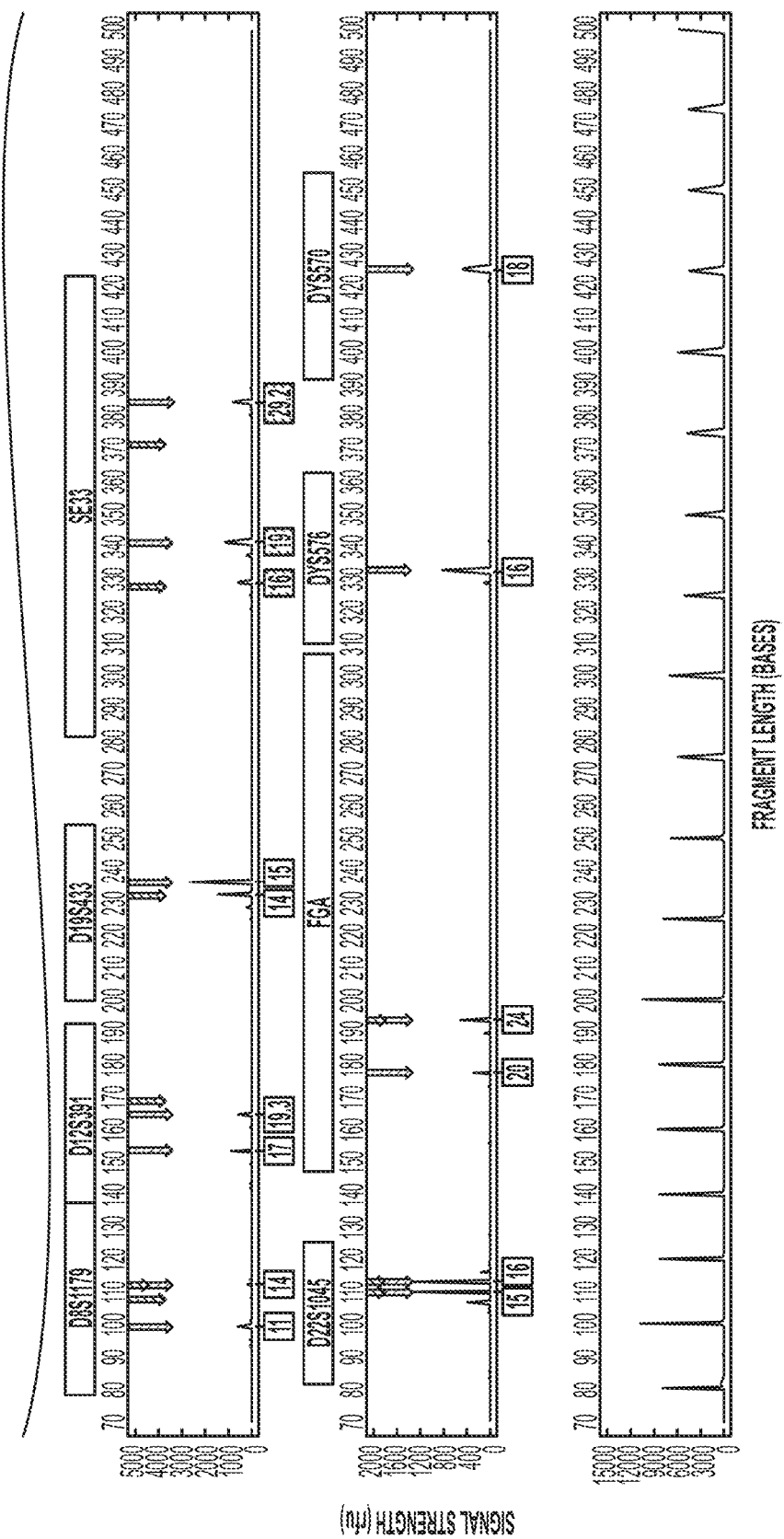
Figure 33:
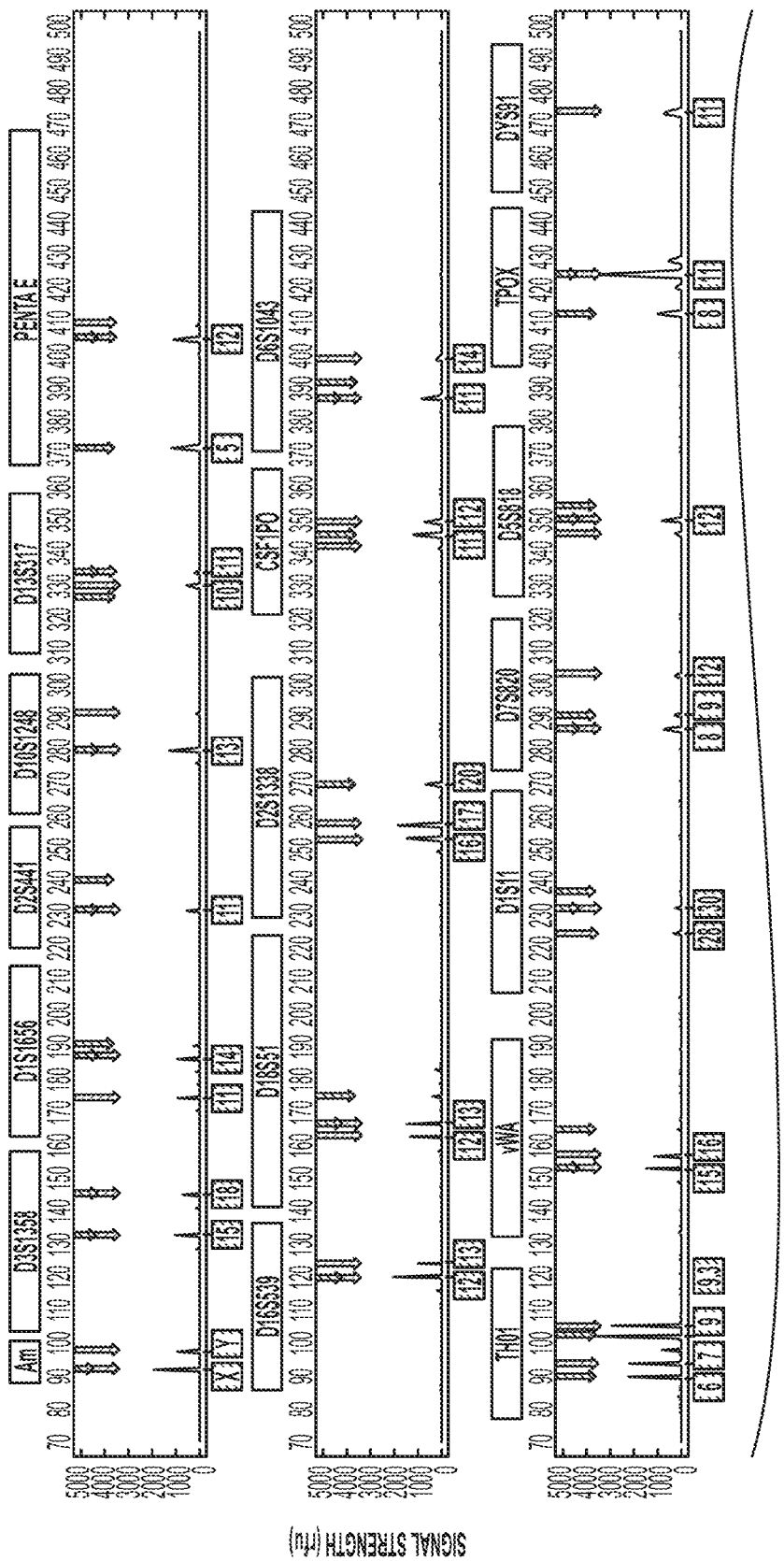
FIG. 33 shows a partial 27-locus male and female mixture (with female major) STR profile of nucleic acid purified from male fraction isolated from vaginal swab (Donor couple G/H) collected 72 hrs post-coitus using the 32-minute protocol. Male STR profile is missing alleles for D10S1248, PentaE, D5S818, CSF1PO, and SE33. Male genotype is indicated by blue arrows based on processed male buccal reference swab. Female genotype is indicated by red arrows based on processed female buccal reference swab.
Figure 33:
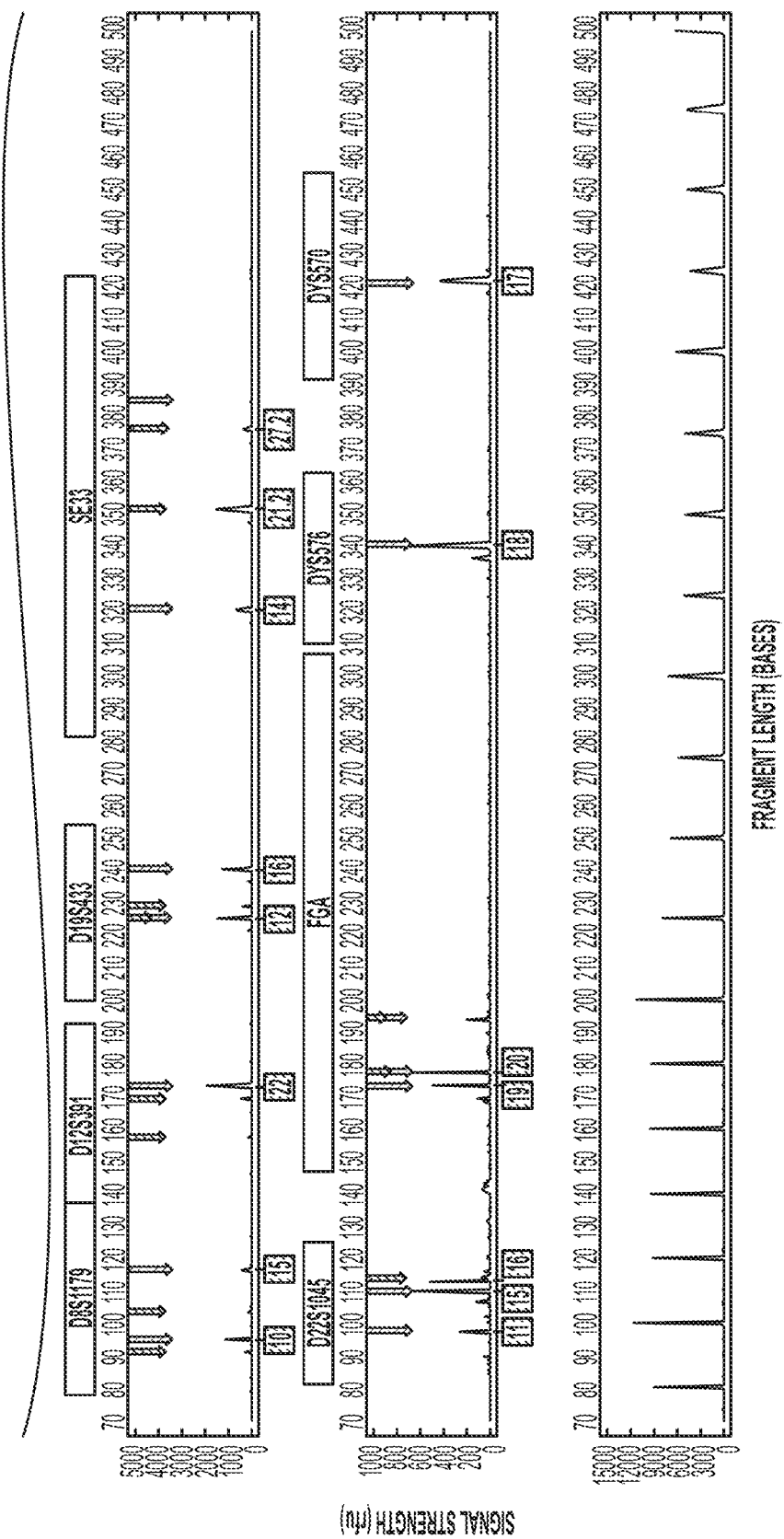
Figure 34:
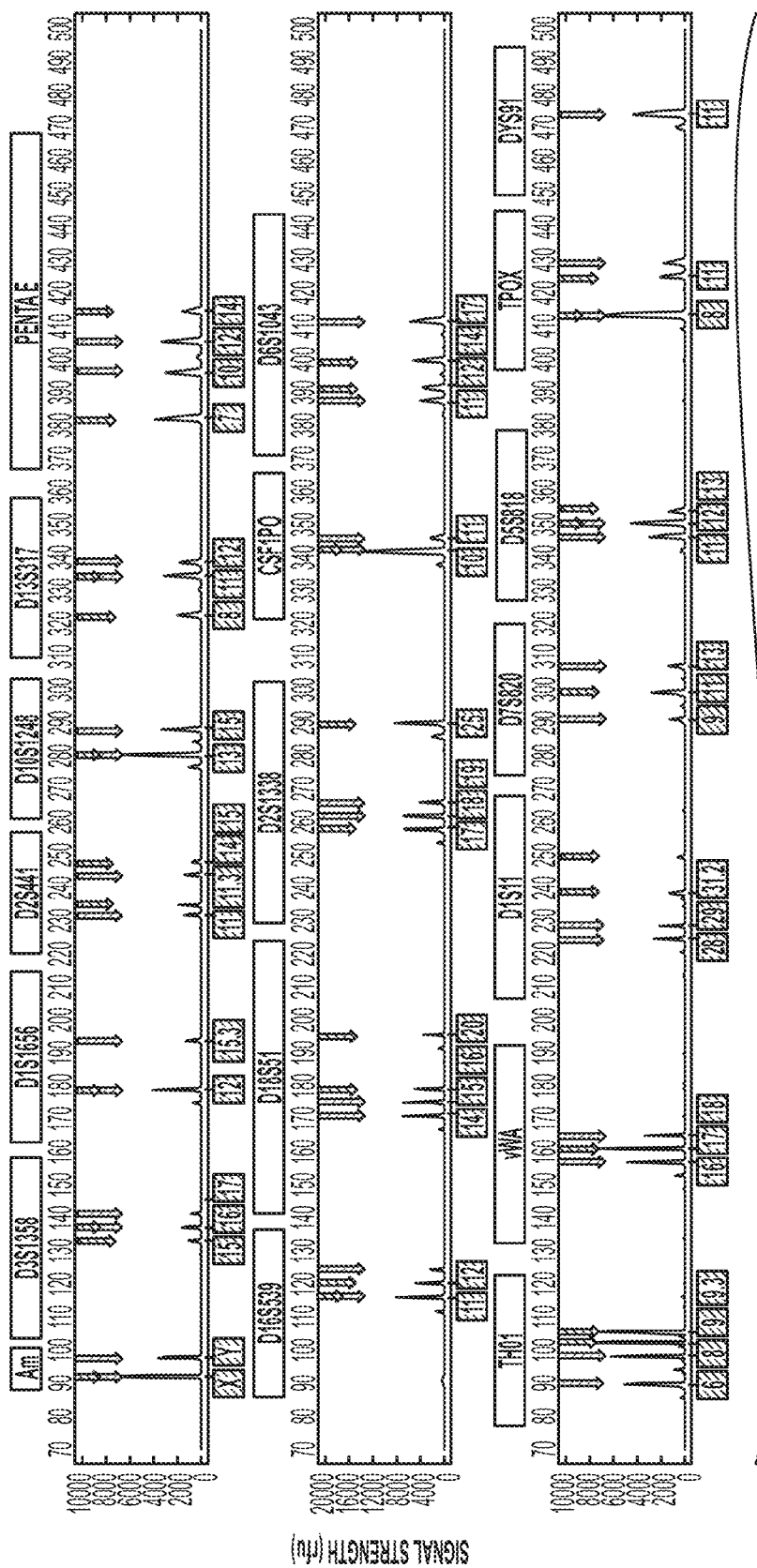
FIG. 34 shows a full 27-locus 1:1 male and female mixture STR profile of nucleic acid purified from male fraction isolated from vaginal swab (Donor couple I/J) collected 72 hrs post-coitus using the 32-minute protocol. Male genotype is indicated by blue arrows based on processed male buccal reference swab. Female genotype is indicated by red arrows based on processed female buccal reference swab.
Figure 34:
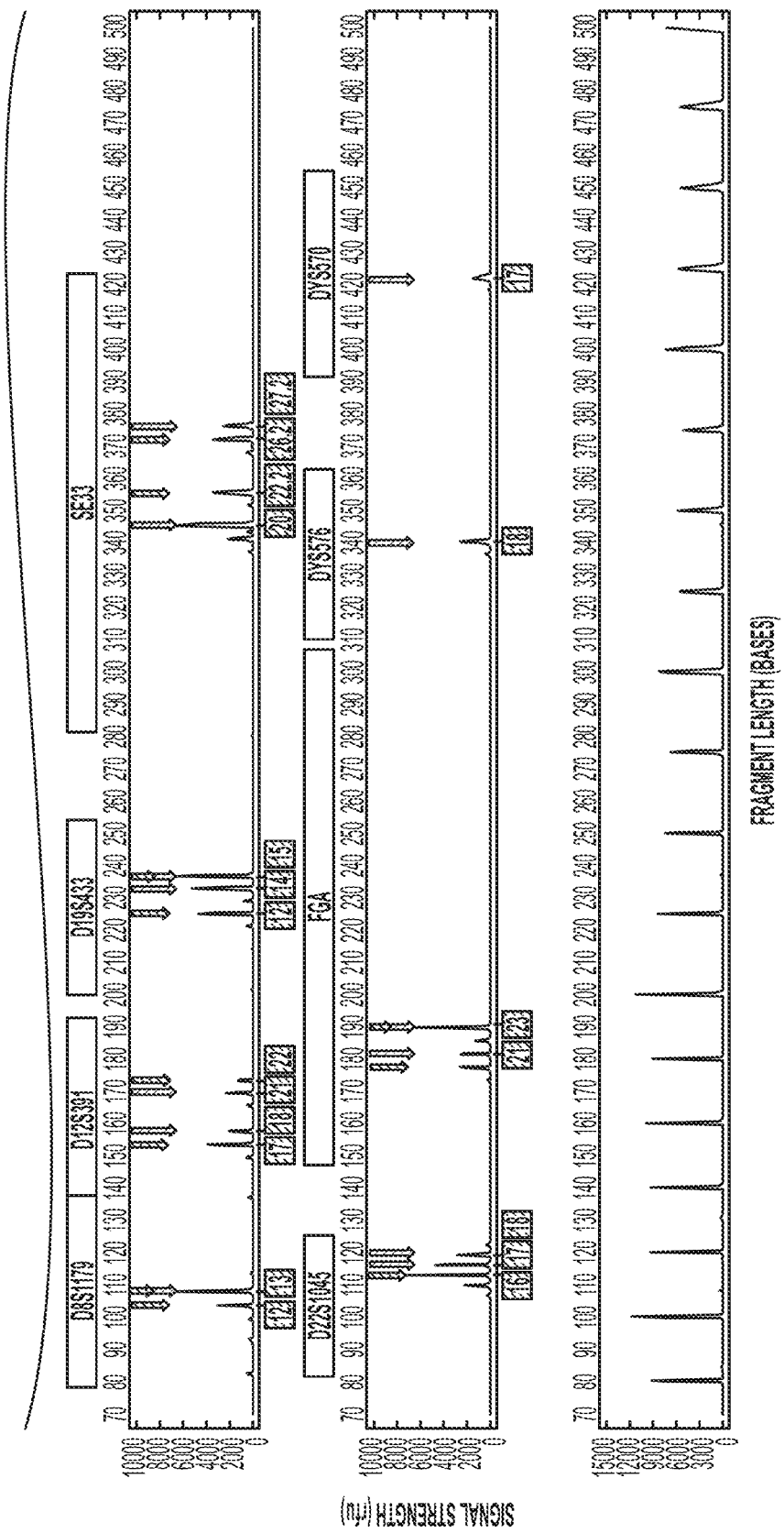
Figure 35:
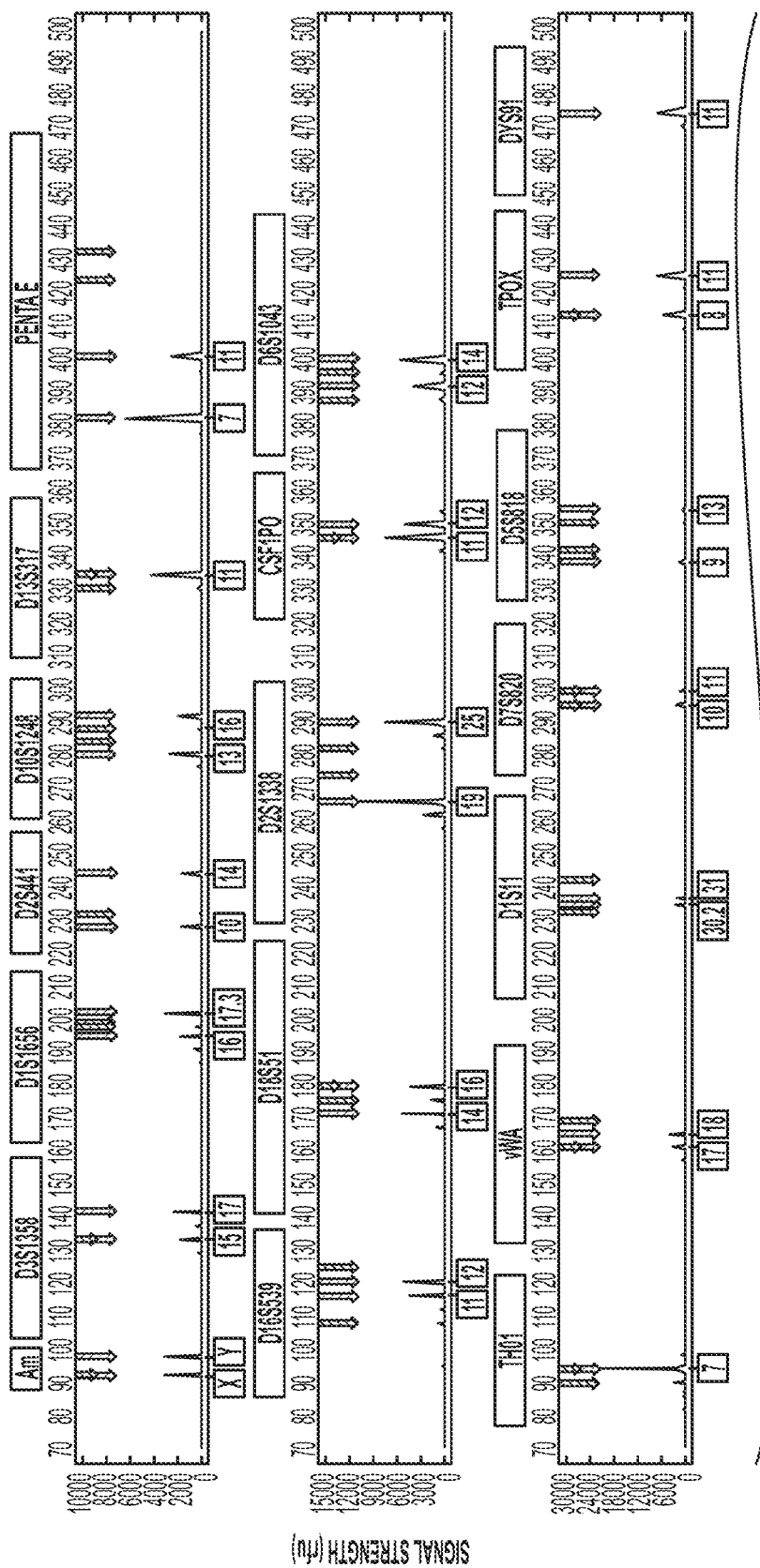
FIG. 35 shows a full 27-locus male STR profile of nucleic acid purified from male fraction isolated from vaginal swab (Donor couple C/D) collected 72 hrs post-coitus using the 22-minute protocol. Male genotype is indicated by blue arrows based on processed male buccal reference swab. Female genotype is indicated by red arrows based on processed female buccal reference swab.
Figure 35:
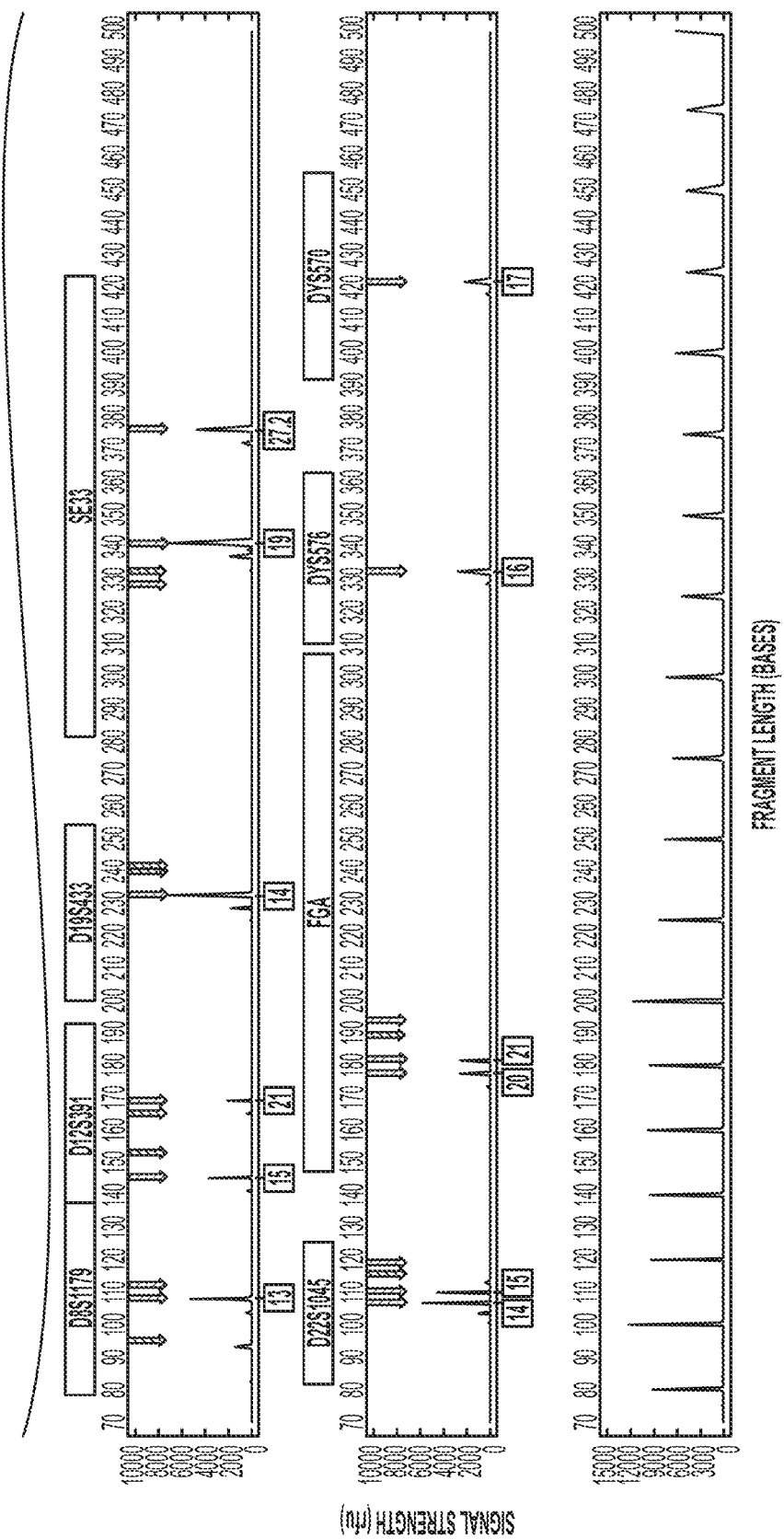

As a result, full STR profiles of nucleic acids from the dried semen on clothing were successfully generated. Signal strength generated may vary depending on the donor and fabric material. See FIGS. 24 and 26 for the full 16-locus and 27-locus STR profiles, respectively of nucleic acids purified from dried semen samples on denim, and FIG. 25 for the full 16-locus STR profile of nucleic acids purified from dried semen samples on cotton.

Example 6

Extraction and Analysis of Nucleic Acids from Timed Post-Coital Vaginal Swabs And Swabs from Sexual Assault Kit (SAK)

Vaginal swabs from several donor pairs at 24 hr, 48 hr, and 72 hr post-coital intervals were processed and analyzed. The SAK protocol is summarized in FIG. 27. The swab was placed in Tube 1 containing ANDE's proteinase K and lysis solution. The sample was then vortexed for 10 seconds and flashspun. The swab was manually transferred into a spin basket that was inserted into Tube 1 and centrifuged for 5 minutes. This centrifugation time can be reduced to 2 minutes. Centrifugation rids the swab of any residual liquid that may contain biological material. The spin basket containing the dried swab was then removed and discarded. The aqueous phase is essentially the female fraction which contains lysed epithelial cells. The female fraction was carefully pipetted out and transferred into another microfuge tube, Tube 2. For analysis of the female fraction in the I-Chip, 5-100 of the fraction was placed on an ANDE swab. Sperm cells, if present, are pelleted at the bottom of the Tube 1. It is therefore important not to disturb the pellet or remove it by accident. The pipette tip should not touch the bottom of the tube and liquid approximately 500 can be retained to avoid sperm cell sample loss. The pellet with minimal liquid from the female fraction was then washed by adding a wash buffer containing $MgCl_2$ and $CaCl_2$ to the 1 ml line on Tube 1. The mixture was then vortexed for 5 seconds, centrifuged for 2 minutes at 20,000×g to repelletize the sperm. Approximately 50 µl of aqueous phase was retained, the remainder was discarded. Homogenized sperm was then transferred to Tube 3 containing 2000 U-10000 U of nuclease; 2000 U is sufficient amount to degrade soluble DNA for this work with incubation for 10 minutes at 37 C. The reaction was quenched by adding 20 µl of a Stop Solution containing 0.5 M EDTA and incubation for 10 minutes at 56 C; further reduction to 3 minutes at 56 C is sufficient to deactivate the nuclease. The nuclease used in this invention is recombinant DNAseI (Sigma Aldrich; Catalog #04536282001). Finally, DL-Dithiothreitol (DTT) (Sigma Aldrich; Catalog #43816) or Tris(2-carboxyethyl)phosphine carboxyethyl)phosphine hydrochloride (TCEP) (Sigma Aldrich; Catalog #646547) is added at a final concentration equal or close to 150 mM DTT and 50 mM TCEP, respectively and vortexed for 5 seconds. The resulting solution is the male fraction and can be collected with an ANDE swab for analysis in I-Chip.

Note that the teachings herein are applicable to a wide range of other samples. For example, the methods for vaginal swab processing can also be applied to separate male from female cells in cases or penile-oral and penile-anal penetration. Although the examples herein discussed settings of male rapists and female victims, cases of male rapist-male victim and female rapist-male victim are also seen, and these methods are effective in such cases.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A process for extracting nucleic acid from a semen sample, comprising:
    a. collecting said semen sample onto a swab;
    b. adding approximately 50 µl of a sperm disruptive agent to said swab, wherein said sperm disruptive agent is DTT in approximate concentration of 150 mM or TCEP in an approximate concentration of 50 mM;
    c. incubating said swab and said sperm disruptive agent mixture for one minute or less;
    d. transferring said swab directly into a rapid DNA processing system for further analysis without purification;
    e. obtaining at least one STR profile from said sample using said rapid DNA processing system.

2. The process of claim 1, wherein the semen sample is neat semen or a semen stain.

3. The process of claim 1, wherein at least seven STR loci are interrogated.

* * * * *